United States Patent
Kawai et al.

(10) Patent No.: US 10,987,042 B2
(45) Date of Patent: *Apr. 27, 2021

(54) DISPLAY SYSTEM AND DISPLAY DEVICE

(71) Applicant: NINTENDO CO., LTD., Kyoto (JP)

(72) Inventors: Eizi Kawai, Kyoto (JP); Masahiro Kondo, Kyoto (JP); Kazuhiro Hosoi, Kyoto (JP)

(73) Assignee: Nintendo Co., Ltd., Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/567,811

(22) Filed: Sep. 11, 2019

(65) Prior Publication Data
US 2020/0005913 A1    Jan. 2, 2020

Related U.S. Application Data

(63) Continuation of application No. 15/211,497, filed on Jul. 15, 2016, now Pat. No. 10,504,616, which is a
(Continued)

(30) Foreign Application Priority Data

Jan. 17, 2014  (WO) ............... PCT/JP2014/050851
Aug. 7, 2014   (WO) ............... PCT/JP2014/070931

(51) Int. Cl.
*G16H 10/60*  (2018.01)
*H04N 9/31*   (2006.01)
(Continued)

(52) U.S. Cl.
CPC ............. *A61B 5/16* (2013.01); *A47C 31/00* (2013.01); *A61B 5/0022* (2013.01); *A61B 5/024* (2013.01);
(Continued)

(58) Field of Classification Search
CPC .................................................. G16H 10/60
See application file for complete search history.

(56) References Cited

U.S. PATENT DOCUMENTS 6,809,653 B1   10/2004   Mann et al.
6,993,380 B1    1/2006   Modarres
(Continued)

FOREIGN PATENT DOCUMENTS

EP    2 570 976 A1    3/2013
JP    9-34424         2/1997
(Continued)

OTHER PUBLICATIONS

U.S. Appl. No. 15/211,497, filed Jul. 15, 2016, Display System and Display Device.
(Continued)

*Primary Examiner* — John W Miller
*Assistant Examiner* — Justin B Sanders
(74) *Attorney, Agent, or Firm* — Nixon & Vanderhye, P.C.

(57) ABSTRACT

An example of a display system includes a sensor, a projector, and control means. The sensor senses user information for calculating a state regarding sleep of a user. The user information is, for example, biological information such as pulse. The projector projects and displays a predetermined image. The projector, for example, projects the image upward to project and display the image on the ceiling. The control means controls the projector in accordance with a state regarding sleep, which is calculated on the basis of the user information.

20 Claims, 28 Drawing Sheets

Related U.S. Application Data continuation of application No. PCT/JP2014/078827, filed on Oct. 29, 2014.

(51) Int. Cl.

| | |
|---|---|
| *A61B 5/16* | (2006.01) |
| *G16H 40/63* | (2018.01) |
| *G16H 50/30* | (2018.01) |
| *G06F 16/22* | (2019.01) |
| *G06Q 30/02* | (2012.01) |
| *G16H 20/30* | (2018.01) |
| *G16H 40/67* | (2018.01) |
| *G16H 10/20* | (2018.01) |
| *G06Q 50/22* | (2018.01) |
| *A61B 5/00* | (2006.01) |
| *A61B 5/11* | (2006.01) |
| *A61B 5/024* | (2006.01) |
| *G06Q 20/10* | (2012.01) |
| *A63F 13/212* | (2014.01) |
| *A47C 31/00* | (2006.01) |
| *G06Q 30/06* | (2012.01) |
| *A61B 5/08* | (2006.01) |

(52) U.S. Cl.
CPC .............. *A61B 5/11* (2013.01); *A61B 5/1118* (2013.01); *A61B 5/165* (2013.01); *A61B 5/4806* (2013.01); *A61B 5/486* (2013.01); *A61B 5/4809* (2013.01); *A61B 5/4812* (2013.01); *A61B 5/7271* (2013.01); *A61B 5/742* (2013.01); *A61B 5/7405* (2013.01); *A63F 13/212* (2014.09); *G06F 16/2228* (2019.01); *G06Q 20/10* (2013.01); *G06Q 30/02* (2013.01); *G06Q 30/0641* (2013.01); *G06Q 50/22* (2013.01); *G16H 10/20* (2018.01); *G16H 10/60* (2018.01); *G16H 20/30* (2018.01); *G16H 40/63* (2018.01); *G16H 40/67* (2018.01); *G16H 50/30* (2018.01); *H04N 9/3179* (2013.01); *H04N 9/3182* (2013.01); *H04N 9/3194* (2013.01); *A61B 5/08* (2013.01); *A61B 2560/0242* (2013.01)

(56) References Cited

U.S. PATENT DOCUMENTS

| | | | |
|---|---|---|---|
| 8,170,609 B2 | 5/2012 | Hedtke et al. | |
| 9,380,978 B2 | 7/2016 | Reiner | |
| 2001/0029535 A1 | 10/2001 | Hirano et al. | |
| 2001/0049471 A1 | 12/2001 | Suzuki et al. | |
| 2002/0024640 A1 | 2/2002 | Ioka | |
| 2002/0063855 A1 | 5/2002 | Williams | |
| 2002/0123908 A1 | 9/2002 | Ando et al. | |
| 2003/0003988 A1 | 1/2003 | Walker | |
| 2003/0013981 A1 | 1/2003 | Gevins et al. | |
| 2003/0037124 A1 | 2/2003 | Yamaura et al. | |
| 2004/0039254 A1 | 2/2004 | Stivoric | |
| 2005/0061315 A1 | 3/2005 | Lee et al. | |
| 2005/0090372 A1 | 4/2005 | Burrows | |
| 2005/0258943 A1 | 11/2005 | Mian | |
| 2005/0264425 A1 | 12/2005 | Sato | |
| 2006/0071798 A1 | 4/2006 | Kiff | |
| 2007/0016443 A1 | 1/2007 | Wachman | |
| 2007/0100595 A1 | 5/2007 | Earles et al. | |
| 2007/0156060 A1 | 7/2007 | Cervantes | |
| 2007/0287501 A1 | 12/2007 | Hoshina | |
| 2008/0068158 A1 | 3/2008 | Sumiyoshi | |
| 2008/0146866 A1 | 6/2008 | Arai et al. | |
| 2008/0162352 A1 | 7/2008 | Gizewski | |
| 2008/0311968 A1 | 12/2008 | Hunter | |
| 2008/0319855 A1 | 12/2008 | Stivoric | |
| 2009/0177327 A1 | 7/2009 | Turner et al. | |
| 2009/0247834 A1 | 10/2009 | Schechter | |
| 2010/0112955 A1 | 5/2010 | Krishnaswamy et al. | |
| 2010/0216509 A1 | 8/2010 | Riemer et al. | |
| 2010/0268551 A1 | 10/2010 | McNames | |
| 2011/0015495 A1 | 1/2011 | Dothie et al. | |
| 2011/0119080 A1 | 5/2011 | Hayter et al. | |
| 2011/0137818 A1 | 6/2011 | Goad et al. | |
| 2011/0166875 A1 | 7/2011 | Hayter et al. | |
| 2011/0191158 A1 | 8/2011 | Kateraas et al. | |
| 2011/0267196 A1 | 11/2011 | Hu | |
| 2012/0083705 A1 | 4/2012 | Yuen et al. | |
| 2012/0101889 A1 | 4/2012 | Kurata et al. | |
| 2012/0157209 A1 | 6/2012 | Yamashita | |
| 2012/0164946 A1 | 6/2012 | Fujiwara et al. | |
| 2012/0215328 A1 | 8/2012 | Schmelzer | |
| 2012/0253220 A1* | 10/2012 | Rai | A61B 5/4806 600/544 |
| 2012/0265546 A1 | 10/2012 | Hwang et al. | |
| 2012/0313791 A1 | 12/2012 | Mehta | |
| 2012/0330556 A1 | 12/2012 | Shaanan et al. | |
| 2013/0012234 A1 | 1/2013 | Tufty | |
| 2013/0095459 A1 | 4/2013 | Tran | |
| 2013/0103416 A1 | 4/2013 | Amigo et al. | |
| 2013/0138450 A1 | 5/2013 | Vigneux | |
| 2013/0141235 A1 | 6/2013 | Utter | |
| 2013/0245465 A1 | 9/2013 | Kasama | |
| 2013/0280985 A1 | 10/2013 | Klein | |
| 2014/0111690 A1* | 4/2014 | Kim | G06F 3/017 348/565 |
| 2014/0121540 A1 | 5/2014 | Raskin | |
| 2014/0173586 A1 | 6/2014 | Dugan | |
| 2014/0198949 A1 | 7/2014 | Garlington | |
| 2014/0222101 A1* | 8/2014 | Miesel | A61N 1/36064 607/45 |
| 2014/0247146 A1 | 9/2014 | Proud | |
| 2014/0269224 A1 | 9/2014 | Huh | |
| 2014/0274406 A1 | 9/2014 | Walkingstick | |
| 2014/0276245 A1 | 9/2014 | Tsutsumi | |
| 2014/0316191 A1 | 10/2014 | De Zambotti | |
| 2014/0347366 A1 | 11/2014 | Emori et al. | |
| 2014/0372133 A1 | 12/2014 | Austrum et al. | |
| 2014/0379374 A1 | 12/2014 | Vinals | |
| 2015/0018023 A1 | 1/2015 | Tomii et al. | |
| 2015/0094544 A1 | 4/2015 | Spolin | |
| 2015/0128353 A1 | 5/2015 | Kildey | |
| 2015/0258301 A1 | 9/2015 | Trivedi et al. | |
| 2016/0015315 A1 | 1/2016 | Auphan et al. | |
| 2016/0151603 A1 | 6/2016 | Shouldice | |
| 2016/0270718 A1 | 9/2016 | Heneghan et al. | |

FOREIGN PATENT DOCUMENTS

| | | |
|---|---|---|
| JP | 10-48363 | 2/1998 |
| JP | H 11-070097 | 3/1999 |
| JP | 2001-273376 | 10/2001 |
| JP | 2001-344352 | 12/2001 |
| JP | 2002-034955 | 2/2002 |
| JP | 2002-41930 | 2/2002 |
| JP | 2002-072359 | 3/2002 |
| JP | 2002-149830 | 5/2002 |
| JP | 2002-222264 | 8/2002 |
| JP | 2002-245178 | 8/2002 |
| JP | 2002-315738 | 10/2002 |
| JP | 2003-015665 | 1/2003 |
| JP | 2003-264812 | 9/2003 |
| JP | 2003-299624 | 10/2003 |
| JP | 2003-319910 | 11/2003 |
| JP | 2004-157596 | 6/2004 |
| JP | 2004-530195 | 9/2004 |
| JP | 2005-050253 | 2/2005 |
| JP | 2005-074107 | 3/2005 |
| JP | 2005-237569 | 9/2005 |
| JP | 2005-247719 | 9/2005 |
| JP | 2006-263002 | 10/2006 |
| JP | 2007-004000 A | 1/2007 |
| JP | 2007-054596 | 3/2007 |
| JP | 2007-080219 | 3/2007 |
| JP | 2007-117365 | 5/2007 |

(56) References Cited

FOREIGN PATENT DOCUMENTS

| | | |
|---|---|---|
| JP | 2007-512086 | 5/2007 |
| JP | 2007-222276 | 9/2007 |
| JP | 2007-248052 | 9/2007 |
| JP | 2007-319238 | 12/2007 |
| JP | 2008-176741 | 7/2008 |
| JP | 2008-212391 | 9/2008 |
| JP | 2009-078070 | 4/2009 |
| JP | 2009-176130 | 8/2009 |
| JP | 2009-251452 | 10/2009 |
| JP | 2010-099173 | 5/2010 |
| JP | 2010-170534 | 8/2010 |
| JP | 2010-201113 | 9/2010 |
| JP | 2011-36649 | 2/2011 |
| JP | 2011-160327 | 8/2011 |
| JP | 2011-243041 | 12/2011 |
| JP | 2012-503804 | 2/2012 |
| JP | 2012-134737 | 7/2012 |
| JP | 2012-139362 | 7/2012 |
| JP | 2012-147879 | 8/2012 |
| JP | 2013-511780 | 4/2013 |
| JP | WO 2013065504 | 5/2013 |
| JP | 2013-117941 | 6/2013 |
| JP | 2013-146463 | 8/2013 |
| JP | 2013-168026 | 8/2013 |
| JP | 2013-182422 | 9/2013 |
| JP | 2013-192620 | 9/2013 |
| JP | 2013-537435 | 10/2013 |
| JP | 2013-257837 | 12/2013 |
| JP | 2014-052834 | 3/2014 |
| WO | WO 02/073864 A2 | 9/2002 |
| WO | WO 2005/055802 | 6/2005 |
| WO | WO 2005/094667 A2 | 10/2005 |
| WO | WO 2007/023818 | 3/2007 |
| WO | WO 2008/096307 A1 | 8/2008 |
| WO | WO 2010/036700 | 4/2010 |
| WO | WO 2011/136253 | 11/2011 |
| WO | WO 2011/150362 A2 | 12/2011 |
| WO | WO 2011/156272 | 12/2011 |
| WO | WO 2012/006549 A2 | 1/2012 |
| WO | WO 2013/065246 A2 | 5/2013 |
| WO | WO 2013/080109 | 6/2013 |

OTHER PUBLICATIONS

U.S. Appl. No. 15/421,708, filed Feb. 1, 2017, Information Processing System, Information Processing Device, Storage Medium Storing Information Processing Program and Information Processing Method.
Office Action dated Sep. 25, 2019 issued in corresponding U.S. Appl. No. 15/421,724.
Office Action dated Oct. 21, 2019 in corresponding U.S. Appl. No. 15/211,387.
Office Action issued in U.S. Appl. No. 15/211,300 dated Dec. 20, 2019.
Office Action in related Application No. 15/211,265 dated Mar. 18, 2020.
Notice of Reasons for Refusal dated Feb. 3, 2020 in corresponding Japanese Patent Application No. 2018-196896.
Notice of Refusal dated Feb. 6, 2020 in corresponding Japanese Patent Application No. 2018-221951 with English Machine translation.
Ouchi et al., "Healthcare Services Using a Wearable Device", IPSJ SIG Technical Reports, Japan Information Processing Society of Japan, Feb. 23, 2007, vol. 2007, No. 14, pp. 29-36.
Office Action in corresponding U.S. Appl. No. 15/211,146 dated Feb. 7, 2020.
Notice of Reasons for Refusal in corresponding Japanese Patent Appln. No. 2019-007669 dated Oct. 29, 2019.
M. Sato et al., "Wireless Sensor Systems" 1st Edition, Tokyo Denki University Press, Oct. 30, 2012, pp. 186 and 196.
Kawai et al., U.S. Appl. No. 15/211,146, filed Jul. 15, 2016 (130 pages).
Kawai et al., U.S. Appl. No. 15/211,122, filed Jul. 15, 2016 (149 pages).
Kawai et al., U.S. Appl. No. 15/211,182, filed Jul. 15, 2016 (214 pages).
Kawai et al., U.S. Appl. No. 15/211,265, filed Jul. 15, 2016 (219 pages).
Kawai et al., U.S. Appl. No. 15/211,300, filed Jul. 15, 2016 (209 pages).
Kawai et al., U.S. Appl. No. 15/211,387, filed Jul. 15, 2016 (218 pages).
English translation of International Preliminary Report on Patentability issued in PCT/JP2014/078824 dated Jul. 19, 2016 (14 pages).
English translation of International Preliminary Report on Patentability issued in PCT/JP2014/078825 dated Jul. 19, 2016 (14 pages).
Hattori., U.S. Appl. No. 15/421,724, filed Feb. 1, 2017 (183 pages).
Hattori., U.S. Appl. No. 15/421,708, filed Feb. 1, 2017 (132 pages).
European Search Report issued in corresponding Europe Patent Appln No. 14 87 8426.7 dated Aug. 7, 2017.
Supplemental European Search Report issued in corresponding European Patent Appln No. 14 87 8891 dated Sep. 12, 2017.
Guan, "All-in Pedometer iPhone app review App Safari", Jan. 25, 2011, URL:http://ww.appsafari.com/utilities/15183/all-in-pedometer/ retrieved on Sep. 4, 2017.
Partial Supplemental European Search Report issued in corresponding European Patent Appln No. 14878971.2 dated Sep. 5, 2017 (7 pgs.).
European Search Report in corresponding European Patent Appln. No. 15830638.1 dated Mar. 9, 2018.
Office Action dated Aug. 16, 2018 issued in corresponding Japanese Appln. No. 2015-557699 (8 pages).
Office Action dated Aug. 27, 2018 issued in U.S. Appl. No. 15/211,300 (28 pgs.).
Office Action dated Aug. 31, 2018 issued in U.S. Appl. No. 15/211,265 (36 pages).
Office Action dated Oct. 4, 2018 issued in U.S. Appl. No. 15/211,387 (37 pages).
Notice of Reasons for Refusal in corresponding Japanese Application No. JP2015-557716 dated Oct. 24, 2018.
Notice of Reasons for Refusal dated Nov. 5, 2018 issued in Japanese Patent Application No. 2015-557713 (4 pgs.).
Office Action dated Nov. 29, 2018 issued in U.S. Appl. No. 15/211,122.
Office Action issued in U.S. Appl. No. 15/211,300 dated Jan. 25, 2019.
Office Action issued in U.S. Appl. No. 15/211,182 dated Feb. 1, 2019.
Office Action issued in U.S. Appl. No. 15/421,708 dated Feb. 4, 2019.
Office Action issued in Japanese Patent Appln. No. 2015-557714 dated Mar. 13, 2019.
Decision of Refusal dated Mar. 19, 2019 issued in corresponding Japanese Patent Application No. 2015-557713.
Decision of Dismissal of Amendment dated Mar. 19, 2019 issued in corresponding Japanese Patent Application No. 2015-557713.
Office Action in U.S. Appl. No. 15/421,724 dated Apr. 12, 2019.
Examiner-Initiated Interview Summary for the interview held on May 14, 2019 issued in U.S. Appln. No. 15/211,300.
Purewal, "Review: Runtastic's mobile apps make tracking a workout easier PCWorld", Nov. 29, 2012, XP055598914, Retrieved from the internet: https://pcworld.com/article/2017159/review-runtastics-mobile-apps-make-tracking-a-workout-easier.html, retrieved on Jun. 24, 2019.
Communication received in corresponding European Patent Application No. 14878891.2 dated Jun. 24, 2019 (5 pages).
Office Action dated Aug. 23, 2019 in corresponding U.S. Appl. No. 15/211,146.
U.S. Appl. No. 15/211,122, filed Jul. 15, 2016, Information Processing System, Information Processing Server, Information Processing Program, and Fatigue Evaluation Method.
U.S. Appl. No. 15/211,146, filed Jul. 15, 2016, Information Processing System, Information Processing Server, Information Processing Program, and Information Providing Method.

(56) References Cited

OTHER PUBLICATIONS

U.S. Appl. No. 15/211,182, filed Jul. 15, 2016, Information Processing System, Server System, Information Processing Apparatus, and Information Processing Method.
U.S. Appl. No. 15/211,265, filed Jul. 15, 2016, Information Processing System, Server System, Information Processing Program, and Information Processing Method.
U.S. Appl. No. 15/211,300, filed Jul. 15, 2016, Information Processing System, Server System, and Information Processing Program.
U.S. Appl. No. 15/211,387, filed Jul. 15, 2016, Information Processing System and Information Processing Apparatus.
U.S. Appl. No. 15/421,724, filed Feb. 1, 2017, Information Processing System, Information Processing Server, Storage Medium Storing Information Processing Program and Information Provision Method.
U.S. Appl. No. 16/567,811, filed Sep. 11, 2019, Display System and Display Device.
U.S. Appl. No. 16/570,951, filed Sep. 13, 2019, Information Processing System, Information Processing Device, Storage Medium Storing Information Processing Program, and Information Processing Method.
Office Action in U.S. Appl. No. 15/211,300 dated Apr. 9, 2020.
Office Action in U.S. Appl. No. 15/211,122 dated Apr. 30, 2020.
Notice of Allowance received in U.S. Appl. No. 15/211,182 dated Jun. 23, 2020.
Office Action received in related U.S. Appl. No. 15/211,146 dated Nov. 2, 2020.
Office Action received in U.S. Appl. No. 15/211,122 dated Feb. 17, 2021.
Notice of Reasons for Refusal in Japanese Patent Appln. No. JP2019-172746 dated Sep. 28, 2020.

\* cited by examiner

Fig. 13

|     | ACTIVITY CONTENT | ACTIVITY LEVEL (ACTIVE HOURS) |
|-----|------------------|-------------------------------|
| (a) | MOVEMENT (WALKING) | 15 MINUTES |
| (b) | WORK | 8 HOURS |
| (c) | MOVEMENT (WALKING) | 10 MINUTES |
| (d) | MOVEMENT (WALKING) | 10 MINUTES |

Fig. 15

|  | ACTIVITY CONTENT | ENVIRONMENTAL VALUE |
|---|---|---|
| (a) | MOVEMENT (WALKING) | AMBIENT TEMPERATURE: 32° C, HUMIDITY: 60 |
| (b) | WORK | AMBIENT TEMPERATURE: 26° C, HUMIDITY: 50% |
| (c) | MOVEMENT (WALKING) | AMBIENT TEMPERATURE: 30° C, HUMIDITY: 65% |
| (d) | MOVEMENT (WALKING) | AMBIENT TEMPERATURE: 28° C, HUMIDITY: 60% |

Fig. 22

| CONDITION OF ACTIVITY INFORMATION || CHANGE LEVEL OF FATIGUE LEVEL |
|---|---|---|
| ACTIVITY CONTENT | ACTIVITY LEVEL (ACTIVE HOURS) | |
| WORK | 8 TO 10 HOURS | FATIGUE LEVEL: +10 |
| WORK | 10 HOURS OR MORE | FATIGUE LEVEL: +30 |
| ... | ... | ... |
| MOVEMENT (WALKING) | LESS THAN 15 MINUTES | FATIGUE LEVEL: +5 |
| MOVEMENT (WALKING) | NOT LESS THAN 15 MINUTES BUT LESS THAN 30 MINUTES | FATIGUE LEVEL: +20 |
| ... | ... | ... |
| MASSAGE | — | FATIGUE LEVEL: −20 |
| | ... | ... |

Fig. 23

| CONDITION OF ENVIRONMENTAL INFORMATION || CHANGE LEVEL OF ENVIRONMENTAL INDEX |
|---|---|---|
| ACTIVITY CONTENT | ENVIRONMENTAL VALUE | |
| MOVEMENT (WALKING) | AMBIENT TEMPERATURE: NOT LOWER THAN 30° C BUT LOWER THAN 33° C<br>HUMIDITY: NOT LOWER THAN 60% BUT LOWER THAN 70% | −15 |
| MOVEMENT (WALKING) | AMBIENT TEMPERATURE: NOT LOWER THAN 33° C<br>HUMIDITY: NOT LOWER THAN 60% BUT LOWER THAN 70% | −30 |
| ⋮ | ⋮ | ⋮ |
| WORK | AMBIENT TEMPERATURE: LOWER THAN 28° C<br>HUMIDITY: LOWER THAN 60% | +10 |
| WORK | AMBIENT TEMPERATURE: NOT LOWER THAN 28° C BUT LOWER THAN 33° C<br>HUMIDITY: NOT LOWER THAN 60% BUT LOWER THAN 70% | −10 |
| ⋮ | ⋮ | ⋮ |

Fig. 24

| | CONDITION OF EVALUATION RESULT | | | | | SERVICE CONTENT | | |
|---|---|---|---|---|---|---|---|---|
| | HEALTH INDEX | ENVIRONMENTAL INDEX | EMOTION INDEX | QOL INDEX | PREFERENCE INFORMATION | ADVICE | RECOMMENDATION | PRIVILEGE |
| (a) | — | — | — | 30 OR LOWER | — | ADVICE A | COMMODITY A | — |
| (b) | 30 OR LOWER | — | 30 OR LOWER | — | — | ADVICE B | COMMODITY B | — |
| (c) | — | 40 OR LOWER | 50 OR LOWER | 40 OR LOWER | — | ADVICE C | — | GIVE CONTENT |
| (d) | 30 OR LOWER | 30 OR LOWER | — | — | PHYSICAL EXERCISE | ADVICE D | COMMODITY C | — |
| (e) | 30 OR LOWER | 30 OR LOWER | — | — | MEAL | ADVICE E | COMMODITY D | — |
| (f) | 70 OR HIGHER | — | — | — | — | — | — | ADD POINTS |
| ... | ... | ... | ... | ... | ... | ... | ... | ... |

DISPLAY SYSTEM AND DISPLAY DEVICE

CROSS REFERENCE TO RELATED APPLICATION

This application is a continuation of U.S. application Ser. No. 15/211,497 filed Jul. 15, 2016, which is a continuation of International Application No. PCT/JP2014/078827, filed on Oct. 29, 2014, which designated the U.S. and claims priority to International Application No. PCT/JP2014/050851 filed Jan. 17, 2014, and International Application No. PCT/JP2014/070931 filed Aug. 7, 2014, the entire contents of each of which are hereby incorporated herein by reference.

FIELD

The technique shown here relates to display systems and display devices used when a user is in bed.

BACKGROUND AND SUMMARY

Conventionally, systems for monitoring sleep stages of users have existed. For example, such system gives a stimulus to a user in accordance with his/her sleep stage to bring the user to another sleep stage.

In the system used when a user is in bed, it is desired to use display means that is easy to view by the user in bed.

Therefore, the present application discloses a display system and a display device, each of which is capable of providing a display that is easy to view by a user in bed.

(1) One example of a display system disclosed in the present specification includes a sensor, a projector, and control means. The sensor senses user information for calculating a sleep state of a user. The projector projects and displays a predetermined image. The control means causes the projector to project and display an image related to the sleep state calculated on the basis of the user information.

(2) Another example of the display system disclosed in the present specification includes a sensor, a projector, timing specifying means, and control means. The sensor senses user information for calculating a sleep state of a user. The projector projects and displays a predetermined image. The timing specifying means specifies a timing regarding awakening of the user on the basis of the user information. The control means causes the projector to start projection and display of the image in accordance with the specified timing.

(3) Another example of the display system disclosed in the present specification includes a sensor, a projector, control means, and communication means. The sensor senses user information for calculating a sleep state of a user in bed. The projector projects and displays a predetermined image when the user is in bed. The control means controls the projector. The communication means performs communication with a server through a network.

(4) The control means may cause the projector to display the image related to the sleep state calculated on the basis of the user information, at a timing in accordance with the sleep state of the user, which is a timing specified on the basis of the user information.

(5) The control means may cause the projector to display the image related to the sleep state at a timing before the user awakens or a timing when the user awakens, which is a timing specified on the basis of the user information.

(6) The control means may control power supply to the projector in accordance with the sleep state of the user.

(7) The control means may start power supply to the projector in accordance with a timing regarding awakening of the user, which is a timing specified on the basis of the user information.

(8) The control means may change an image for inducing sleep onset of the user and/or an image for inducing awakening of the user, in accordance with the sleep state of the user, and may cause the projector to project and display the image.

(9) The display system may further include judgment means for judging, when the user awakens, whether or not the awakening is an awakening in mid-course of sleep. In this case, the control means may cause the projector to project and display different images in a case where the awakening of the user is judged to be an awakening in mid-course of sleep and in a case where the awakening of the user is judged not to be an awakening in mid-course of sleep, respectively.

(10) The display system may further include evaluation means for performing an evaluation of sleep of the user on the basis of the user information. In this case, the control means may cause the projector to project and display a result of the evaluation at a timing in accordance with the sleep state of the user, which is a timing specified on the basis of the user information.

(11)
The display system may further include a light source which irradiates the user with light. In this case, the control means may start irradiation of the light source at a timing before the user awakens, which is a timing specified on the basis of the user information.

(12)
The control means may successively acquire the user information from the sensor, and may control the projector in real time in accordance with the acquired user information.

(13)
The communication means may receive, from the server, service data for providing the user with a network service in accordance with an evaluation regarding health of the user.

(14)
The projector may project and display an image based on the service data.

(15)
The communication means may transmit, to the server, the user information sensed by the sensor and/or information calculated from the user information.

(16)
The communication means may receive an image content from the server. In this case, the projector may project and display the image content.

(17)
The projector may project and display the image on a ceiling above the projector itself.

(18)
The sensor may sense biological information of the user in a state of not being in contact with the user.

(19)
The sensor may sense the biological information from the user who is away from the display device within a predetermined range.

(20)
The sensor may emit radio waves or sound waves toward a subject to be sensed and receive reflected waves, and may output the biological information on the basis of a result of the reception.

(21)

The display system may further include a camera and correction means. The camera captures a projection spot of the projector. The correction means performs, on the image projected and displayed by the projector, a correction that takes into consideration unevenness of the projection spot, on the basis of an image of the projection spot captured by the camera.

(22)

The correction means may perform, on the image projected and displayed by the projector, a correction that takes into consideration color of the projection spot, on the basis of the image of the projection spot.

(23)

The display system may further include a loudspeaker provided in the same casing as that for the sensor and the projector.

The present specification discloses a display device including some of the respective means of (1) to (23) described above. Further, the present specification discloses a non-transitory computer-readable storage medium having stored therein an information processing program which causes a computer of the display system or the display device described above to function as some of the respective means of (1) to (23) described above. Furthermore, the present specification discloses an information processing method (display method) executed in the display system or the display device described above.

According to the display system and the display device described above, the state of a user of a hand-held terminal can be evaluated.

These and other objects, features, aspects and advantages will become more apparent from the following detailed description when taken in conjunction with the accompanying drawings.

BRIEF DESCRIPTION OF THE DRAWINGS

FIG. 13 shows one example of activity information calculated in the present embodiment;

FIG. 15 shows one example of environmental information calculated in the present embodiment;

FIG. 22 shows one example of a table used for calculating a second fatigue level;

FIG. 23 shows one example of a table used for calculating an environmental index;

FIG. 24 shows one example of a table used for determining a network service in accordance with an evaluation result;

DETAILED DESCRIPTION OF NON-LIMITING EXAMPLE EMBODIMENTS

1. Configuration of Information Processing System

Figure 1:
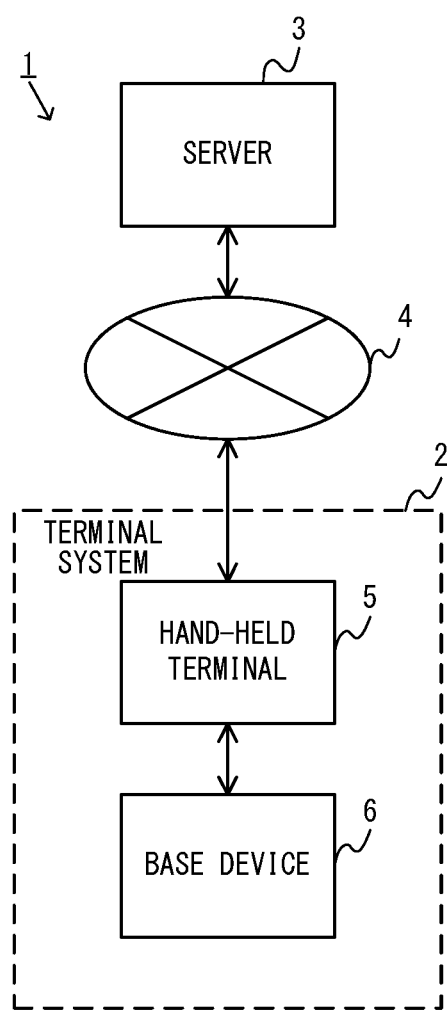
FIG. 1 is a block diagram showing a non-limiting example of the configuration of an information processing system according to the present embodiment.

In the following, with reference to the drawings, an information processing system, an information processing server, a storage medium having stored therein an information processing program, and an information processing method according to the present embodiment will be described. First, The overall configuration of the information processing system according to the present embodiment will be described. FIG. 1 is a block diagram showing one example of the configuration of an information processing system according to the present embodiment. As shown in FIG. 1, an information processing system 1 includes a terminal system 2 and a server 3. The terminal system 2 and the server 3 can communicate with each other through a network 4 such as the Internet and a mobile communication network. It should be noted that although only a single terminal system 2 is shown in FIG. 1, the information processing system 1 in the present embodiment includes multiple terminal systems each provided to a user.

The terminal system 2 calculates various types of information (health information, activity information, environmental information, emotion information, and preference information described later) related to the user, and uploads the information to the server 3. In the present embodiment, various types of information are calculated (generated) at an appropriate timing throughout a single day (i.e., while the user is asleep and awake). Although details will be described later, while the user is asleep, the terminal system 2 calculates, for example, as health information related to the health and/or the body of the user, information related to sleep and fatigue. In addition, while the user is awake, the terminal system 2 calculates, for example, the activity information related to the activity of the user, the environmental information related to the environment surrounding the user, emotion information related to emotion of the user, and preference information related to hobbies and preference (hobby, liking, interests, life style, etc.) of the user.

The server 3 performs an evaluation regarding the quality of life (QOL) of the user on the basis of the information uploaded from the terminal system 2. Although details will be described later, the terminal system 2 in the present embodiment performs an evaluation of health (including fatigue and sleep), environment, and emotion of the user, and further performs an evaluation regarding QOL as an overall evaluation. Furthermore, the server 3 provides the user with a network service in accordance with these evaluation results. In the present embodiment, the server 3 presents the user with the evaluation results, provides the user with advice information, recommendation information (e.g., information introducing a commodity), or content (e.g., music) in accordance with the evaluation results, or gives the user a privilege in accordance with the evaluation results.

The above described various types of information used for evaluating QOL of the user or used for the network service in accordance with the evaluations are sometimes referred to as "QOL factor information", herein. More specifically, in the present embodiment, the health information, the activity information, the environmental information, the emotion information, and the preference information are calculated as the QOL factor information.

Figure 2:
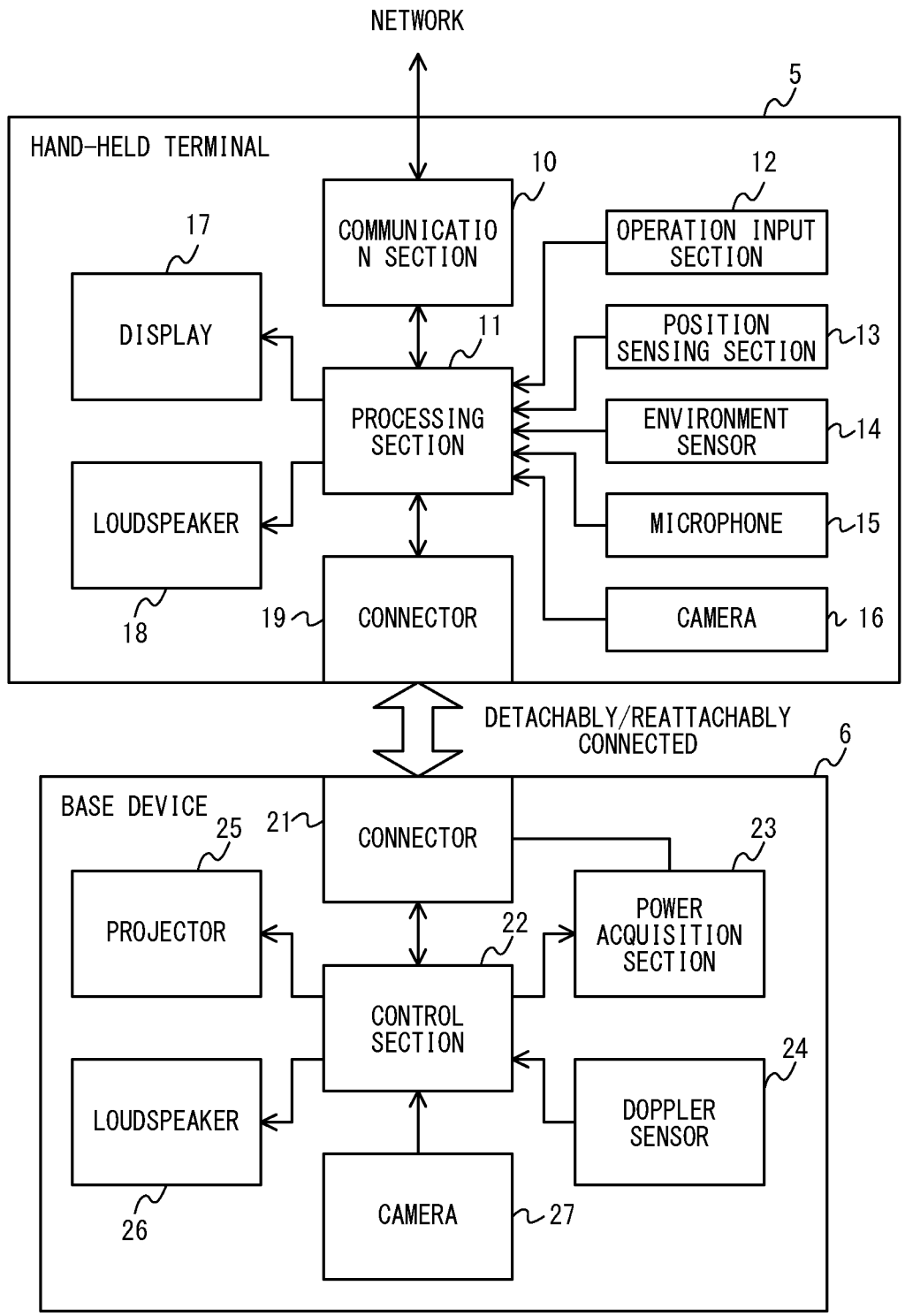
FIG. 2 shows a non-limiting example of the detailed configuration of a terminal system 2.
Figure 3:
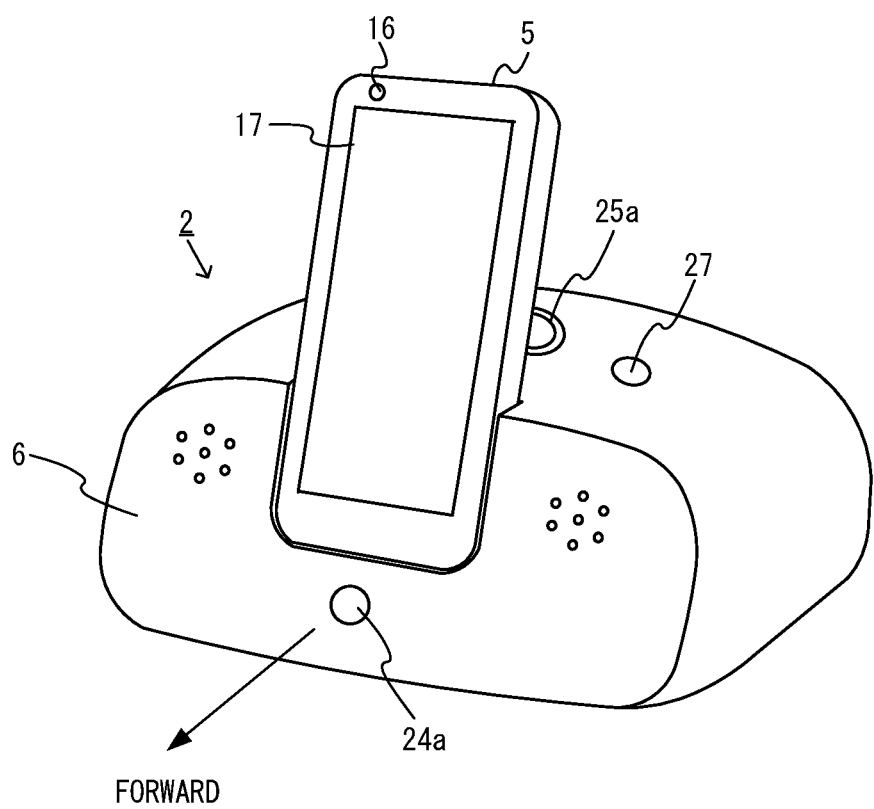
FIG. 3 shows a non-limiting example of the exterior view of the terminal system 2.

In the following, one example of the configuration of the terminal system 2 will be described. FIG. 2 shows one example of the detailed configuration of the terminal system 2. FIG. 3 shows one example of the exterior view of the terminal system 2. As shown in FIGS. 1 to 3, the terminal system 2 includes a hand-held terminal 5 and a base device 6. The hand-held terminal 5 is carried by the user. The base device 6 is placed at, for example, the home of the user.

In the present embodiment, the hand-held terminal 5 is a hand-held type information processing apparatus, and the base device 6 is a cradle that is connectable to the hand-held terminal 5. As shown in FIG. 3, the hand-held terminal 5 can connect to the base device 6 in a detachable/reattachable manner. Although details will be described later, communication between the hand-held terminal 5 and the base device 6 becomes possible when the hand-held terminal 5 and the base device 6 are connected. In addition, the base device 6 has a function of performing charging with regard to the hand-held terminal 5, and, when the hand-held terminal 5 and the base device 6 are connected, charging of the hand-held terminal 5 by the base device 6 becomes possible.

In another embodiment, a configuration in which the hand-held terminal 5 and the base device 6 are detachably/reattachably connected via a cable may be used. In still another embodiment, the communication between the hand-held terminal 5 and the base device 6 may be performed through wireless communication such as radio wave communication and infrared communication.

First, the configuration of the hand-held terminal 5 in the present embodiment will be described. The hand-held terminal 5 is a hand-held type information processing apparatus, and, in the present embodiment, is a multifunctional device such as, for example, a mobile phone, a smart phone, or a tablet terminal. Thus, the hand-held terminal 5 has some of the various types of functions (input function, output (display) function, information processing function, network communication function, telephone call function, camera function, etc.) included in a general multifunctional device. The network communication function is a communication function realized through the Internet and/or a communication function realized through a mobile communication network. The hand-held terminal 5 may be attained by installing predetermined functions on an off-the-shelf multifunctional device. In the present embodiment, the hand-held terminal 5 is used for, in addition to be used as the multifunctional device described above, calculating the QOL factor information and transmitting the QOL factor information to the server 3. Furthermore, the hand-held terminal 5 may be an information processing apparatus that can be worn by the user such as, for example, a wrist watch-type or goggle-type terminal (i.e., wearable terminal).

As shown in FIG. 2, the hand-held terminal 5 includes a communication section 10. The communication section 10 connects to the network 4 to perform communication with the server 3. In the present embodiment, the communication section 10 is a communication module having the function of connecting to a mobile communication network (mobile phone communication network) to perform communication. For example, the communication section performs communication with a communication method in compliance with telecommunications standards of 3G or telecommunications standards of 4G (including LTE (Long Term Evolution)). It should be noted that the method with which the hand-held terminal 5 communicates with the server 3 may be a method with which a communication module with Wi-Fi authentication performs communication through a wireless LAN. In addition, the hand-held terminal 5 may have a function of communicating with the server 3 through the mobile communication network and a function of performing communication with the server 3 through the wireless LAN.

The hand-held terminal 5 includes a processing section 11. The processing section 11 executes various types of information processing to be executed by the hand-held terminal 5. The processing section 11 is connected to each section of 10, and 12 to 19 of the hand-held terminal 5. The processing section 11 has a CPU (Central Processing Unit) and a memory. In the hand-held terminal 5, the various types of information processing described above are executed as a result of the CPU using the memory and executing an information processing program stored in the hand-held terminal 5. In the present embodiment, the processing section 11 executes, as the information processing, a process for calculating the QOL factor information described above, and a process for presenting the user with the information (e.g., information related to the network service) received from the server 3, etc. When the hand-held terminal 5 operates as a multifunctional device, the processing section 11 executes information processing for achieving various functions.

The hand-held terminal 5 includes an input/output interface, and functions as an information processing apparatus (input/output terminal) for allowing the user to input and browse information. Specifically, the hand-held terminal 5 includes an operation input section 12, a display 17, and a loudspeaker 18. The operation input section 12 is an input device of any type for accepting an operation input by the user. In the present embodiment, the operation input section 12 includes buttons and a touch panel formed on the display 17. In another embodiment, the hand-held terminal 5 may include, as the operation input section 12, a sensor (acceleration sensor, gyro sensor) for sensing an attitude of the hand-held terminal 5.

The display 17, which is one example of the output device, displays various types of images generated on the hand-held terminal 5 in response to an input with respect to the operation input section 12, and displays various types of images (images related to the network service) based on data received from the server 3. The loudspeaker 18, which is one example of the output device, outputs various types of sounds generated by the hand-held terminal 5 in response to an input with respect to the operation input section 12, and outputs various types of sounds (music and audio related to the network service) based on the data received from the server 3.

The hand-held terminal 5 includes a sensor for sensing (acquiring) information for calculating the QOL factor information. In the present embodiment, the hand-held terminal 5 includes a position sensing section 13, an environment sensor 14, a microphone 15, and a camera 16.

The position sensing section 13 senses the position of the hand-held terminal 5. In the present embodiment, the position sensing section 13 senses the position by using the GNSS (Global Navigation Satellite System). The position sensing section 13 is, for example, a GPS (Global Positioning System) sensor (GPS module). It should be noted that the position sensing method by the position sensing section 13 may be any method, and the position sensing section 13 may sense the position by using, for example, a beacon. Furthermore, for example, the position sensing section 13 may calculate information (e.g., information indicating at which floor of the building one is located) indicating the altitude of the user by calculating the change in altitude based on a sensing result from an air pressure sensor.

The environment sensor 14 senses the environment surrounding the hand-held terminal 5. In the present embodiment, the environment sensor 14 includes a temperature sensor and a humidity sensor. In another embodiment, an air pressure sensor, an illumination sensor, a noise sensor, an odor sensor, or the like may be included in the environment sensor 14. More specifically, the environment sensor 14 may be one that senses at least one of temperature, humidity, illumination intensity, atmospheric pressure, sound, and odor. Furthermore, in another embodiment, the microphone 15 may be used as a sensor for sensing noise in the surrounding area.

The microphone 15 senses sound in the surrounding area of the hand-held terminal 5. Although details will be described later, the microphone 15 in the present embodiment is used for calculating the emotion information. The microphone 15 may be used for accepting an audio input with respect to the hand-held terminal 5.

The camera 16 is used for capturing an image of the user, and calculating the emotion information by using the captured image (details are described later). In the present embodiment, the camera 16 is disposed on the same side (inner side) where the display 17 is disposed on the hand-held terminal 5 (see FIG. 3). Thus, the camera 16 is disposed at a position enabling capturing an image of the user who is operating the hand-held terminal 5.

The hand-held terminal 5 includes a connector 19 for forming an electrical connection with the base device 6. In the present embodiment, when the hand-held terminal 5 is mounted on the base device 6 (see FIG. 3), the connector 19 makes contact with a connector 21 of the base device 6. With this, communication between the hand-held terminal 5 and the base device 6 becomes possible.

It should be noted that the hand-held terminal 5 includes a battery that is not diagrammatically represented, and each section of the hand-held terminal 5 operates by the power supplied from the battery. Although details will be described later, in the present embodiment, the battery of the hand-held terminal 5 can be charged by the base device 6.

Next, the configuration of the base device 6 in the present embodiment will be described. In the present embodiment, the base device 6 is disposed, for example, at the bedroom of the user (see FIG. 5), and is used for sensing biological information related to sleep of the user while the user is in bed. Here, the biological information is information sensed from the body of the user. In the present embodiment, respiration, pulse, and body movement are acquired as the biological information. In addition, the base device 6 is used for presenting the user in bed with content (e.g., content encouraging sleep onset of the user) and information (information of evaluation results related to sleep).

The base device 6 includes a support section for detachably/reattachably supporting the hand-held terminal 5. Specifically, as shown in FIG. 3, a recessed portion in accordance with the shape of one portion of the hand-held terminal 5 is formed on a casing (support section) of the base device 6. When the hand-held terminal 5 is inserted in this recessed portion, the hand-held terminal 5 becomes mounted on the base device 6.

As shown in FIG. 2, the base device 6 includes the connector 21. When the hand-held terminal 5 is inserted in the recessed portion, the connector 19 of the hand-held terminal 5 and the connector 21 of the base device 6 are connected. As a result, communication between the hand-held terminal 5 and the base device 6 becomes possible, and charging of the hand-held terminal 5 by the base device 6 becomes possible.

The base device 6 includes a Doppler sensor 24 which is one example of the sensor for sensing the biological information. The Doppler sensor 24, by discharging microwaves and receiving reflected waves of the discharged microwaves, senses a moving object based on a difference between the frequency of the discharged microwaves and the frequency of the received microwaves. In the present embodiment, (an emission section 24a of) the Doppler sensor 24 emits radio waves in the forward direction of the base device 6 (see FIG. 3). In the present embodiment, the subject to be sensed by the Doppler sensor 24 is the user, and body movement of the user is sensed by the Doppler sensor 24. Although details will be described later, analysis such as frequency analysis performed on the sensed biological information (output waveforms of the Doppler sensor 24) allows further calculation of biological information other than body movement such as respiration and pulse.

The base device 6 includes a power acquisition section 23 for acquiring power from an external power supply. In the present embodiment, the base device 6 is (may be detachably/reattachably) connected to a power plug and an AC adapter via a power cord that is not diagrammatically represented. When the power plug is connected to an electrical outlet which is an external power supply, power is supplied to the power acquisition section 23 of the base device 6. The base device 6 operates by the power from the external power supply acquired by the power acquisition section 23. In addition, the power acquisition section 23 performs charging of the hand-held terminal 5 by transmitting the supplied power to the hand-held terminal 5 through the connector 21. In another embodiment, the base device 6 may include a battery, and power charged in the battery may be transmitted to the hand-held terminal 5. Furthermore, in the present embodiment, although charging is performed in a mode in which power is supplied through the connector, in another embodiment, power may be supplied through non-contact charging.

The base device 6 includes a projector 25 for projecting an image on a screen or a wall surface (including the ceiling). The projector 25 may be any display device that displays an image on a surface (may be uneven) away from the base device 6 by projecting the image on the surface. In the present embodiment, as shown in FIG. 3, the projector 25 is formed on the base device 6 such that a light projection section (lens) 25a faces upward, i.e., such that the image is projected upward. More specifically, in the present embodiment, the projector 25 projects the image on the ceiling. In the present embodiment, for example, the projector 25 displays an image encouraging awakening of the user or sleep onset (content for sleep onset described later, etc.), and displays an image showing an evaluation result of sleep when the user awakens in the morning.

In the present embodiment, the base device 6 corrects the image to be projected on the ceiling by using, if necessary, a technology of so-called projection mapping. More specifically, the base device 6 corrects the image such that an image in accordance with the unevenness and/or the color of the projection plane (ceiling) of the projector 25 is displayed. For that purpose, the base device 6 includes a camera 27 for correcting the image. As shown in FIG. 3, the camera 27 is formed on the base device 6 in a direction that includes an image capturing range of the location where the image is to be projected by the projector 25. Thus, the camera 27 is provided so as to face the same direction (upward) as the projector 25. The method for correcting the image will be described later.

The base device 6 includes a loudspeaker 26. The loudspeaker 26 is used for, for example, outputting a sound encouraging awakening or sleep onset of the user (content for sleep onset etc., described later).

The base device 6 includes a control section 22 that controls each section 23 to 27 of the base device 6. The control section 22 is connected to each of the sections 21 and 23 to 27 of the base device 6. The control section 22 executes various types of control processes executed by the base device 6. The control section 22 has a memory and a CPU (Central Processing Unit). In the base device 6, the various types of control processes are executed when the CPU uses the memory and executes information processing programs stored in the base device 6. For example, the control section 22 controls charging operation of the hand-held terminal 5 by controlling the power acquisition section 23. In addition, the control section 22 causes the projector 25 and/or the loudspeaker 26 to reproduce information and content to be presented to the user on the base device. Furthermore, the control section 22 transmits information sensed by the Doppler sensor 24 to the hand-held terminal 5.

It should be noted that the base device 6 may have another configuration in addition to or instead of the configuration shown in FIG. 2 indicate. For example, the base device 6 may include an environment sensor, a display, an indirectional loudspeaker, a light source (illumination), an odor generation device, and the like (see "[8. Modifications]" described later.

Next, the configuration of the server 3 will be described. The server 3 is formed of one or more information processing apparatuses (server device). Herein, a "server" refers to a single information processing apparatus (server device) and also to a whole server device group (server system) when the server is formed of multiple server devices.

In the present embodiment, although the server 3 will be described as an integral configuration, the server 3 may have a configuration including multiple server devices divided in accordance with function and/or role. For example, the server 3 may have a configuration including a data server that accumulates the QOL factor information acquired from the hand-held terminal 5 and a service server that conducts an evaluation on the basis of the QOL factor information to provide a network service. Furthermore, when the server 3 performs a service of providing a commodity or the like ("commodity or the like" means service is also included in addition to a commodity, and is described similarly in the following) as a part of the network service, the server 3 may have a configuration including a shop server for billing and providing the commodity or the like.

2. Operation Outline of Information Processing System

Figure 4:
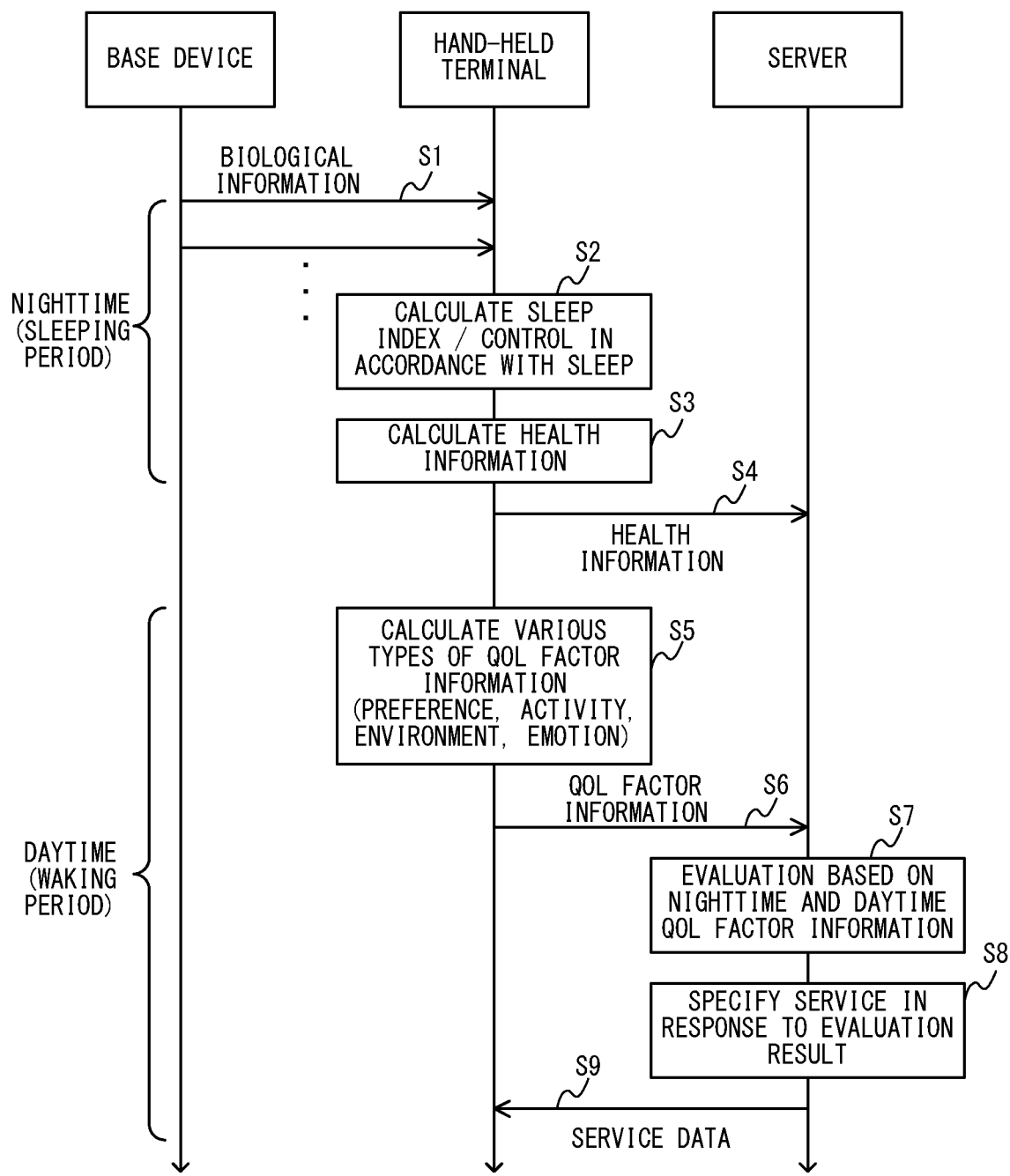
FIG. 4 is a timing chart showing a non-limiting example of the flow of the operation of the information processing system.

Next, a general outline of the operation of the information processing system 1 will be described. FIG. 4 is a timing chart showing one example of the flow of the operation of the information processing system. The timing chart of FIG. 4 shows one example of the flow of operation of the information processing system in a single day. As shown in FIG. 4, in the present embodiment, the information processing system 1 is used in different modes during nighttime (period in which the user is asleep) and daytime (period in which the user is awake).

In a sleeping period (typically, night), the hand-held terminal 5 is set in a state of being mounted on the base device 6. At this moment, the base device 6 senses biological information of the user by the Doppler sensor 24 and transmits the biological information to the hand-held terminal 5 connected to itself (step S1). During the sleeping period, the biological information is repeatedly sensed by the base device 6 and repeatedly transmitted to the hand-held terminal 5. Although not diagrammatically represented in FIG. 4, the base device 6 executes a process of presenting information and/or content to the user during the sleeping period by using the projector 25 or the like.

The hand-held terminal 5 calculates information (sleep information) related to the sleep of the user on the basis of the biological information acquired from the base device 6 (step S2). Although details will be described later, the sleep information includes an index regarding sleep (sleep index). The sleep index is a numerical value representing, for example, sleep hours, sleep latency, mid-sleep awake hours, and sleep efficiency, etc.

At an appropriate timing, the hand-held terminal 5 performs an operation in accordance with the sleep information, in other words, an operation in accordance with the sleep state of the user. Although details will be described later, for example, the hand-held terminal 5 sets its own operation mode to OFF-mode in response to sleep onset of the user and sets its own operation mode to ON-mode in response to awakening of the user. For example, the hand-held terminal 5 controls reproduction of content on the base device 6 in accordance with the sleep state and controls the information to be presented to the user by the base device 6 in accordance with the sleep state.

In addition, the hand-held terminal 5 calculates, as the QOL factor information, the health information based on the biological information acquired from the base device 6 (step S3). In the present embodiment, the hand-held terminal 5 calculates, as the health information, information including the sleep information and fatigue information. The fatigue information contains a fatigue index related to fatigue of the user. Although details will be described later, the fatigue index is calculated as a numerical value representing the fatigue level of the user while taking into consideration the sleep index. In the present embodiment, the health information is calculated in response to awakening of the user (i.e., in response to ending of the sleeping period).

When the health information is calculated, the hand-held terminal 5 transmits the calculated health information to the server 3. The server 3 stores (accumulates) the received health information distinctively for each user (each hand-held terminal).

As described above, during the sleeping period, the terminal system 2 acquires the biological information from the user in sleep, and calculates the health information (index related to fatigue and sleep). The calculated health information is stored in the server 3.

On the other hand, during the waking period (typically, daytime), the hand-held terminal 5 is removed from the base device 6 and is carried by the user. At this moment, the hand-held terminal 5 calculates, as the QOL factor information, the activity information, the environmental information, the emotion information, and the preference information (step S5). In FIG. 4, the process (step S5) for calculating the QOL factor information is shown only once. However, ordinarily, the process is executed multiple times during a single waking period (one day) at an appropriate timing in the waking period. Thus, in the present embodiment, the QOL factor information is calculated in accordance with various behaviors of the user while awake. For example, in response to walk movement of the user, the activity information indicating activity content (movement through walking) is calculated, and the environmental information indicating the environment through which the user is moving is calculated. In addition, for example, in response to the user participating a meeting at work, the emotion information indicating the emotion of the user in the meeting is calculated. Furthermore for example, in response to the user stopping by a gymnasium on the way home from work, the preference information indicating the user's interest to physical exercise is calculated.

The hand-held terminal 5 transmits the calculated QOL factor information to the server (step S6). It should be noted that the hand-held terminal 5 may transmit the QOL factor information to the server 3 every time the QOL factor information is calculated, or transmit multiple sets of the QOL factor information to the server 3 in response to arrival of a predetermined timing. The server 3 stores (accumulates) the received QOL factor information distinctively for each user (each hand-held terminal).

The server 3 performs an evaluation based on the QOL factor information acquired from the hand-held terminal 5 (step S7). This evaluation is performed on the basis of the health information acquired during nighttime (sleeping period), and the activity information, the environmental information, and the emotion information which are acquired during daytime (waking period). In the present embodiment, the server 3 calculates, as a factor index for determining a QOL index, a health index based on the health information and the activity information, an environmental index based on the environmental information, and an emotion index based on the emotion information (see FIG. 10 described later). Furthermore, the server 3 calculates the QOL index on the basis of these three factor indices. Details of calculation methods for each of the indices will be described later. In the manner described above, the server 3 performs an evaluation related to health, environment, and emotion of the user, and performs an evaluation regarding QOL of the user on the basis of these evaluation results.

Furthermore, the server 3 provides a network service in accordance with the evaluation results. More specifically, the server 3 specifies, on the basis of the evaluation results (step S8), service content to be provided, and transmits, to the hand-held terminal 5, data (service data) related to the specified service (step S9).

The network service to be provided may be any content. In the present embodiment, the server 3 provides, to the terminal system 2 (the hand-held terminal 5), advice information and/or recommendation information in accordance with the evaluation results. The advice information is information including an advice for improving the various types of indices (QOL index, etc.) indicating the evaluation results. In addition, the recommendation information is information for introducing a recommended commodity or the like to the user for improving the various types of indices indicating the evaluation results.

In addition, the server 3 provides, as the network service, content in accordance with the evaluation results with respect to the terminal system 2 (the hand-held terminal 5). The content is, for example, content for improving the various types of indices indicating the evaluation results, and is more specifically music for improving insomnia, video for resolving stress, and the like.

Furthermore, the server 3 gives, as the network service, a privilege in accordance with the evaluation results to the user of the terminal system 2 (the hand-held terminal 5). This privilege may be a privilege related to the network service or may be a privilege related to the hand-held terminal 5. For example, the privilege may be a privilege related to a charge the user has to pay for the network service, more specifically, may be points that can be used when purchasing a commodity or the like introduced by the recommendation information. Furthermore, the privilege may be a privilege related to a charge the user has to pay for using the hand-held terminal 5, more specifically, may be a privilege regarding discount of a usage charge for the hand-held terminal 5 (e.g., telephone call charges).

In the present embodiment, an evaluation process (step S7) and a service provision process (steps S8 and S9) by the server 3 are executed at a predetermined timing in a single day, specifically, are executed at a timing of reaching a predetermined clock time. This predetermined clock time may be preset on the server 3 side or may be set to a clock time instructed in advance by the user of the hand-held terminal 5. In another embodiment, the predetermined timing may be specified on the basis of activity of the user. For example, the predetermined timing may be a timing when the user has returned home, or may be a timing when the user has left his/her workplace. These timings can be specified on the basis of, for example, the activity information.

As described above, in the present embodiment, the information processing system 1 calculates the health information related to the user in sleep (step S3), and calculates the activity information, the environmental information, the emotion information, and the preference information related to the user while awake (step S5). Then, the information processing system 1 evaluates QOL of the user on the basis of these QOL factor information (step S7). With this, since various types of information related to the user are calculated throughout the day, QOL of the user reflecting the behavior and state of the user through the day can be evaluated.

3. Operation of Terminal System During Sleeping Period

3-1: Operation Example

Figure 5:
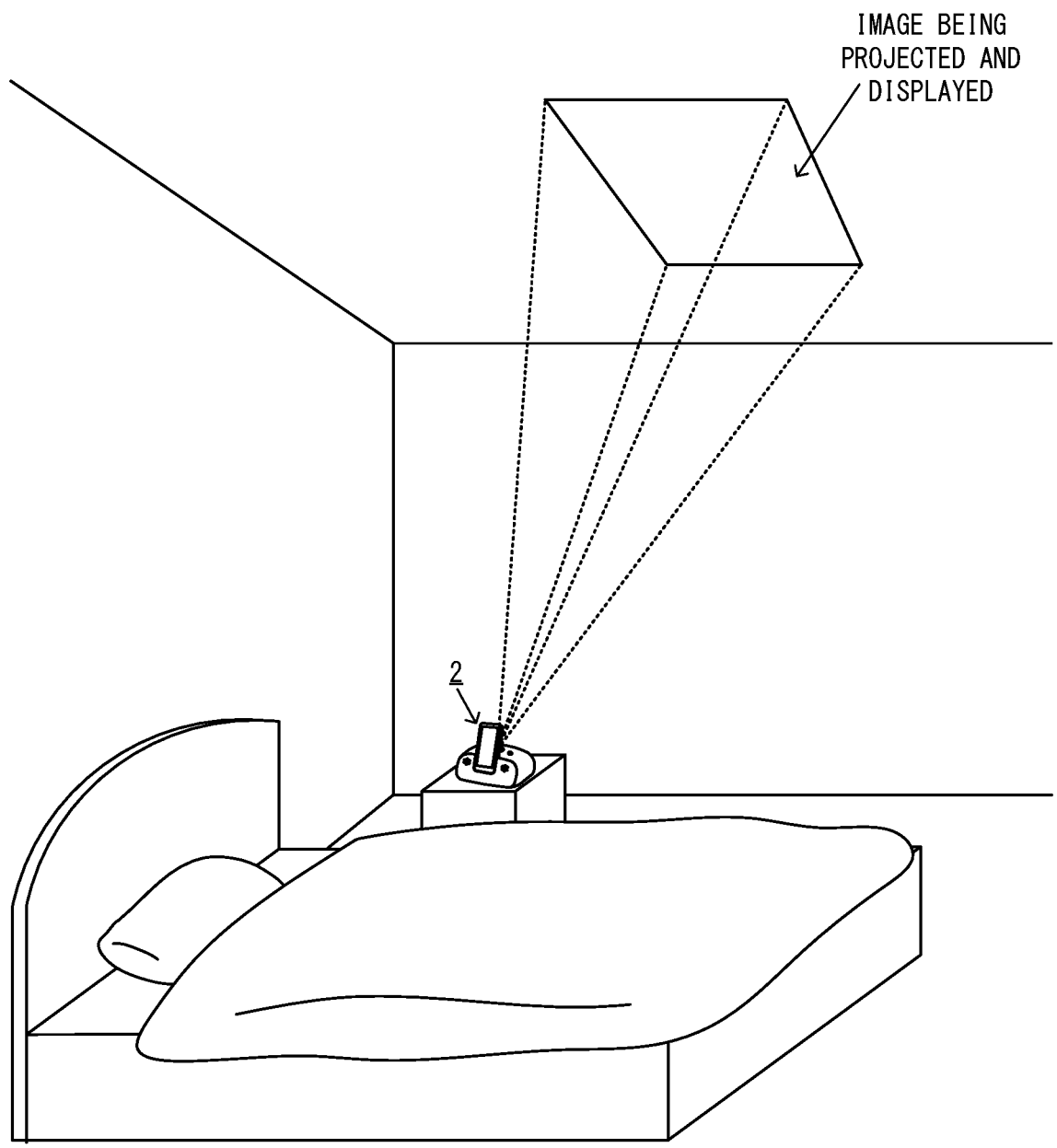
FIG. 5 shows a non-limiting example of how the terminal system 2 is arranged.

Next, an operation example of the terminal system during the sleeping period will be described. FIG. 5 shows one example of how the terminal system 2 is arranged. As shown in FIG. 5, in the present embodiment, the base device 6 is disposed in the bedroom of the user. The base device 6 is disposed around (bedside, etc.) the user. In addition, as shown in FIG. 5, during the sleeping period, the hand-held terminal 5 is mounted on the base device 6. Thus, the user mounts the hand-held terminal 5 on the base device 6 when going to bed. In response, operation by the terminal system 2 during the sleeping period is started (see FIG. 6).

In the present embodiment, the base device 6 has a function of charging the hand-held terminal 5. As a result, since the user can be motivated to mount the hand-held terminal 5 on the base device 6, the possibility of the user forgetting mounting of the hand-held terminal 5 on the base device 6 can be reduced.

Figure 6:
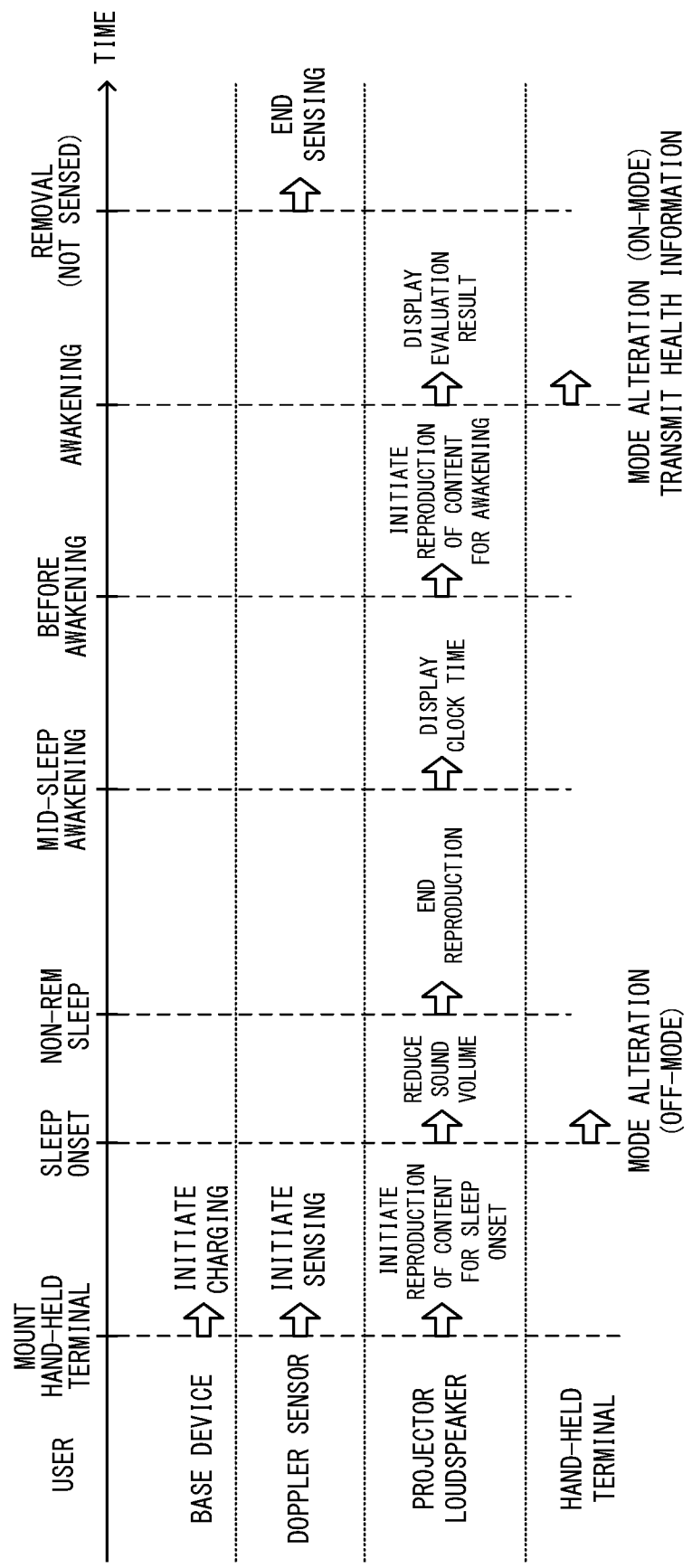
FIG. 6 shows a non-limiting example of the operation of the terminal system 2 during a sleeping period.

FIG. 6 shows one example of the operation of the terminal system 2 during the sleeping period. When the hand-held terminal 5 is mounted on the base device 6, the base device 6 initiates charging of the hand-held terminal 5. Although not diagrammatically represented, the base device 6 ends a charging operation in response the battery of the hand-held terminal 5 being charged to the capacity thereof. When the hand-held terminal 5 is mounted on the base device 6, if the remaining battery level of the hand-held terminal 5 is equal to or higher than a predetermined level (e.g., half of the battery capacity), the base device 6 may suspend the charging. This is because, in the present embodiment, there are cases where the user mounts the hand-held terminal 5 on the base device 6 for a purpose other than the purpose of charging (e.g., a purpose of sensing the biological information). For example, the hand-held terminal 5 may notify the remaining battery level to the base device 6 in response to being mounted on the base device 6, and the base device 6 may assess the necessity of charging on the basis of the notified remaining battery level. Alternatively, in response to being mounted on the base device 6, the hand-held terminal 5 may assess the necessity of charging on the basis of the remaining battery level, and notify the necessity of charging to the base device 6.

In addition, when the hand-held terminal 5 is mounted on the base device 6, the base device 6 initiates a sensing operation by the Doppler sensor 24 (see FIG. 6). A sensing result by the Doppler sensor 24 is transmitted to the hand-held terminal 5. The hand-held terminal 5 calculates the biological information (pulse, respiration, and body movement of the user) on the basis of the sensing result, and calculates the sleep index on the basis of the biological information (details described later). The sensing operation by the Doppler sensor 24 and a calculation process of the sleep index based on the sensing result are repeatedly executed during the sleeping period. In the present embodiment, the sensing operation by the Doppler sensor 24 is repeatedly executed until the user is no longer sensed. In addition, the calculation process of the sleep index is repeatedly executed until the user awakens.

Although details will be described later, the hand-held terminal 5 calculates, in real time, the sleep index representing the state of sleep of the user. Specifically, the hand-held terminal 5 can determine, in real time, at least whether the user is asleep or awake, and determine the depth of the sleep. It should be noted that "calculate (determine) in real time" as described above is not limited to a strict meaning of instantaneously calculating (determining), but is a meaning that also includes calculating (determining) with a delay of about several seconds.

As described above, in the present embodiment, since the terminal system 2 uses an unworn type sensor (the Doppler sensor 24) that can sense the biological information even without having the sensor worn by the user, the biological information can be sensed without obstructing the user (without disturbing sleep of the user).

In addition, when the hand-held terminal 5 is mounted on the base device 6, the base device 6 initiates reproduction of content for sleep onset by using the projector 25 and the loudspeaker 26 (see FIG. 6). The content for sleep onset is content for encouraging sleep onset of the user, in other words, content that has an effect of encouraging sleep onset of the user. For example, the content for sleep onset is an image of a starlit sky, a sound of water flowing through a river, and the like. In the present embodiment, the content for sleep onset is content formed of an image (video) and/or sound. It should be noted that the base device 6 may first display a menu image by using the projector 25, and enable the user to select the content to be reproduced from the menu image.

The content (e.g., content for sleep onset) to be reproduced on the terminal system 2 (the base device 6) during the sleeping period may be determined on the basis of the sleep index and/or the biological information (pulse, respiration, etc.) calculated during the sleeping period. For example, the terminal system 2 may determine, as the content to be reproduced, a music having a tempo matching the tempo of respiration or pulse, which is the biological information. For example, the terminal system 2 may specify the ideal rhythm during sleep from the sleep index, and determine, as the content to be reproduced, a music that guides the rhythm of respiration or pulse of the user to become a specific rhythm (e.g., a music having a tempo matching the rhythm). In addition, reproduction of the content may be controlled on the basis of the biological information and/or the sleep index. For example, the terminal system 2 may alter the tempo of the music to be reproduced so as to be a tempo matching the tempo of pulse of respiration and reproduce the music, or may alter the tempo of the music to a tempo matching an ideal rhythm during sleep and reproduce the music. At this moment, the tempo of the content (music) to be reproduced may be altered in real time in accordance with the tempo of respiration or pulse successively sensed (or in accordance with an ideal rhythm successively calculated on the basis of the successively calculated sleep index).

In the present embodiment, as shown in FIG. 5, the projector 25 projects an image (content for sleep onset) on the ceiling. Thus, the user can easily see the image in a sleeping position.

As described above, the terminal system 2 can determine the sleep state of the user depending on the mounting of the hand-held terminal 5 with respect to the base device 6. In the present embodiment, the terminal system 2 performs various operations in accordance with the sleep state of the user. In the following, specific examples of these various operations will be described.

(Alter Mode of Hand-Held Terminal 5 to OFF)

In the present embodiment, at a sleep onset (transition to a sleep state) of the user, the operation mode of the hand-held terminal 5 is altered (see FIG. 6). More specifically, at a sleep onset of the user, the hand-held terminal 5 determines that the user has entered a sleep state through a process of calculating the sleep index. In response, the hand-held terminal 5 alters the operation mode thereof from ON-mode to OFF-mode.

Here, the ON-mode is a mode in which the calculation processes for the activity information, the environmental information, the emotion information, and the preference information described above are executed. Furthermore, the ON-mode can be referred to as a mode in which the hand-held terminal 5 operates as a multifunctional device. While the user is awake, the mode of the hand-held terminal 5 is basically set to the ON-mode (as long as the user does not perform an operation of altering the mode).

On the other hand, the OFF-mode is a mode in which the calculation processes for the activity information, the environmental information, the emotion information, and the preference information described above are not executed. As described above, in the OFF-mode, power consumption can be reduced by not executing unnecessary processes during the sleeping period. It should be noted that, in the OFF-mode, communication function with respect to the server 3 may be maintained and not shut down or may be shut down.

In addition, in the OFF-mode, some of the functions among the functions as the multifunctional device are shut down. In the present embodiment, in the OFF-mode, the function of notifying about an incoming telephone call and E-mail (or any of those) by sound is shut down. With this, the possibility of disturbing sleep of the user by the sound of the hand-held terminal 5 can be reduced. For example, in the OFF-mode, the hand-held terminal 5 replays a message of a telephone answering machine to an opponent side without sounding a ring tone when there is an incoming phone call, and does not sound a ring tone when there is an incoming mail.

(Reproduction Control of Content for Sleep Onset)

In response to the hand-held terminal 5 determining that the user has entered the sleep state, the terminal system 2 changes the reproduction mode of the content for sleep onset (see FIG. 6). Specifically, the terminal system 2 shuts down image display (projection) by the projector 25. This is because image display by the projector is unnecessary during sleep. At this moment, the terminal system 2 may shut down power supply to the projector 25. In addition, the terminal system 2 reduces the output sound volume of the loudspeaker 26. This is because the purpose and effect of outputting the sound related to the content for sleep onset are small (or zero) during sleep. However, in the present embodiment, the possibility of the user waking up due to a sudden halt of the sound is taken into consideration, and the output sound volume is gradually reduced. In another embodiment, the terminal system 2 may shut down sound output by the loudspeaker 26.

Then, when the sleep of the user becomes deep (e.g., enter a state of non-REM sleep), the hand-held terminal 5 determines that the depth of the sleep of the user has reached or exceeded a predetermined standard from the process of calculating the sleep index. In response, the terminal system 2 shuts down reproduction of the content for sleep onset (see FIG. 6). As a result, reproduction of content having a small effect can be halted, and power consumption can be limited.

(Information Presentation at time of Mid-Sleep Awakening)

In the present embodiment, when the user awakens (mid-sleep awakening) in mid-course of sleep, the terminal system 2 presents the user with the current time (see FIG. 6). More specifically, when the user awakens in mid-course of sleep, the hand-held terminal 5 determines that the user has undergone mid-sleep awakening by the process of calculating the sleep index. In response, the terminal system 2 displays the current time (on the ceiling) by using the projector 25. With this, when the user wakes up in the middle of the night, the user can immediately know the current time. In addition, in the present embodiment, since the current time is displayed on the ceiling, the user can know the current time while in the sleeping position.

It should be noted that the judgment of being an awakening in mid-course of sleep (mid-sleep awakening) or an awakening at the time of arising (sometimes referred to as "arising awakening" for distinguishing from "mid-sleep awakening") can be performed by, for example, setting a judgment standard clock time. More specifically, the terminal system 2 can judge an awakening to be a mid-sleep awakening when the awakening of the user is determined to be before the judgment standard clock time and to be an arising awakening when the awakening of the user is determined to be at or after the judgment standard clock time. Here, the judgment standard clock time can be set based on a clock time at which the user is predicted to wake up (predicted arising clock time). For example, the terminal system 2 may set, as the judgment standard clock time, a clock time that is a predetermined time period (e.g., two hours) earlier than the predicted arising clock time. Furthermore, the predicted arising clock time may be calculated on the basis of past arising clock time (time of arising awakening) of the user, or may be set by the user. When the user has set the time of an alarm clock with respect to the terminal system 2 (the hand-held terminal 5), the time may be set as the predicted arising clock time.

(Reproduction Control of Content for Awakening)

In the present embodiment, when sleep of the user becomes shallow (e.g., enter an REM sleep state) as the predicted arising clock time approaches, the terminal system 2 initiates reproduction of content for awakening (see FIG. 6). Specifically, in the case described above, the hand-held terminal 5 determines that the user has entered a state prior to awakening through the process of calculating the sleep index. The determination of the user entering the state prior to awakening can be made when, for example, the sleep has become shallow and the time is within a predetermined time period (e.g., one hour) from the predicted arising clock time. In response to the user being determined as entering the state prior to awakening, the terminal system 2 initiates reproduction of the content for awakening. The content for awakening is content for encouraging awaken of the user, and is, in other words, content having an effect of encouraging awaken of the user. Examples the content for awakening include an image of bright blue sky, chirping sound of a bird, and the like. In the present embodiment, the content for awakening is content formed of an image (video) and/or sound. When the content for awakening is reproduced, the user can be encouraged to wake up comfortably at an appropriate timing.

(Presentation of Evaluation Result at Time of Awakening)

In the present embodiment, when the user awakens (arising awakening), evaluation of the sleep of the user is performed and the evaluation results are presented to the user (see FIG. 6). Specifically, when the hand-held terminal 5 determines that arising awakening has occurred from the method described above in "(Information Presentation at time of Mid-Sleep Awakening)"; the terminal system 2 performs an evaluation of the sleep of the user on the basis of (multiple sets of) the sleep index related to the recent sleeping period. It should be noted that "the sleep index related to the recent sleeping period" refers to a sleep index calculated on the basis of the biological information sensed during the recent sleeping period. The terminal system 2 displays an image representing the evaluation result on the ceiling by using the projector 25.

Figure 7:
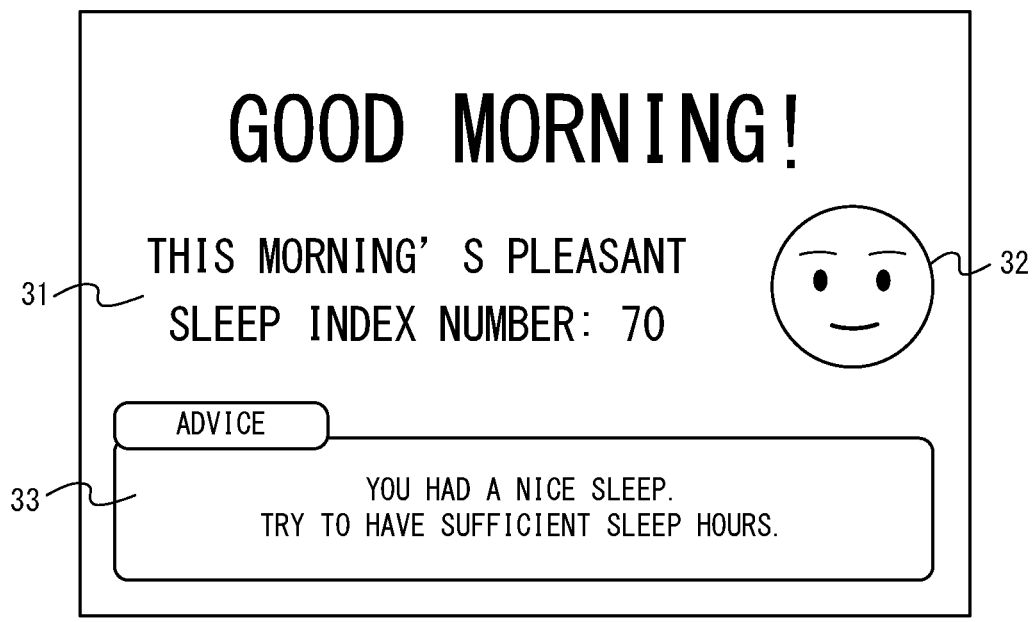
FIG. 7 shows a non-limiting example of an image projected by a projector and representing an evaluation result.

FIG. 7 shows one example of the image projected by the projector and representing the evaluation result. In the present embodiment, the terminal system 2 calculates a pleasant sleep index number as the evaluation result. More specifically, as shown in FIG. 7, the terminal system 2 displays a pleasant sleep index number 31 calculated on the basis of the sleep information. For example, the pleasant sleep index number ranges from 0 to 100 points and is calculated such that the numerical value is higher when the evaluation result is better (when the quality of the sleep is better). More specifically, the pleasant sleep index number may be calculated by assigning an index specific weight to a predetermined one or more types of sleep indices. By displaying the evaluation result as a numerical value (score), the quality of the sleep can be presented to the user in an easily understandable manner.

In addition, the terminal system 2 displays a face image 32 representing the evaluation result (see FIG. 7). The face image 32 is displayed such that the display style thereof (specifically facial expression) is changed depending on the pleasant sleep index number. For example, when the pleasant sleep index number is at a moderate level, a face image representing an ordinary facial expression is displayed; when the pleasant sleep index number is relatively high (the evaluation result being good), a face image representing a smiley facial expression is displayed (see FIG. 7); and, when the pleasant sleep index number is relatively low (the evaluation result being bad), a face image representing a fatigued facial expression is displayed. By displaying such a face image 32 as the evaluation result, the user can recognize the evaluation result intuitively.

It should be noted that the terminal system 2 may display, as the evaluation result, a raw numerical value of the sleep index such as, for example, sleep hours and sleep latency. Furthermore, a numerical value does not necessarily have to be always displayed as the evaluation result, and, for example, solely the face image 32 may be displayed as the evaluation result.

In addition, the terminal system 2 displays advice information 33 representing an advice in accordance with the evaluation result (see FIG. 7). The advice information 33 represents an advice for improving the quality of the sleep. The advice information 33 is generated on the basis of the sleep information and/or the sleep index number. For example, an advice information with different content may be displayed depending on the magnitude of the sleep index number (magnitude of the numerical value). The content of the advice information may be determined on the basis of various types of sleep indices such as, for example, sleep hours, sleep latency, and mid-sleep awake hours. Furthermore, in another embodiment, recommendation information may be displayed instead the advice information 33 (or in addition to the advice information 33).

In another embodiment, in addition to information of the evaluation result being projected and displayed on the projector 25, other information different from the information projected and displayed by the projector 25 may be displayed on the display 17 of the hand-held terminal 5. For example, information calculated from the evaluation result may be displayed on the display 17. "Information calculated from the evaluation result" may be, for example, statistical information (e.g., information showing the change of the sleep index number for the past one week) of the sleep index number which is the evaluation result, or may be information (e.g., the advice information and recommendation information described above) related to the network service based on the evaluation result.

(Alteration of Mode of Hand-Held Terminal 5 to ON/Transmission of Health Information)

In the present embodiment, when the user awakens (arising awakening), the operation mode of the hand-held terminal 5 is altered to the ON-mode (see FIG. 6). More specifically, when the hand-held terminal 5 determines that arising awakening has occurred from the method described above in "(Information Presentation at time of Mid-Sleep Awakening)"; the hand-held terminal 5 alters the operation mode thereof from the OFF-mode to the ON-mode. As a result, while the user is awake, since the hand-held terminal 5 is automatically maintained in the ON-mode, the user can use the hand-held terminal 5 without being obstructed.

In addition, when the user awakens (arising awakening), the hand-held terminal 5 calculates the health information on the basis of the sleep information (sleep index), and transmits the health information to the server 3 (see FIG. 6). The health information calculated here includes the sleep information and the fatigue information (fatigue index) calculated from the sleep information. The calculation method for the fatigue index will be described later.

As described above, in the present embodiment, the terminal system 2 performs various operations in accordance with the sleep state of the user during the sleeping period of the user. When the sleeping period ends (when the user awakens), the user moves (e.g., exits the bedroom) and leaves the sensing range of the Doppler sensor 24. Thus, when the user is no longer sensed by the Doppler sensor 24, the terminal system 2 ends the sensing operation of the Doppler sensor 24 (see FIG. 6). As a result, the terminal system 2 ends the operation performed during sleep of the user.

In another embodiment, when the base device 6 and the hand-held terminal 5 are wirelessly communicable, the terminal system 2 may alter the operation mode of the hand-held terminal 5 to the ON-mode in response to a subject being no longer sensed by the Doppler sensor 24. More specifically, when the subject is no longer sensed by the Doppler sensor 24, the base device 6 sends a notification to the hand-held terminal 5, and the hand-held terminal 5 alters the operation mode to the ON-mode in response to receiving this notification.

The user, at the time of arising, may conceivably remove the hand-held terminal 5 from the base device 6 to be carried. Thus, in another embodiment, the terminal system 2 may alter the operation mode of the hand-held terminal 5 to the ON-mode in response to the hand-held terminal 5 being removed from the base device 6. More specifically, the hand-held terminal 5 may sense the connection state with the base device 6 in the OFF-mode, and, when the connection with the base device 6 is no longer sensed, may alter the operation mode of itself to the ON-mode.

In another embodiment, the terminal system 2 may end the sensing operation of the Doppler sensor 24 in response to awakening (arising awakening) of the user. Furthermore, in another embodiment, the terminal system 2 may end the sensing operation of the Doppler sensor 24 in response to the hand-held terminal 5 being removed from the base device 6.

Still further, in another embodiment, a measurement period of the biological information may be determined with any method, i.e., initiating or ending the sensing by the Doppler sensor 24 may be performed in accordance with any condition, and the following method may be used, for example.

For example, in another embodiment, the terminal system 2 may intermittently perform the sensing by the sensor (the Doppler sensor 24), and may determine the measurement period on the basis of the sensing result. Specifically, the terminal system 2 judges whether or not the user is sensed (whether or not the user exists within a sensing range) by performing the sensing by the Doppler sensor 24 at a predetermined time interval. When the user is not sensed, the terminal system 2 shuts down the sensing by the Doppler sensor 24. In this case, the measurement is not initiated. On the other hand, when the user is sensed, the terminal system 2 initiates the measurement by continuing the sensing by the Doppler sensor 24. When the measurement is initiated, the terminal system 2 continues the measurement while the user is sensed by the Doppler sensor 24. Thus, similarly to the embodiments described above, the terminal system 2 ends the measurement by the Doppler sensor 24 in response to the user being no longer sensed. As a result, the measurement period by the Doppler sensor 24 can be determined on the basis of the result of sensing (performed intermittently) by the Doppler sensor 24 itself. With this, since the measurement period can be determined without using other devices such as a sensor, the device configuration can be simplified.

In another embodiment, the measurement period with the Doppler sensor 24 may be determined on the basis of a sensing result from a sensor (e.g., human sensor) different from the Doppler sensor 24. For example, the terminal system 2 may use an infrared sensor and/or a camera as the human sensor. Specifically, the terminal system 2 intermittently or continuously senses the user by using the human sensor. During the period in which the user is sensed by the human sensor, the terminal system 2 performs measurement by the Doppler sensor 24. Also with this, the measurement period can be automatically determined similarly to the method of the present embodiment and the method for determining the measurement period on the basis of the sensing result from the Doppler sensor 24. Thus, since the user does not have to perform an operation for (initiating and ending) the measurement, usability of the terminal system 2 can be improved. Furthermore, since the measurement of the biological information can be performed without too much time and effort and without placing any burden on the user; continuous acquisition of the biological information can be performed easily.

In another embodiment, the measurement period with the Doppler sensor 24 may be predetermined. For example, the terminal system 2 may perform the measurement within a predetermined time zone (e.g., a time zone from 20:00 during the night to 10:00 in the next morning), or may constantly perform the measurement (as long as a shut-down operation is performed by the user). Similarly to above, also with this, since the user does not have to perform an operation for initiating and ending the measurement, usability of the terminal system 1 can be improved.

In addition, in the embodiment described above, the terminal system 2 automatically (in other words, without a specific operation by the user) calculates the health information (sleep index and fatigue index) based on the biological information, in addition to automatically performing the measurement of the biological information. Thus, since the health information is calculated in the terminal system 2 without having the user perform a special operation, usability of the terminal system 2 can be improved.

3-2: Calculation Method of Health Information

Figure 8:
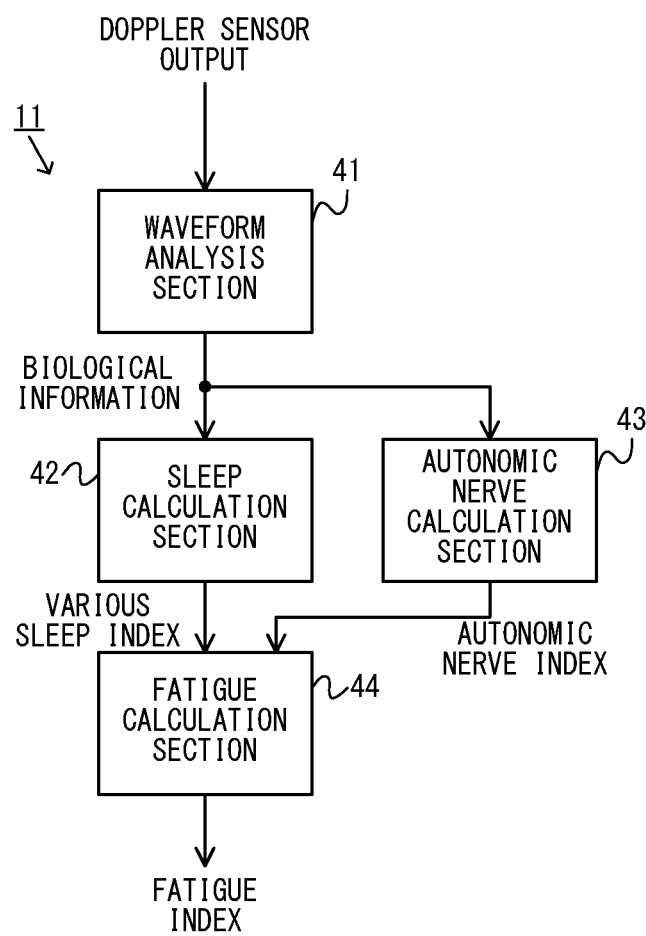
FIG. 8 is a functional block diagram showing a non-limiting example of the functional configuration for calculating health information in a processing section 11 of a hand-held terminal 5.

In the following, a process for calculating the health information (sleep index and fatigue index) on the basis of the sensing result from the Doppler sensor 24 will be described. FIG. 8 is a functional block diagram showing one example of the functional configuration for calculating health information in the processing section 11 of the hand-held terminal 5. As shown in FIG. 8, the processing section 11 includes a waveform analysis section 41, a sleep calculation section 42, an autonomic nerve calculation section 43, and a fatigue calculation section 44.

The waveform analysis section 41 calculates respiration, pulse, and body movement as additional biological information on the basis of the biological information (output waveform) sensed by the Doppler sensor 24. Conventionally, obtaining waveforms representing respiration, pulse, and body movement has been known to be possible through separation of the output waveform of the Doppler sensor 24 in accordance with the frequency. The waveform analysis section 41 separates the output waveform through frequency analysis and the like into a frequency bandwidth corresponding to respiration, a frequency bandwidth corresponding to pulse, and a frequency bandwidth corresponding to body movement, and individually outputs the separated waveform data. As shown in FIG. 8, an output from the waveform analysis section 41 is inputted to both the sleep calculation section 42 and the autonomic nerve calculation section 43.

The sleep calculation section 42 calculates various types of sleep indices on the basis of the biological information (respiration, pulse, and body movement). Conventionally, methods for calculating the sleep indices on the basis of respiration, pulse, and body movement are known. In the present embodiment, the sleep calculation section 42 calculates sleep indices indicating the following information.

Sleep latency (sleep onset latency)
Mid-sleep awake hours
Number of times of mid-sleep awakening
Sleep efficiency
Total sleep hours
Activity level during sleep
Sleep stage
REM sleep hours
Non-REM sleep hours
Sleep quality In another embodiment, only some of the sleep indices described above may be calculated, or a type of sleep index different from the sleep indices described above may be calculated.

The autonomic nerve calculation section 43 calculates an index (autonomic nerve index) indicating the action level of the autonomic nerves (sympathetic nerves and parasympathetic nerves) on the basis of the biological information. Specifically, the waveform of pulse (RR interval) included in the biological information is frequency-analyzed by using maximum entropy method and Fourier transformation to calculate a high frequency component (approximately 0.15 to 0.40 [Hz]) HF and a low frequency component (approximately 0.04 to 0.15 [Hz]) LF of the waveform. The high frequency component HF is known to indicate the action level of parasympathetic nerves and the low frequency component LF is known to indicate the action level of sympathetic nerves. In addition, it is known that the fatigue level can be evaluated from a ratio between the action level of parasympathetic nerves and the action level of sympathetic nerves (e.g., see Japanese Laid-Open Patent Publication No. 2010-201113). Thus, the autonomic nerve calculation section 43 calculates a ratio (LF/HF) between the high frequency component HF and the low frequency component LF as the autonomic nerve index. As shown in FIG. 8, an output from the autonomic nerve calculation section 43 is used as an input for the fatigue calculation section 44.

The fatigue calculation section 44 calculates the fatigue index on the basis of the sleep indices and the autonomic nerve index. In the present embodiment, as the fatigue index, a fatigue level indicating the degree (level) of fatigue with a numerical value ranging from 0 to 100 is calculated. Although any method can be used for calculating the fatigue index, for example, the following methods are conceivable. It should be noted that, hereinafter, the fatigue level calculated here is referred to as a "first fatigue level" in order to distinguish that from a fatigue level corresponding to a waking period described later.

A first method is a method of calculating the fatigue index from the sleep indices. Here, the sleep indices are thought to correlate with the first fatigue level. For example, the following are examples in which the first fatigue level is speculated to be high.

Long sleep latency.
Long mid-sleep awake hours.
Frequent mid-sleep awakening.
Low sleep efficiency.
Short total sleep hours.
Upset of balance between REM sleep hours and non-REM sleep hours (the ratio between REM sleep hours and non-REM sleep hours being outside the normal range).

Thus, the fatigue calculation section 44 calculates the first fatigue level such that the first fatigue level becomes high when the sleep indices fit the examples described above and such that the first fatigue level becomes low when the sleep indices does not fit the examples described above. For example, the fatigue calculation section 44 may judge whether or not any of the items described above are satisfied, calculate points in accordance with the number of satisfied items, and calculate the first fatigue level in accordance with the total points. At this moment, the fatigue calculation section 44 may calculate weighted points for each of the items. Furthermore, a reference value (e.g., "six hours" for the total sleep hours) may be set for each of the items, and the points may be calculated such that the points become larger as the value of a calculated sleep index deviates more from the reference value.

As described above, in the present embodiment, the sleep indices related to sleep of the user is calculated on the basis of the biological information, and the fatigue index is calculated on the basis of the sleep indices. Since a correlation is thought to exist between the sleep indices and the degree of fatigue as described above, the accuracy of the fatigue index can be improved by calculating the fatigue index on the basis of the sleep indices.

A second method is a method of calculating the fatigue index on the basis of the autonomic nerve index. As described above, it is known that the first fatigue level can be evaluated by using the balance of the action levels of sympathetic nerves and parasympathetic nerves, i.e., the autonomic nerve index. Thus, for example, the fatigue calculation section 44 calculates the first fatigue level such that the first fatigue level becomes higher as the value of the autonomic nerve index deviates more from the reference value.

In the present embodiment, the fatigue calculation section 44 calculates the first fatigue level by use the first and second methods. Specifically, the fatigue calculation section 44 calculates respective fatigue levels from the two methods, and calculates the final first fatigue level on the basis of the respective calculated fatigue levels. The fatigue calculation section 44 may, for example, use an average of the two fatigue levels as the final first fatigue level, or may calculate the final first fatigue level by assigning a weight to one of the two fatigue levels.

In another embodiment, in addition to the two methods described above, the first fatigue level may be calculated by using the method described next. That is, a method of calculating the first fatigue level on the basis of sleep hours within a predetermined period of time (e.g., one week) may be used. Conventionally, in a Fatigue Risk Management System (FRMS), a technique of calculating the fatigue level on the basis of sleep hours and work hours exists. In the technique, for example, by setting the work hours as a constant for simplification, the first fatigue level can be calculated on the basis of sleep hours (alone).

In another embodiment, any method can be used for calculating the fatigue index, and any type content of the fatigue index can be used. In another embodiment, as the fatigue index, a value indicating the fatigue level for each type of fatigue may be calculated. For example, in another embodiment, the fatigue index may be three types of values, i.e., a value indicating the level of acute fatigue, a value indicating the level of accumulative fatigue, and a value indicating the level of mental fatigue.

In another embodiment, the health information may be calculated by using the sensing results from the camera 16 and/or the microphone 15. For example, biological information such as pulse and/or body movement can be calculated on the basis of an image of the user captured by the camera 16. Thus, the processing section 11 may calculate the sleep indices (and the fatigue index) by using the biological information obtained from the imaged captured by the camera 16 in addition to (or instead of) the biological information obtained from the sensing results of the Doppler sensor 24. Furthermore, the processing section 11 may take into consideration a snoring sound sensed by the microphone 15 to calculate the sleep indices.

3-3: Specific Example of Processes Executed by Terminal System 2

Figure 9:
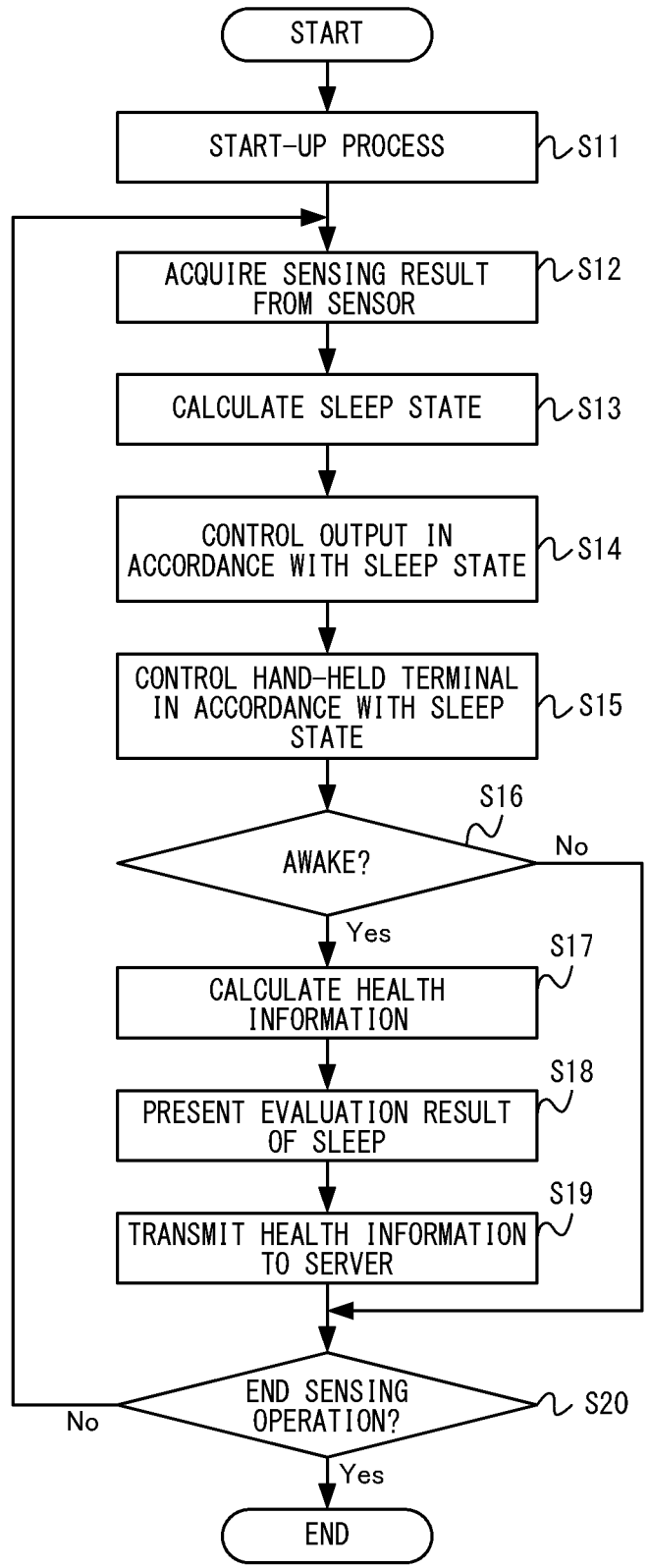
FIG. 9 is a flowchart showing a non-limiting example of the flow of processes executed by the terminal system during the sleeping period.

Next, a specific example of processes executed in the terminal system 2 during the sleeping period will be described. FIG. 9 is a flowchart showing one example of the flow of processes executed by the terminal system during the sleeping period. The series of processes shown in FIG. 9 is initiated in response to the hand-held terminal 5 being mounted on the base device 6. In another embodiment, the series of processes described above may be initiated in response to starting of communication between the hand-held terminal 5 and the base device 6, or may be initiated in response to the user performing a predetermined initiation operation with respect to the hand-held terminal 5 or the base device 6. Each of the processes shown in FIG. 9 is executed by either one of, or in cooperation between the hand-held terminal 5 and the base device 6.

In the present application, the process at each step in the flowchart shown in the drawing is merely one example, and, as long as a similar result is obtained, the processing sequence of each step may be switched or another process may be executed in addition to (or instead of) the process as each of the steps. Herein, although the process at each of the steps in the flowchart is described as to be executed by a CPU of each device (the hand-held terminal 5, the base device 6, and the server 3); processes of one portion of the steps in the flowchart may be executed by a dedicated circuit or a processor other than a CPU.

First, at step S11, the terminal system 2 executes a start-up process. The start-up process is a process executed in response to the start of the series of processes shown in FIG. 9 (in the present embodiment, in response to the hand-held terminal 5 being mounted on the base device 6). In the present embodiment, as the start-up process, a charging initiation process, a sensing initiation process, and a reproduction initiation process are executed (see FIG. 6). In another embodiment, any process may be executed as the start-up process. One or two of the three processes described above may be executed, another process different from the three processes may be executed, or the start-up process may be eliminated and not executed.

In the charging initiation process, the base device 6 initiates charging of the hand-held terminal 5. Specifically, the control section 22 gives an instruction to the power acquisition section 23 to initiate charging. In response to this instruction, the power acquisition section 23 supplies power, supplied from an external power supply, to the hand-held terminal 5 via the connector 21. It should be noted that the base device 6 here is in a state of being connected to the external power supply (i.e., a state in which a power plug is connected to an electrical outlet). The base device 6 may confirm the remaining battery level of the hand-held terminal 5, and initiate the charging operation under a condition that the remaining battery level is equal to or lower than a predetermined level. The charging operation started at step S11 ends in response to the battery of the hand-held terminal 5 being charged to the capacity thereof.

In addition, in the sensing initiation process, the base device 6 initiates, in order to calculate the health information, sensing by the sensor (the Doppler sensor 24) that senses the biological information. More specifically, the control section 22 of the base device 6 gives an instruction to the Doppler sensor 24 to initiate the sensing operation. In response to this instruction, the Doppler sensor 24 initiates the sensing operation.

Furthermore, in the reproduction initiation process, the base device 6 initiates reproduction of the content for sleep onset. More specifically, the control section 22 reads out the content for sleep onset stored in advance, and reproduces the content for sleep onset by using the projector 25 and the loudspeaker 26. It should be noted that the content (content at sleep onset or content for awakening) reproduced on the base device 6 may be stored in the base device 6, may be stored in the hand-held terminal 5, or may be acquired from an external device (e.g., the server 3) via the hand-held terminal 5.

After the process at step S11, the processes at steps S12 to S20 described in the following are repeatedly executed during the sleeping period. In the present embodiment, the process loop for steps S12 to S20 is executed at a rate of once every predetermined time period.

At step S12 the terminal system 2 acquires the sensing result (biological information) from the Doppler sensor 24. The Doppler sensor 24, which has initiated the sensing operation by the sensing initiation process at step S11, outputs the sensing result (output waveform) to the control section 22. The control section 22 transmits the sensing result to the hand-held terminal 5 (step S1 shown in FIG. 4). With this, the sensing result from the Doppler sensor 24 is acquired by the hand-held terminal 5. The control section 22 may transmit information of the sensing result of the Doppler sensor 24 directly to the hand-held terminal 5, or may process the sensing result in some way (e.g., process of removing noise included in signals of the sensing result, process of calculating the sleep index, etc.) and transmit the processed result to the hand-held terminal 5.

At step S13, the hand-held terminal 5 calculates the sleep information (various types of sleep indices) (step S2 shown in FIG. 4). More specifically, the processing section 11 calculates the various types of sleep indices on the basis of the sensing result (biological information) acquired at step S12. Calculation of the sleep indices is performed by the method described in "(3-2: Calculation Method of Health Information)" above. At step S13, the processing section 11 only has to calculate information (sleep indices) used for determining the sleep state of the user at steps S14 and S15 described later. At step S13, the processing section 11 does not have to calculate the fatigue information (fatigue index) and sleep indices (e.g., total sleep hours), which can only be calculated when the sleeping period ends.

At step S14, the hand-held terminal 5 controls output of the base device 6 in accordance with the sleep state of the user (step S2 shown in FIG. 4). More specifically, the processing section 11 controls output of the base device 6 (output from the projector 25 and/or the loudspeaker 26) on the basis of the sleep indices calculated at step S13. Specifically, the processing section 11 judges whether or not the sleep state of the user has entered a predetermined state on the basis of the sleep indices calculated at step S13. Examples of the predetermined state include a state of sleep onset of the user, a state of being in a deep sleep, a mid-sleep awakening state, a state prior to awakening, and the like (see FIG. 6). The processing section 11, when judged that the predetermined state is obtained, executes a reproduction control process in accordance with the state. In the present embodiment, with the process at step S14, the operations for controlling the power supply of the projector 25 and controlling reproduction of the content for sleep onset, the operation for displaying the clock time in response to mid-sleep awakening, and the operation for controlling reproduction of the content for awakening (see FIG. 6) are executed as described above.

In another embodiment, when content and/or information are/is to be presented to the user during the sleeping period, the terminal system 2 may perform an output from the hand-held terminal 5 in addition to or instead of the output from the base device 6. For example, the display of the current time performed in response to mid-sleep awakening of the user may be performed on the hand-held terminal 5. In addition, for example, the output of sound (music) in accordance with reproduction of the content by the projector 25 may be performed on the hand-held terminal 5. It should be noted that an image identical to or different from the image projected and displayed by the projector 25 may be displayed on the hand-held terminal 5.

At step S15, the hand-held terminal 5 controls the hand-held terminal 5 in accordance with the sleep state of the user (step S2 shown in FIG. 4). More specifically, the processing section 11 controls the operation mode of the hand-held terminal 5 on the basis of the sleep indices calculated at step S13. Specifically, the processing section 11 judges, similarly to step S14, whether or not the sleep state of the user has entered a predetermined state. The processing section 11, when judged that the predetermined state is obtained, alters the operation mode of the hand-held terminal 5 to a mode in accordance with the state. In the present embodiment, the altering operation to the OFF-mode and the altering operation to the ON-mode are executed by the process at step S15.

The process at step S15 may be a process for alter the settings of the hand-held terminal 5 regardless of the operation mode of the hand-held terminal 5. For example, the hand-held terminal 5 may alter the settings of the output sound volume and/or the settings of the screen display of the hand-held terminal 5 in accordance with the sleep state of the user. For example, when the user is in the sleep state, the output sound volume of the hand-held terminal 5 may be set to zero, or the screen display may be set OFF.

At step S16, the hand-held terminal 5 judges whether or not the user has awakened (arising awakening). More specifically, the processing section 11 judges whether or not the user has awakened on the basis of the sleep indices calculated at step S13 from the method described in "(Information Presentation at time of Mid-Sleep Awakening)" above. When the user is judged to be awake, the series of processes at steps S17 to S19 is executed. On the other hand, when the user is judged not to be awake, the series of processes at steps S17 to S19 is skipped and the process at step S20 is executed.

At step S17, the hand-held terminal 5 calculates the health information on the basis of the information (biological information) acquired during the sleeping period (step S3 shown in FIG. 4). The health information is calculated from the method described in "(3-2: Calculation Method of Health Information)" above. In the present embodiment, at step S17, the processing section 11 calculates the autonomic nerve index on the basis of the biological information acquired at step S12. In addition, the processing section 11 calculates the sleep indices (e.g., total sleep hours, etc.) that cannot be calculated during the sleeping period on the basis of the biological information acquired at step S12. Furthermore, the processing section 11 calculates the fatigue index (first fatigue level) on the basis of the various types of sleep indices and the autonomic nerve index. With this, the health information including the sleep indices and fatigue index is calculated. In another embodiment, the health information may include only one of the sleep information (sleep indices) and the fatigue information (fatigue index).

At step S18, the terminal system 2 presents the user with an evaluation result of the sleep. More specifically, the processing section 11 generates an image (see FIG. 7) indicating the evaluation result based on the calculated sleep indices. In the present embodiment, the pleasant sleep index number and the advice information are calculated on the basis of the sleep indices, and an image containing the calculated information is generated. The processing section 11 transmits the generated image to the base device 6. The control section 22 of the base device 6 projects and displays the received image (on the ceiling) by using the projector 25. With this, the image indicating the evaluation result is presented to the user. In another embodiment, generation of the image may be performed by the base device 6. More specifically, the hand-held terminal 5 may transmit the information of the calculated sleep indices to the base device 6, and generate the image on the basis of the sleep indices received by the base device 6.

At step S19, the hand-held terminal 5 transmits the calculated health information to the server 3 (step S4 shown in FIG. 4). More specifically, the processing section 11 transmits, by the communication section 10, the health information calculated at step S17 to the server 3. With this, the health information for a single sleeping period is transmitted to the server 3, and is saved in the server 3. In the manner described above, in the present embodiment, the hand-held terminal 5 automatically transmits, to the server 3, the information that is to be transmitted (even without an instruction from the user). Thus, the information is uploaded to the server 3 without an instruction by the user.

At step S20, the base device 6 judges whether or not the sensing operation by the Doppler sensor 24 is to be ended. Specifically, the control section 22 judges whether or not the user is no longer sensed (whether the user has left the sensing range of the sensor) on the basis of the sensing result from the Doppler sensor 24. When the user is no longer sensed, the control section 22 judges that the sensing operation is to be ended, and ends the series of processes shown in FIG. 9. On the other hand, when the user is sensed, the control section 22 judges not to end the sensing operation, and executes the process at step S12 once again. Subsequently, unless a judgment to end the sensing operation is made at step S20, the series of processes at steps S12 to S20 is repeatedly executed.

In another embodiment, at step S19, the terminal system 2 may transmit the health information to the server 3 and then end the series of processes shown in FIG. 9. In this case, the process at step S12 is executed once again when the judgment result is negative at step S16, and the processes at steps S12 to S16 are repeatedly executed until the judgment result at step S16 changes to positive.

In the present embodiment, when the hand-held terminal 5 is removed from the base device 6 for some reason (e.g., when the user rolls over in bed and accidently hits the hand-held terminal 5) during the sleeping period, the base device 6 cannot transmit the sensing result from the Doppler sensor 24 to the hand-held terminal 5. In this case, the base device 6 stores, in a storage section (memory, etc.) thereof, the data of the sensing result that could not be transmitted to the hand-held terminal 5. Then, in response to the next time when the hand-held terminal 5 is mounted on the base device 6, the base device 6 transmits, to the hand-held terminal 5, the data of the sensing result stored in the storage section. The hand-held terminal 5 that has received the data, calculates the sleep indices on the basis of the sensing result (step S13). It should be noted that the hand-held terminal 5 does not necessarily have to execute a control process (steps S14, S15) based on the sleep indices calculated at this moment. This is because the sleep indices calculated here are based on past sensing results.

When the user is judged to be awake on the basis of the calculated sleep indices (when the judgment result at step S16 is positive), the hand-held terminal 5 executes the processes at steps S17 to S19. As described here, even when the hand-held terminal 5 is removed from the base device 6 while the user is asleep, the health information is calculated and transmitted to the server 3 in response to the next time when the hand-held terminal 5 is mounted on the base device 6. Thus, for example, when the user awakens and notices that the hand-held terminal 5 is removed from the base device 6, the user may mount the hand-held terminal 5 on the base device 6. With this, the terminal system 2 can present the evaluation result of the sleep to the user and transmit the health information to the server 3.

In another embodiment, in a case where the hand-held terminal 5 and the base device 6 are wirelessly communicable, the processes of steps S12 to S19 can be executed continuously even if the hand-held terminal 5 is removed from the base device 6.

At step S14, an image is projected and displayed on the ceiling by the projector 25. When the image is to be projected and displayed by the projector 25, the base device 6 may execute a correction process for correcting the image. The correction process is a process for correcting the image such that a proper image is projected and displayed, by taking into consideration the unevenness and color of the projection spot (ceiling) of the projector 25. The base device 6 performs, on the image to be projected and displayed by the projector 25, a correction that takes into consideration the color and unevenness of a projection spot on the basis of an image of the projection spot captured by the camera 27. Specifically, as shown in FIG. 9, before executing a process, the base device 6 projects and displays a predetermined test image on the ceiling by the projector 25. At this moment, when there is unevenness on the ceiling, the projected and displayed test image will be distorted when compared to the original test image. In addition, when the ceiling has a color, the projected and displayed test image will have a different color from the original test image. The base device 6 captures an image of the test image that has been projected and displayed on the ceiling by the camera 27 and that is distorted or has been changed in color when compared to the original test image. Then, the base device 6 specifies a correction process for correcting the original test image such that the test image projected and displayed on the ceiling will be displayed properly, on the basis of the image captured by the camera 27. More specifically, the base device 6 specifies the content of the correction process for correcting the original test image such that the projected and displayed test image is displayed in the correct shape at the uneven projection spot and in the correct color at the projection spot. When the correction process is specified, the base device 6 stores the content of the correction process.

At step S14, when the image is to be projected and displayed by the projector 25, the base device 6 corrects the image by the stored correction process, and projects and displays a corrected image by the projector 25. With this, the projected and displayed image is restored to a proper shape (the same shape as the original image) with the proper color (the same color as the original image). The correction process describe above may be performed by a method similar to the technique for conventional projection mapping. In addition the correction process may be a correction that takes into consideration only one of the unevenness and color of the projection spot.

4. Operation of Terminal System During Daytime

4-1: Operational General Outline

Figure 10:
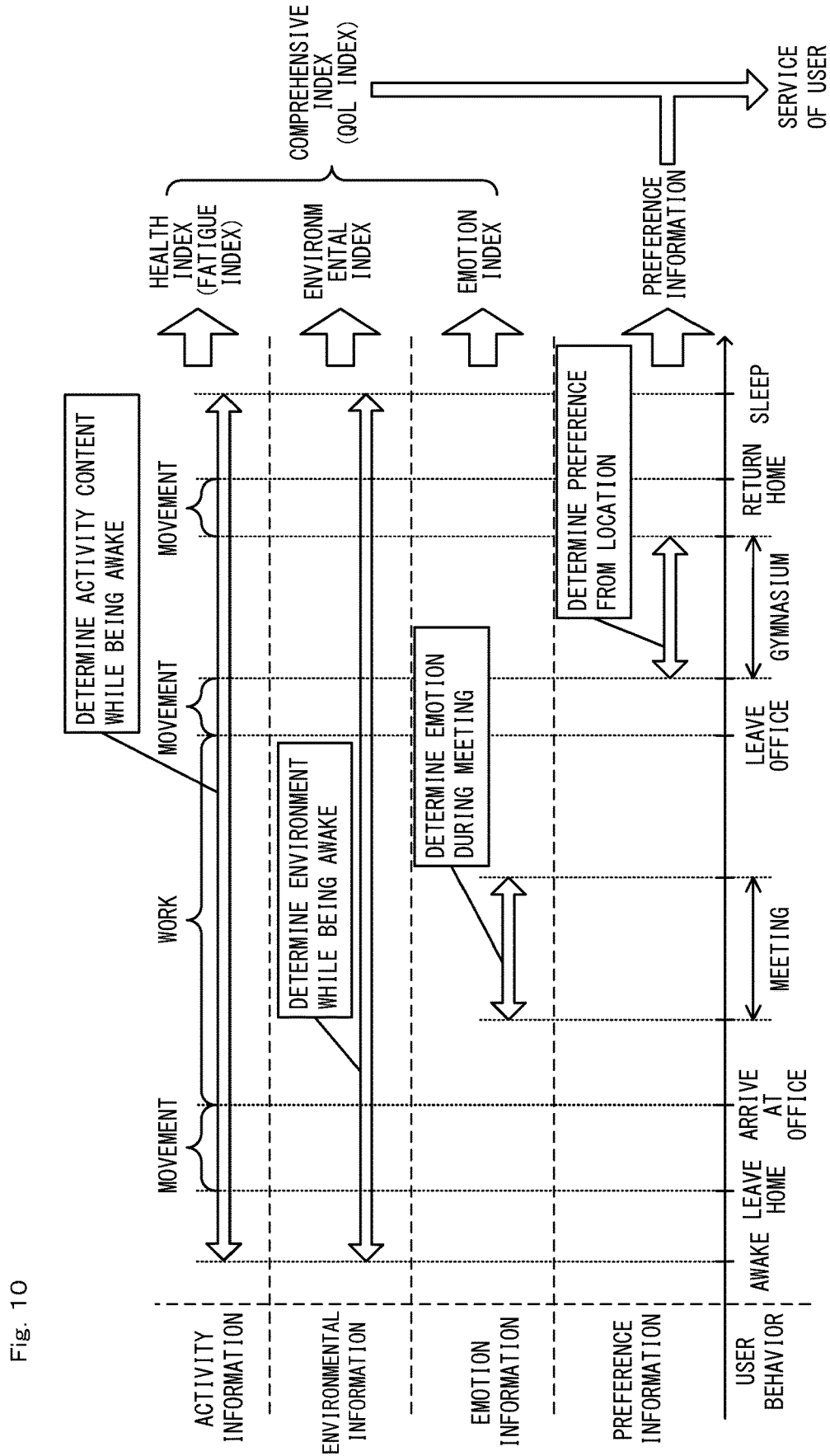
FIG. 10 shows one example of the relationship between the behavior of the user during the waking period and various types of information determined by the information processing system.
Figure 11:
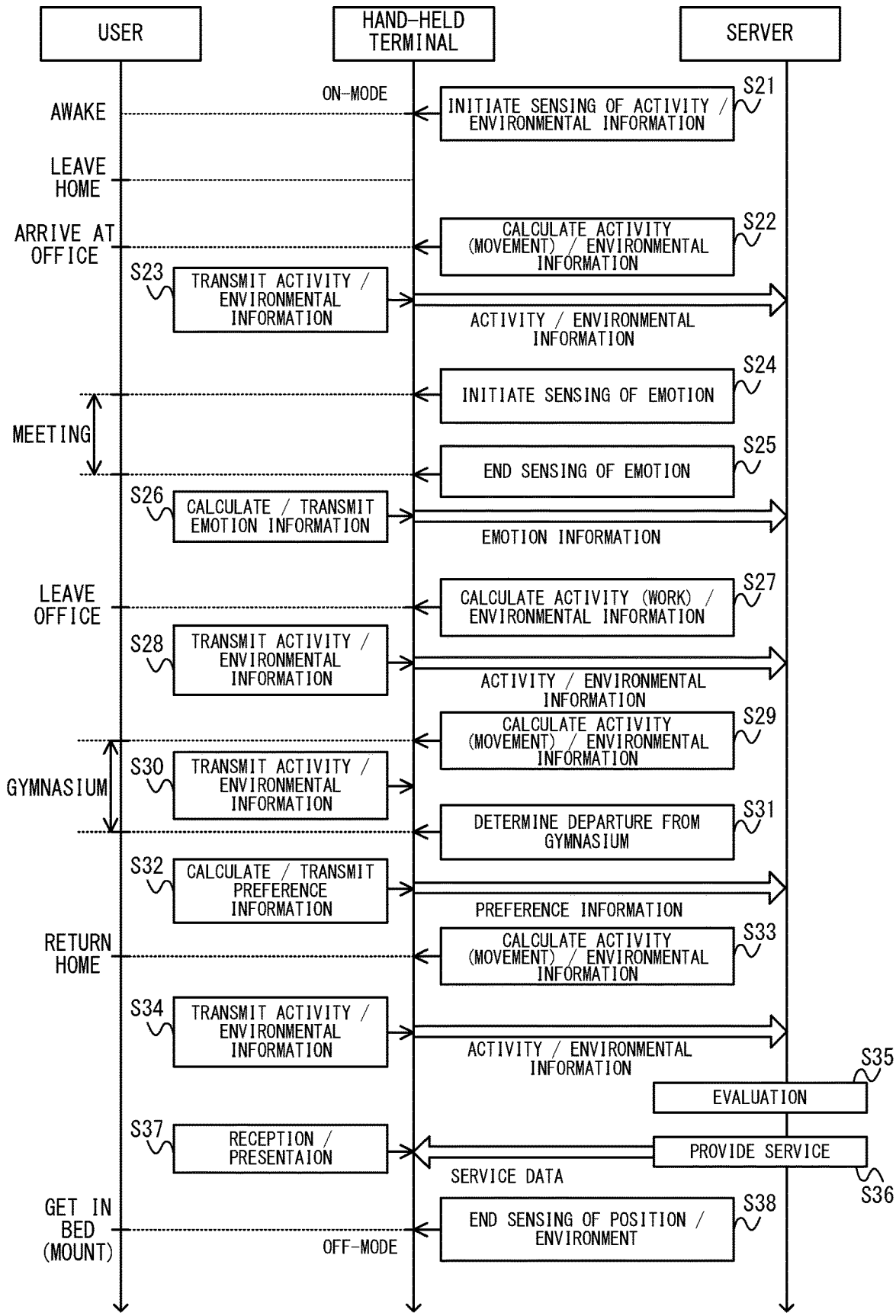
FIG. 11 is a timing chart showing a non-limiting example of the flow of the operation of the information processing system during the waking period.

Next, a general outline of an operation of the information processing system during the waking period will be described. FIG. 10 shows one example of the relationship between the behavior of the user during the waking period and various types of information determined by the information processing system. FIG. 11 is a timing chart showing one example of the flow of the operation of the information processing system during the waking period. FIG. 10 shows, as an example of the behavior of the user in a single day, a case in which the user goes to office, attends a meeting, stops by at the gymnasium after leaving office, and returns home. Described in the following as an example is an operation of the information processing system when user behaves in the manner as shown in FIG. 10 as a single day behavior.

As described above, in the present embodiment, the operation mode of the hand-held terminal 5 is altered to the ON-mode in response to awakening of the user. In response to the operation mode set to the ON-mode, the hand-held terminal 5 initiates a process for calculating the QOL factor information (activity information, environmental information, emotion information, and preference information) that should be calculated during the waking period. More specifically, the hand-held terminal 5 initiates sensing of positional information by the position sensing section 13, and sensing of environment sensor information by the environment sensor 14 (step S21 shown in FIG. 11). Although details will be described later, the positional information is used for calculating the activity information, and the environment sensor information is used for calculating the environmental information. In the present embodiment, sensing of the positional information and sensing of the environment sensor information are repeatedly executed in the ON-mode (see FIG. 10).

In the example shown in FIG. 10, the user leaves home after awakening, and goes to his/her workplace. At this moment, the hand-held terminal 5 calculates, on the basis of the positional information, activity information indicating that the user has moved (step S22 shown in FIGS. 10 and 11). More specifically, when the sensed position indicated by the positional information starts moving from a certain location (here, home) to another location (here, workplace) and stops, the hand-held terminal 5 calculates the activity information indicating the movement.

Although the content of the activity information indicating the movement may be in any form, activity information including a movement method and a movement amount is calculated in the present embodiment. Although details will be described later, as the movement method, either one of walking, train, and automobile is specified. As the movement amount, a moved distance and/or moving hours are/is calculated. In another embodiment, the activity information indicating the movement may include information indicating the location prior to movement (departure location; home in the example of step S22) and/or a location after movement (destination; workplace in the example of step S22).

In the present embodiment, when the activity information is calculated, the hand-held terminal 5 calculates the environmental information corresponding to the activity information. The "environmental information corresponding to the activity information" is environmental information indicating the environment of the user in a period during which the activity indicated by the activity information has been performed. At step S22, environmental information indicating the environment of the user in a period during which the movement has been performed is calculated. Although details will be described later, in the present embodiment, the hand-held terminal 5 calculates environmental information (see FIG. 15) including information (activity content shown in FIG. 15) indicating the content of the activity performed by the user and information (environmental values shown in FIG. 15) indicating average ambient temperature and humidity sensed during the activity.

When the activity information and the environmental information are calculated as described above, the hand-held terminal 5 transmits the calculated activity information and environmental information to the server 3 (step S23). The server 3 stores (accumulates) the received activity information and environmental information distinctively for each user (each hand-held terminal). Also in the subsequent processes at steps S26, S28, S30, S32, and S34; the server 3, when the QOL factor information is received from the hand-held terminal 5, stores the information distinctively for each user, similarly to step S23.

As shown in FIG. 10, the user attends a meeting after arriving at the office. At this moment, the hand-held terminal 5 determines the emotion of the user during the meeting. More specifically, the hand-held terminal 5 calculates the emotion information indicating the emotion during the meeting, and transmits the calculated emotion information to the server 3 (steps S24 to S26 shown in FIGS. 10 and 11). The calculation of the emotion information is performed as described next.

First, in response to the start of the meeting, the hand-held terminal 5 initiates sensing of information for calculating the emotion information (step S24). In the present embodiment, the judgment of whether or not the meeting has been started is performed on the basis of schedule information stored in the hand-held terminal 5. More specifically, schedule information indicating the date and time when the meeting starts and ends is preregistered in the hand-held terminal 5. The hand-held terminal 5 judges whether or not the meeting has started by referring to the schedule information, and initiates the sensing when the meeting starts.

At step S24, the hand-held terminal 5 senses, as information for calculating the emotion information, the sound sensed by the microphone 15. More specifically, the hand-held terminal 5 initiates sound sensing by the microphone 15.

When the meeting ends, the hand-held terminal 5 ends sensing of the information (step S25). More specifically, The hand-held terminal 5 ends sensing of sound by the microphone 15. It should be noted that the judgment of whether or not the meeting has ended can be performed on the basis of the schedule information stored in the hand-held terminal 5.

When the meeting ends, the hand-held terminal 5 calculates the emotion information on the basis of the information sensed during the meeting (information of sound sensed by the microphone 15) (step S26). Although details will be described later, in the present embodiment, the hand-held terminal 5 determines the emotion of the user on the basis of voice and the like of the user sensed by the microphone 15, and calculates, as the emotion information, information indicating the determination result. Although details will be described later, in the present embodiment, emotion information representing the level (emotion intensity) of five types of emotions of anger, joy, sadness, hate, and pleasure is calculated.

As described above, when the user attends the meeting, sound during the meeting is sensed, and the emotion of the user is determined on the basis of sensed sound. Although not diagrammatically represented in FIGS. 10 and 11, in the present embodiment, other than during the meeting, the emotion of the user is determined also while the user is operating the hand-held terminal 5. Although details will be described later, while the user is operating the hand-held terminal 5, the hand-held terminal 5 captures an image of the user by using the camera 16, and determines the emotion of the user on the basis of facial expression of the captured user.

In the example shown in FIG. 10, the user leaves the office after the meeting ends. At this moment, the hand-held terminal 5 calculates activity information indicating work (has been done) (step S27 shown in FIGS. 10 and 11). More specifically, when the sensed position indicated by the positional information starts moving from a specific location (here, workplace), the hand-held terminal 5 determines that the user has stayed at the specific location, and calculates the activity information activity (here, work) corresponding to the specific location. Although any content may be used as the content of the activity information indicating the activity corresponding to the location, in the present embodiment, activity information including activity content (work) and active hours (work hours) is calculated (see FIG. 13).

When the activity information indicating work is calculated as described above, the hand-held terminal 5 calculates the environmental information corresponding to the activity information. The calculation method of the environmental information is similar to the process at step S22. More specifically, at step S27, the hand-held terminal 5 calculates the environmental information indicating the environment of the user in a period during which the user is working.

When the activity information and the environmental information are calculated as described above, the hand-held terminal 5 transmits the calculated activity information and environmental information to the server 3 similarly to the process at step S23 (step S28).

In the example shown in FIG. 10, the user stops by at the gymnasium after leaving office. When the user arrives at the gymnasium, the hand-held terminal 5 calculates, on the basis of the positional information, activity information indicating that the user has moved (step S29 shown in FIGS. 10 and 11). The process for calculating the activity information indicating the movement is similar to the process at step S22. In addition, similarly to step S22, the hand-held terminal 5 calculates the environmental information corresponding to the activity information, and transmits the calculated activity information and environmental information to the server 3 (step S30).

In the example shown in FIG. 10, the user leaves the gymnasium after finishing the activity (physical exercise, etc.) at the gymnasium. At this moment, the hand-held terminal 5 determines that the user has stayed at a specific location (here, gymnasium) by a process similar to that at step S27. Then, the hand-held terminal 5 calculates the preference information on the basis of the location where the user has stayed, and transmits the calculated preference information to the server 3 (step S32).

The calculated preference information may be information in any format indicating hobby or preference of the user. In the present embodiment, the preference information represents a genre determine to be of interest of the user, among a plurality of genres (items). Examples of the plurality of genres include physical exercise, health, cosmetics, fashion, music, movies, news, cooking, meal, pet, game, and the like. Although details will be described later, the hand-held terminal 5 stores, in advance, a table showing the association between location (facility) and the genre described above. When the user is determined to have stayed at a specific location (facility), the hand-held terminal 5 specifies a genre associated with the location in the table. For example, in the table, the genres of "physical exercise" and "health" are associated with gymnasium. Thus, when the user stops by at the gymnasium, the preference information representing "physical exercise" and "health" is calculated (generated).

Although not diagrammatically represented in FIGS. 10 and 11, in the present embodiment, the preference information is in some cases calculated on the basis of information inputted by the user (details will be described later). For example, when the user browses a web page on the Internet by using the hand-held terminal 5, the hand-held terminal 5 may determine the preference on the basis of search phrases inputted to a search engine website by the user, or the preference may be determined on the basis of the content of the browsed web page (e.g., keywords, etc., contained in the web page).

In the example shown in FIG. 10, the user returns home after leaving the gymnasium. When the user returns home, the hand-held terminal 5 calculates, on the basis of the positional information, the activity information indicating that the user has moved (step S33 shown in FIGS. 10 and 11). The process for calculating the activity information indicating the movement is similar to the process at step S22. In addition, similarly to step S22, the hand-held terminal 5 calculates the environmental information corresponding to the activity information, and transmits the calculated activity information and environmental information to the server 3 (step S34).

In the present embodiment, when a predetermined evaluation timing arrives, the server 3 performs a QOL factor information-based evaluation of the user on the basis of the QOL factor information transmitted from the hand-held terminal 5 (step S36 shown in FIG. 11, step S7 shown in FIG. 4). More specifically, the server 3 calculates various types of indices (health index, environmental index, emotion index, and QOL index) on the basis of various types of QOL factor information (health information, activity information, environmental information, and emotion information) received from the hand-held terminal 5. The QOL factor information-based evaluation of the user is performed for each user (user receiving a network service) having a hand-held terminal (step S36).

As shown in FIG. 10, in the present embodiment, the health index indicating the health (fatigue level) of the user is calculated on the basis of the health information and the activity information, the environmental index indicating the environment surrounding the user is calculated on the basis of the environmental information, and the emotion index indicating the emotion of the user is calculated on the basis of the emotion information. In addition, a QOL index which is a comprehensive index is calculated on the basis of the health index, the environmental index, and the emotion index described above. Details of the calculation method for these indices will be described later.

Although the evaluation timing when the server 3 performs the evaluation may be any timing, in the present embodiment, the evaluation timing is a timing when a predetermined clock time determined in advance has arrived. The evaluation timing may be a timing set by the server 3 (provider of network service), or may be a timing specified by the user. In addition, the evaluation timing is not limited to the timing when the predetermined clock time has arrived, and may be set on the basis of the activity (the activity information) of the user. For example, the evaluation timing may be a timing when the user has left office, or may be a timing when the user has returned home.

In addition, the number of times the server 3 performs the evaluation is not limited to once per day, and may be multiple times per day. For example, the server 3, every time the QOL factor information is received from the hand-held terminal 5, may perform the evaluation based on the received QOL factor information. At this moment, the server 3 may execute an evaluation other than the overall evaluation (calculation of an index other than the QOL index) every time the QOL factor information is received, and may execute the overall evaluation (calculation of the QOL index) once per day at a predetermined evaluation timing. In addition, the server 3 may, if QOL factor information satisfying a predetermined condition is received (e.g., when a predetermined type of QOL factor information is received), perform the QOL factor information-based evaluation in accordance with the timing of reception, and may, if QOL factor information not satisfying the predetermined condition is received, perform the evaluation not in accordance with the timing of reception (perform the evaluation later).

After performing the evaluation, the server 3 provides the user with a network service in accordance with the evaluation result (step S37 shown in FIG. 11, steps S8 and S9 shown in FIG. 4). More specifically, the server 3 specifies service content to be provided to the user on the basis of the various types of indices calculated at step S36 (see FIG. 10). As described above, in the present embodiment, as the network service, (a) presenting the evaluation result, (b) presenting advice information for improving the evaluation result, (c) presenting recommendation information that recommends a commodity or the like for improving the evaluation result, (d) providing content for improving the evaluation result, and (e) giving a privilege or the like in accordance with the evaluation result, are performed.

In the present embodiment, as the service of presenting the evaluation result, information including an index number representing each of the indices described above is transmitted to the hand-held terminal 5 and presented to the user (FIG. 24, etc.). As the advice information, for example, when an evaluation result (environmental index) indicating that the user has been in a hot environment is calculated, advice information showing a method for preventing exhaustion due to the summer heat may be presented to the user. As the recommendation information, for example, when an evaluation result (health index) indicating accumulation of fatigue is calculated, recommendation information that recommends a commodity that is effective for the recovery from fatigue may be presented to the user. As content provided by the network service, for example, when an evaluation result (health index) indicating insufficient sleep is calculated, music content that is effective for easy sleep onset may be provided, and, when an evaluation result (emotion index) indicating depressed feelings is calculated, content for invigorating the feelings may be provided. As the privilege, for example, when an evaluation (health index) indicating the user successfully maintaining a healthy state is calculated, a privilege that gives points that can be used in the network service may be given, or a privilege of discounting usage charge of the hand-held terminal 5 may be given.

In the present embodiment, the server 3 specifies the service content on the basis of the preference information (see FIG. 10). For example, the server 3 may alter the type of the commodity or the like to be recommended in the recommendation information, on the basis of the genre that is of interest of the user and indicated by the preference information. Specifically, even when the same evaluation result is calculated for a certain user, if the preference information indicates interest in physical exercise, the server 3 may present recommendation information related to sporting goods, and, if the preference information indicates interest in meal, the server 3 may present recommendation information related to health food. For example, the server 3 may alter content of the privilege to be given on the basis of the preference information. For example, when a commodity is to be gifted to the user as the privilege, the server 3 may determine the type of the commodity on the basis of the genre of interest of the user indicated by the preference information.

After specifying the service content, the server 3 transmits, to the hand-held terminal 5, the service data associated with the network service (see FIG. 11). Examples of the service data include data of the evaluation result, data of advice information, data of recommendation information, data of content to be provided, and/or data related to privilege (data indicating notification of privilege bestowal, data of the privilege itself), etc.

Although details will be described later, in the present embodiment, service data associated with the network service in accordance with the evaluation result related to a certain user is in some cases transmitted to a terminal of a user other than the user (e.g., family or friend of the user) in addition to the user (person himself/herself) who is the subject of evaluation. At this moment, the content of the service data transmitted to the user who is the subject of evaluation and the content of the service data transmitted to the other user may be different.

As described above, in the present embodiment, an evaluation is performed by the server 3 at a timing when a predetermined clock time has arrived, and providing of the network service is performed in response to performing of the evaluation. Here, the timing for providing the network service may be any timing. For example, in another embodiment, the timing is not limit to when the predetermined clock time has arrived, and the network service may be provided at a timing set on the basis of activity (the activity information) of the user. For example, the server 3 may provide the network service at a timing when the user leaves office or a timing when the user has returned home.

In another embodiment, when the server 3 performs the evaluation every time the QOL factor information is received, the server 3 may provide the network service every time the evaluation is performed. In addition, when an evaluation result satisfying the predetermined condition is calculated, the server 3 may provide the network service based on the evaluation in accordance with the calculated timing, and, when an evaluation result not satisfying the predetermined condition is calculated, the server 3 may provide (provide later) the network service not in accordance with the calculated timing. It should be noted that "when an evaluation result satisfying the predetermined condition is calculated" is, for example, when an evaluation result based on a predetermined type of QOL factor information is calculated, or when an evaluation result of a predetermined result is calculated. For example, in the example shown in FIG. 10, when the result of an evaluation performed in response to the end of the meeting indicates that the user is depressed, advice information such as, for example, "take a deep breath" may be transmitted from the server 3 to the hand-held terminal 5 at a timing immediately after the end of the meeting. In addition, for example, when the result of an evaluation performed in response to the end of movement indicates that the user has moved under a hot environment, advice information for prevent heatstroke may be transmitted from the server 3 to the hand-held terminal 5 at a timing immediately after the end of the movement.

The hand-held terminal 5 receives the service data transmitted from the server 3. Then, the hand-held terminal 5 presents the user with information associated with the service data by using the received service data (step S38). With this, for example, an evaluation result, advice information, and/or recommendation information are displayed on the display 17 of the hand-held terminal 5, content associated with the service is reproduced on the hand-held terminal 5, or a notification indicating that a privilege associated with a service has been given is displayed on the hand-held terminal 5.

In another embodiment, the terminal capable of receiving the network service does not necessarily have to be the hand-held terminal 5. More specifically, the information associated with the service data may be presented on another device not the hand-held terminal 5. For example, the content to be provided by the network service may be acquired by the hand-held terminal 5 and reproduced by the base device 6. In addition, for example, the server 3 may transmit the service data to a preregistered terminal (e.g., user's home personal computer) different from the hand-held terminal 5.

As described above, in the present embodiment, in the waking period of the user, the hand-held terminal 5 calculates the QOL factor information such as the activity information, the environmental information, the emotion information, and the preference information, and transmits the QOL factor information to the server 3. Based on QOL factor information received during the sleeping period and QOL factor information acquired in the waking period, the server 3 performs an evaluation regarding the health, activity, environment, and/or emotion of the user. Then the network service in accordance with the evaluation result is provided to the user.

As described above, the user mounts the hand-held terminal 5 on the base device 6 when going to bed (see FIG. 11). In response, the operation mode of the hand-held terminal 5 is transitioned to the OFF-mode. In response to the operation mode changing to the OFF-mode, the hand-held terminal 5 ends the process for calculating the QOL factor information to be calculated during the waking period. More specifically, the hand-held terminal 5 ends the sensing of the positional information by the position sensing section 13 and sensing of the environment sensor information by the environment sensor 14 (step S38 shown in FIG. 11).

In the present embodiment, the hand-held terminal 5 acquires the positional information and the environment sensor information throughout a single day (during the waking period). Here, in another embodiment, the condition (period and/or timing) for acquiring information for calculating the QOL factor information may be any condition. Thus, acquiring of the information for calculating the QOL factor information may be initiated and/or ended in accordance with satisfying of the predetermined condition. For example, in another embodiment, the hand-held terminal 5 may end acquiring of the positional information on the basis of activity (activity information) of the user. Specifically, the hand-held terminal 5 may end acquiring of the positional information in response to the user being determined to have returned home. For example, the hand-held terminal 5 may control initiation and/or end of acquiring of the environmental information on the basis of activity (activity information) of the user. Specifically, the hand-held terminal 5 may acquire the environmental information only while the user is conducting a predetermined activity (e.g., moving, working). For example, in another embodiment, an acquiring process may end at a timing when the service data is received from the server 3.

In the present embodiment, even after the service data is received, since the positional information and the environment sensor information are acquired, the activity information and the environmental information can be calculated. The hand-held terminal 5 transmits, to the server 3, positional information and environmental information calculated after receiving the service data, similarly to before receiving the service data. Thus, at the next evaluation timing (timing of evaluation to be performed tomorrow), the server 3 may perform an evaluation on the basis of positional information and environmental information calculated after receiving the service data. In addition, while the user is in bed, the server 3 may perform an evaluation on the basis of positional information and environmental information calculated after receiving the service data, and may transmit the service data based on the evaluation to the hand-held terminal 5 at a predetermined timing (e.g., a timing when the user awakens in the morning on the next day). For example, by having the hand-held terminal 5 perform the notification to the server 3 in response to mounting of the hand-held terminal 5 on the base device 6, the hand-held terminal 5 can notify the server 3 about when the user has gone to bed.

In another embodiment, after receiving the service data, the hand-held terminal 5 may shut down sensing of the positional information and the environment sensor information, or may shut down calculation of the activity information and the environmental information. In a case where the service data is received at a rate of once per a predetermined period of time, when the service data is received during the predetermined period of time, the hand-held terminal 5 may shut down calculation of the QOL factor information during the predetermined period of time and/or shut down acquiring (sensing) of the information for calculating the QOL factor information.

4-2: Process on Hand-Held Terminal

Next, specific examples of processes executed on the hand-held terminal 5 during the waking period will be described. In the ON-mode (during the waking period), the hand-held terminal 5 executes an activity information calculation process, an environmental information calculation process, an emotion information calculation process, a preference information calculation process, and an information presentation process. In the present embodiment, these processes are each executed by different programs (applications). The hand-held terminal 5 can execute various types of applications through multitasking. Other than the processes described above, applications depending on functions of the hand-held terminal 5 which is a multifunctional device may be executed as appropriate. In the following, details of each of the processes described above will be described.

(Activity Information Calculation Process)

Figure 12:
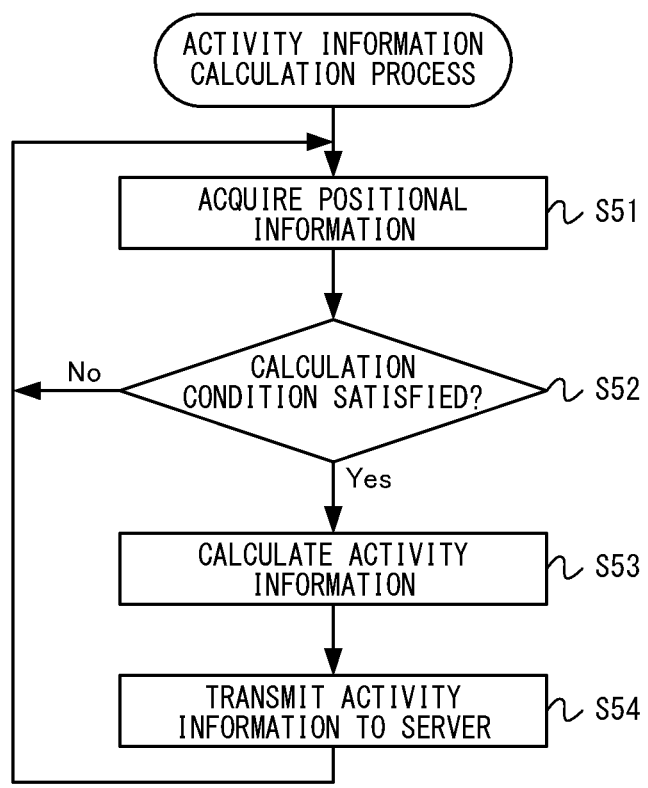
FIG. 12 is a flowchart showing a non-limiting example of the flow of an activity information calculation process.

FIG. 12 is a flowchart showing one example of the flow of the activity information calculation process. The activity information calculation process is a process of calculating the activity information indicating the activity of the user on the basis of the position (positional information) of the user. In the present embodiment, the activity information calculation process is continuously executed in the ON-mode. More specifically, in response to the operation mode of the hand-held terminal 5 being set to the ON-mode, the CPU of the processing section 11 initiates execution of a program for the activity information calculation process, and continuously executes the activity information calculation process until the operation mode is set to the OFF-mode.

First, at step S51, the processing section 11 acquires information used for calculating the activity information. In the present embodiment, the information used for calculating the activity information is the positional information described above. More specifically, the processing section 11 acquires the positional information from the position sensing section 13. In the present embodiment, the processing section 11 acquires, as clock time information corresponding to the positional information, clock time information indicating the clock time at the point in time when the positional information has been acquired. The acquired positional information and clock time information are stored in a memory of the processing section 11.

At step S52, the processing section 11 judges whether or not a condition to calculate the activity information has been satisfied. Although any condition may be used as this calculation condition, in the present embodiment, the user ending his/her movement (first condition), and the user staying at a location where the activity information is to be calculated (second condition) are used. When either one of the first condition and the second condition is satisfied, the condition to calculate the activity information is judged to be satisfied.

Whether or not the first condition is satisfied can be judged by determining, for example, whether or not a sensed position indicated by the positional information has moved from a certain location and then stopped at another location for a predetermined time period or longer (e.g., ten minutes or longer). It should be noted that when the sensed position is not separated from the certain location by a predetermined distance or more, or the duration of the movement is equal to or shorter than a predetermined time period, the processing section 11 may assess that the sensed position has not moved from the certain location. As a result, through the processes at steps S22, S29, and S33 described above, the processing section 11 can determine that the user has moved from a certain location to another location (e.g., movement from home to workplace, movement from workplace to gymnasium, etc.).

Whether or not the second condition is satisfied is judged in the manner described next. That is, the processing section 11 first judges whether or not the sensed position has stayed at a certain location for a predetermined time period or longer (e.g., fifteen minutes or longer) and then started moving. When the processing section 11 judges that staying for a predetermined time period or longer has not occurred, or that the movement has not started, the processing section 11 judges that the second condition is not satisfied. On the other hand, when the processing section 11 judges that movement has started after staying occurred, the processing section 11 specifies the type of the staying location. The type of the staying location may be, for example, a location related to the user such as home or workplace, or a facility such as a gymnasium, a restaurant, or a movie theater. In the present embodiment, the position of the location related to the user is registered and stored in the hand-held terminal 5 in advance. In addition, the position of a facility is specified by using, for example, map information in which a position on a map and a facility existing at that position are associated. The map information may be stored in the hand-held terminal 5 in advance, or may be acquired on the hand-held terminal 5 from an external device via the Internet or the like. The processing section 11 specifies the type of the staying location by specifying the position matching the position of the staying location, from among the positions of locations related to the user and positions of the facilities. For example, at step S27 described above, the staying location is specified as the workplace, and, at step S31 described above, the staying location is specified as the gymnasium. When the type of the staying location cannot be specified, the processing section 11 judges that the second condition is not satisfied.

Next, the processing section 11 judges whether or not the specified staying location is a location where the activity information is to be calculated. Here, the hand-held terminal 5 stores, in advance, the types of locations where the activity information is to be calculated. For example, in the present embodiment, some locations including the workplace are stored, but the gymnasium is not stored. The above described judgment is performed for determining whether or not the type of the specified staying location matches any of the types of locations stored in advance. When the specified staying location is judged to be a location where the activity information is to be calculated, the processing section 11 judges that the second condition is satisfied. On the other hand, when the specified staying location is judged not to be a location where the activity information is to be calculated, the processing section 11 judges that the second condition is not satisfied. For example, at step S27 described above, the workplace that is the staying location is judged to be a location where the activity information is to be calculated, and the second condition is judged to be satisfied. On the other hand, at step S31 described above, the gymnasium that is the staying location is judged not to be a location where the activity information is to be calculated, and the second condition is judged not to be satisfied. In another embodiment, the gymnasium may be registered as a location where the activity information is to be calculated such that the activity information is calculated in response to the user staying at the gymnasium.

As described above, in the present embodiment, the judgment of whether or not to calculate the activity information is performed on the basis of the positional information (positional information acquired at step S51 and stored in the memory). Here, in another embodiment, the judgment may be performed on the basis of other information. For example, in another embodiment, the judgment may be performed on the basis of the schedule information of the user. For example, when an end time of work is registered in the schedule information, the hand-held terminal 5 may judge to calculate the activity information in response to arrival of the end time.

When the judgment result at step S52 is positive, the process at step S53 is executed. On the other hand, when the judgment result at step S52 is negative, the process at step S51 is executed once again. More specifically, until the condition is judged to be satisfied at step S52, the processing section 11 repeats the processes at steps S51 and S52. It should be noted that the process loop of steps S51 and S52 is repeatedly executed at a rate of, for example, once every predetermined time period.

At step S53, the processing section 11 calculates the activity information. FIG. 13 shows one example of the activity information calculated in the present embodiment. FIG. 13 shows a series of activity information calculated when the user conducts the behaviors shown in FIG. 10. As shown in FIG. 13, in the present embodiment, the activity information includes activity content and activity level. In addition, as described above, in the present embodiment, the processing section 11 can calculate activity information indicating movement and activity information indicating an activity (e.g., work) in accordance with the location.

Here, when the first condition is satisfied at step S52, the processing section 11 calculates the activity information indicating movement (activity information of (a), (c), and (d) in FIG. 13). In the present embodiment, the activity information indicating movement shows a movement method as the activity content, and a movement amount as the activity level. More specifically, the processing section 11 calculates a movement speed and a movement pathway from the positional information sensed during the movement, and specifies the movement method on the basis of the movement speed and the movement pathway. For example, when the movement speed is lower than a predetermined speed, the movement method is specified as walking. In addition, when the movement speed is equal to or higher than the predetermined speed and the movement pathway is on a road, the movement method is specified as automobile (motorbike). Furthermore, when the movement speed is equal to or higher than the predetermined speed and the movement pathway is on a railroad track, the movement method is specified as train.

It should be noted that when the movement speed changes during movement, multiple types of movement methods may be specified. For example, when the movement speed is lower than the predetermined speed at the beginning of the movement and changes to equal to or higher than the predetermined speed part way through, the movement method may be specified as walking and automobile (or train). In this case, the processing section 11 may calculate two types of activity information, i.e., activity information in which the movement method is walking and activity information in which the movement method is automobile (or train).

In addition, the processing section 11 can calculate, as the movement amount, moving hours based on clock time information corresponding to the positional information acquired during movement. In another embodiment, the processing section 11 may calculate, as the movement amount, a moved distance on the basis of the movement pathway.

When the second condition is satisfied at step S52, the activity information (activity information of (b) in FIG. 13) indicating the activity in accordance with the location is calculated. "Activity in accordance with the location" is an activity that can be estimated from the staying location of the user, and examples thereof include "work" when the staying location is the workplace and "meal" when the staying location is a restaurant.

As shown in FIG. 13, similarly to the activity information indicating movement, the activity information indicating activity in accordance with the location also includes activity content and activity level (active hours). The activity content is calculated on the basis of the staying location. Specifically, the hand-held terminal 5 stores a table in which staying location (e.g., workplace) and the activity content (e.g., work) are associated, and specifies the activity content by using the table. Thus, for example, in a case where "workplace" as the staying location and "work" as the activity content are associated in the table, when the staying location is specified as workplace at step S27 described above, the activity content is specified as work.

The active hours can be calculated as, for example, the duration of stay at the staying location. This duration can be calculated on the basis of clock time information corresponding to the positional information acquired while staying at the staying location.

In the manner described above, the activity information is calculated at step S53. In a single process at step S53, a single set of activity information is calculated and stored in the memory of the processing section 11.

At step S54, the processing section 11 transmits, to the server 3, the activity information calculated at step S53. More specifically, the processing section 11 transmits the activity information stored in the memory to the server 3 by the communication section 10.

After step S54, the processing section 11 executes the process at step S51 once again. Subsequently, until the operation mode is altered to the OFF-mode, the processing section 11 repeatedly executes the processes at steps S51 to S54. As a result, the activity information is calculated at a predetermined timing (e.g., steps S22, S27, S29, and S33 shown in FIG. 11) in a single day, and is transmitted to the server 3.

(Environmental Information Calculation Process)

Figure 14:
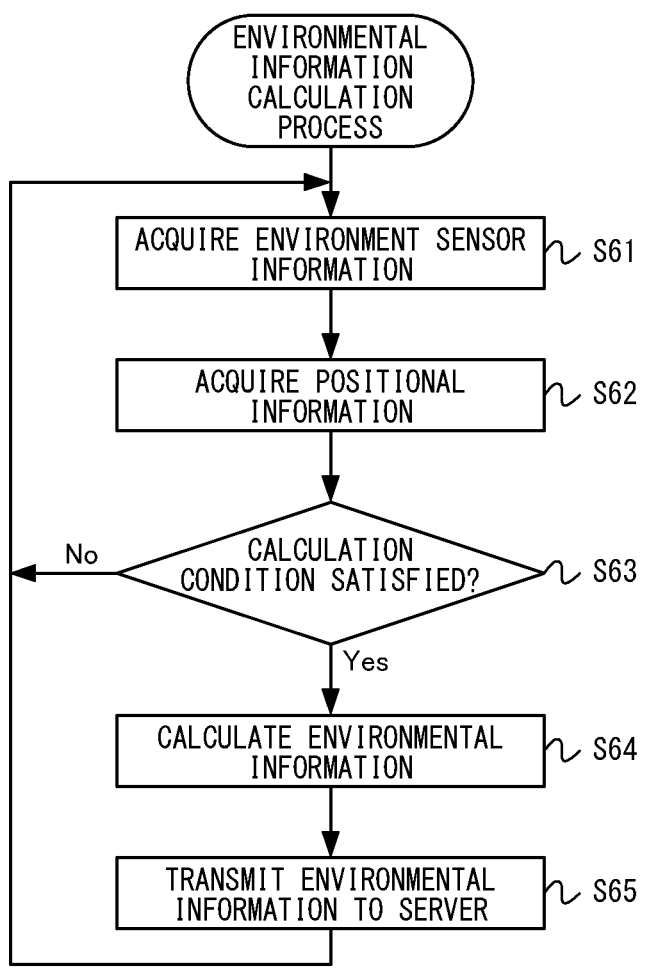
FIG. 14 is a flowchart showing a non-limiting example of the flow of an environmental information calculation process.

FIG. 14 is a flowchart showing one example of the flow of the environmental information calculation process. The environmental information calculation process is a process of calculating the environmental information indicating the environment surrounding the user on the basis of the environment sensor information (ambient temperature and humidity). In the present embodiment, the environmental information calculation process is continuously executed in the ON-mode. More specifically, in response to the operation mode of the hand-held terminal 5 being set to the ON-mode, the CPU of the processing section 11 initiates execution of a program for the environmental information calculation process, and continuously executes the environmental information calculation process until the operation mode is set to the OFF-mode.

First, at step S61, the processing section 11 acquires the environment sensor information as the information used for calculating the environmental information. More specifically, the processing section 11 acquires, as the environment sensor information from the environment sensor 14, temperature information sensed by the temperature sensor, and humidity information sensed by the humidity sensor. The acquired environment sensor information is stored in the memory of the processing section 11.

At step S62, the processing section 11 acquires positional information as information for performing a judgment of whether or not to calculate the environmental information. The process at step S62 is similar to the process at step S51 described above for acquiring the positional information. Thus, the processing section 11 may omit step S62, and use the positional information acquired at step S51 and stored in the memory.

At step S63, the processing section 11 judges whether or not a condition to calculate the environmental information has been satisfied. As described above, in the present embodiment, the environmental information is calculated at a timing when the activity information is calculated (see steps S22, S27, S29, and S33 shown in FIG. 11). Thus, the judgment at step S63 can be performed depending on whether or not the activity information has been calculated. When the judgment result at step S63 is positive, the process at step S64 is executed. On the other hand, when the judgment result at step S63 is negative, the process at step S61 is executed once again. More specifically, until the condition is judged to be satisfied at step S63, the processing section 11 repeats the processes at steps S61 to S63. It should be noted that the process loop of steps S61 to S63 is repeatedly executed at a rate of, for example, once every predetermined time period (possibly at a rate identical to that for the process loop of steps S51 and S52).

At step S64, the processing section 11 calculates the environmental information based on the environment sensor information calculated at step S61. FIG. 15 shows one example of the environmental information calculated in the present embodiment. FIG. 15 shows a series of environmental information calculated when the user conducts the behaviors shown in FIG. 10. As shown in FIG. 15, in the present embodiment, the environmental information includes activity content and environmental values.

The activity content included in the environmental information is identical to the activity content included in the activity information corresponding to the environmental information (see FIG. 15). In the present embodiment, the environmental information indicating the environment in which the user performs the activity indicated by the activity information is calculated. In other words, the activity content included in the environmental information indicates the activity of the user in a period in which the environment sensor information is sensed. At step S64, the processing section 11 sets the activity content calculated at step S53 as the activity content of the environmental information.

The environmental values included in the environmental information show values calculated from the environment sensor information acquired in the active period related to the activity content associated with the environmental values. In the present embodiment, the environmental values are each an average value of each of the indices (ambient temperature and humidity) indicated by the environment sensor information in the active period (see FIG. 15). More specifically, the processing section 11 first specifies the active period on the basis of the activity information. The active period can be specified on the basis of clock time information of a time point when the activity indicated by the activity information has started, and clock time information at a time point when the activity has ended. Next, the processing section 11 reads, from the memory, multiple sets of the environment sensor information acquired during the active period, calculates an average value of ambient temperature included in each set of the environment sensor information, and calculates an average value of humidity included in each set of the environment sensor information. The environmental values are not limited to averages of ambient temperature and humidity, and may be any value calculated from the environment sensor information. For example, if a heat index number (Wet Bulb Globe Temperature (WBGT)) can be calculated from the environment sensor information, the heat index number may be calculated as an environmental value.

In another embodiment, the environmental information may include history information of each set of the environment sensor information acquired during the active period instead the environmental values (or in addition to the environmental values). The history information may include all the sets of the environment sensor information acquired during the active period, or may include one portion of the sets of the environment sensor information (e.g., environment sensor information culled to represent one set per predetermined time period). When the environmental information includes the history information, the server 3 can recognize a change in the environment (temperature, humidity, etc.) during the active period. In addition, when the evaluation result based on the environmental information is to be presented to the user, the server 3 may present the user with the change in the environment during the active period. For example, when the evaluation result (e.g., image shown in FIG. 25) is displayed on the hand-held terminal 5, information based on the history information (e.g., line graph representing the history information) may be displayed on the hand-held terminal 5 in response to a predetermined instruction given by the user (e.g., in response to an input is made with respect to a detail button 56 shown in FIG. 25).

The environmental information may be any information representing the environment surrounding the user. More specifically, in another embodiment, the hand-held terminal 5 may acquire weather information regarding the weather and include that in the environmental information. The weather information may be acquired from, for example, an external device via the Internet. In addition, for example the hand-held terminal 5 may include an air pressure sensor, and may generate environmental information on the basis of air pressure information sensed by the air pressure sensor. The hand-held terminal 5 may include an illumination sensor, and may generate environmental information on the basis of the illumination information sensed by the illumination sensor. Furthermore, for example, the hand-held terminal 5 may sense noise by the microphone, and may generate environmental information on the basis of the sensed noise. In such manner, the environmental information may indicate at least one of ambient temperature, humidity, weather, atmospheric pressure, brightness, and noise of the location where the user is present.

In the manner described above, the environmental information including the activity content and the environmental values is generated at step S64. As a result, for example, environmental information (environmental information of (a), (c), and (d) shown in FIG. 15) indicating the environment while the user is moving and environmental information ((b) shown in FIG. 15) indicating the environment of a period in which the user is performing a specific activity (e.g., work) are calculated. In a single process at step S64, a single set of the environmental information is calculated and stored in the memory of the processing section 11.

Although details will be described later, in the present embodiment, the activity information is used when calculating an environmental index based on the environmental information on the server 3. Thus, in the present embodiment, for the purpose of calculating the environmental information in addition to calculating the activity information, the processing section 11 calculates the environmental information under a condition that the activity information has been calculated (step S63). Furthermore, the processing section 11 calculates the environmental information on the basis of the environment sensor information acquired during the active period corresponding to the activity information (step S64).

In another embodiment, the condition to calculate the environmental information may be any condition, and is not limited to a condition related to the activity information. In addition, the period in which the environmental information is to be calculated may be any period, and is not limited to the active period. For example, in another embodiment, the hand-held terminal 5 may calculate the environmental information in a period from a predetermined start time to a predetermined end time (on the basis of the environment sensor information acquired during this period), under a condition that the end time has arrived.

In another embodiment, the hand-held terminal 5 may judge whether or not to calculate the environmental information on the basis of the positional information sensed by the position sensing section 13. For example, the hand-held terminal 5 may determine the positional information on the basis of the user leaving and returning home, and calculate the environmental information for a home-away period (period between leaving home and returning home). In this case, the environmental information may be calculated under a condition that the user has returned home.

In another embodiment, the hand-held terminal 5 may judge whether or not to calculate the environmental information on the basis of the schedule information of the user. For example, when the start time and end time of work are registered in the schedule information, the hand-held terminal 5 may calculate the environmental information with respect to a period from the start time to the end time. In this case, the environmental information may be calculated under a condition that the end time has arrived.

At step S65, the processing section 11 transmits the environmental information calculated at step S64 described above to the server 3. More specifically, the processing section 11 transmits the environmental information stored in the memory to the server 3 by the communication section 10.

After step S65, the processing section 11 executes the process at step S61 once again. Subsequently, until the operation mode is altered to the OFF-mode, the processing section 11 repeatedly executes the processes at steps S61 to S65. As a result, the environmental information is calculated at a predetermined timing (e.g., steps S22, S27, S29, and S33 shown in FIG. 10) in a single day, and is transmitted to the server 3.

(Emotion Information Calculation Process)

Figure 16:
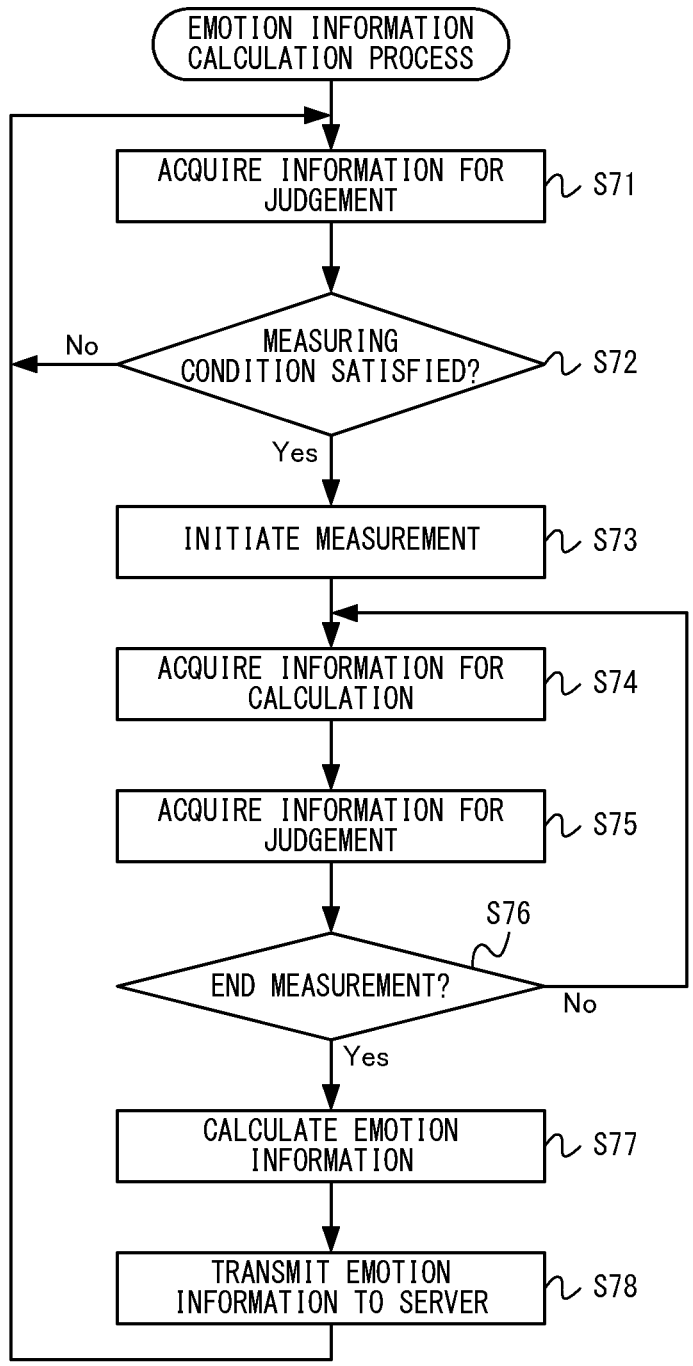
FIG. 16 is a flowchart showing a non-limiting example of the flow of an emotion information calculation process.

FIG. 16 is a flowchart showing one example of the flow of the emotion information calculation process. The emotion information calculation process is a process of calculating the emotion information indicating the emotion of the user on the basis of voice around the hand-held terminal 5 (voice of the user himself/herself and/or voice of a conversation partner) or facial expression of the user. In the present embodiment, the emotion information calculation process shown in the following is continuously executed in the ON-mode of the hand-held terminal 5. More specifically, in response to the operation mode of the hand-held terminal 5 being set to the ON-mode, the CPU of the processing section 11 initiates execution of a program for the emotion information calculation process, and continuously executes the emotion information calculation process until the operation mode is set to the OFF-mode.

As a result, in the present embodiment, the emotion information is sometimes calculated also in a standby state of the hand-held terminal 5 (a state in which the display 17 of the hand-held terminal 5 is turned OFF). In addition, also while the user is operating the hand-held terminal 5 and an application other than the program for the emotion information calculation process is executed (in the background of the other application), the emotion information is calculated.

First, at step S71, the processing section 11 acquires information for judging whether or not to initiate measurement of information used for calculating the emotion information. In the present embodiment, for the purpose of calculating the emotion information, sound sensed by the microphone 15 and image captured by the camera 16 are used. However, the sensing by the microphone 15 and the camera 16 sometimes cannot be performed properly depending on the status of the hand-held terminal 5, and the emotion cannot be calculated correctly in some cases. For example, in a situation where the hand-held terminal 5 is placed in a bag or a pocket of the user, voice or the like of the user is possibly not sensed properly by the microphone 15 because of more noises. Furthermore, in a situation where the user is not emitting any voices, the information used for calculating the emotion information cannot be obtained. Furthermore, in a situation where the hand-held terminal 5 is placed in a bag or pocket of the user or placed on a desk, image of the face of the user conceivably cannot be captured by the camera 16.

Thus, in the present embodiment, the hand-held terminal 5 performs the measurement by the microphone 15 and the camera 16 in an appropriate situation (in a situation where the emotion information can be calculated with a certain degree of accuracy). More specifically, the sensing by the microphone 15 and the image capturing by the camera 16 are not constantly executed in the ON-mode, and are initiated in response to satisfying of a predetermined measuring condition. The process at step S71 is a process of acquiring information for judging this measuring condition. Specifically, the processing section 11 acquires the schedule information described above and operation information indicating an operation with respect to the hand-held terminal 5. The schedule information is acquired from the storage section (memory or the like) of the hand-held terminal 5. The operation information is acquired from the operation input section 12.

At step S72, the processing section 11 judges whether or not the measuring condition is satisfied. In the present embodiment, the measuring condition is satisfying of at least one of a condition (microphone condition) for initiating measurement by the microphone 15 and a condition (camera condition) for initiating measurement by the camera 16. The microphone condition is, for example, initiation of a predetermined event. The predetermined event may be, other than "meeting" described above, for example, meal, work, movement, or the like. Here, one or more types of events including "meeting" are predetermined as the predetermined event. In the present embodiment, the microphone condition is judged on the basis of the schedule information. More specifically, the processing section 11 refers to the schedule information acquired at step S71, and judges whether or not a clock time for starting any one of the predetermined events determined in advance has arrived. The processing section 11 judges that the microphone condition is satisfied when a clock time for starting an event has arrived, and judges that the microphone condition is not satisfied when a clock time for starting an event has not arrived.

As described above, in the present embodiment, the judgment of whether or not a predetermined event has started is performed on the basis of the schedule information. In another embodiment, the judgment may be performed on the basis of other information. For example, in another embodiment, the processing section 11 may perform the judgment on the basis of the positional information (and/or the activity information calculated from the positional information). For example, the processing section 11 may judge that a "meal" event has started, when the processing section 11 determines that the user has entered a restaurant on the basis of the positional information, or when activity information indicating "meal" is calculated.

In another embodiment, the hand-held terminal 5 may perform measurement by the microphone 15 in a period in which the user is making a telephone call by using the hand-held terminal 5. More specifically, the processing section 11 may use, as the microphone condition, the start of a telephone call on the hand-held terminal 5. At this moment, at step S76 described later, the processing section 11 may judge to end the measurement under a condition that the telephone call has ended on the hand-held terminal 5. With this, the hand-held terminal 5 can detect the voice of the user in a period in which the user is making a telephone call on the hand-held terminal 5, and can determine the emotion in this period.

In addition, the camera condition is the start of an operation with respect to the hand-held terminal 5 by the user. The camera condition is judged on the basis of the operation information. More specifically, the processing section 11 judges whether or not any operation has been executed with respect to the hand-held terminal 5, on the basis of the operation information. The processing section 11 judges that the camera condition is satisfied when some operation is executed with respect to the hand-held terminal 5, and judges that the camera condition is not satisfied when an operation is not executed with respect to the hand-held terminal 5. It should be noted that the camera condition may be any condition enabling determination of the user viewing the hand-held terminal 5 (in other words, the user being included in an image capturing range of the camera). For example, in another embodiment, the camera condition may be the start of a predetermined information processing (e.g., video reproduction process) on the hand-held terminal 5. At this moment, at step S76 described later, the processing section 11 may judge to end the measurement under a condition that reproduction of a video has ended.

In another embodiment, the processing section 11 may prevents a condition from being determined as satisfied, in response to an incorrect operation (e.g., when the user not intendedly touches a button on the hand-held terminal 5) and/or an operation for a short period of time (e.g., when the user performs an operation on the hand-held terminal 5 to simple see the current time). More specifically, the processing section 11 may judge that the camera condition is satisfied when an operation is performed for a predetermined number of times or more in a predetermined period, and may judge that the camera condition is not satisfied when an operation has not been performed for a predetermined number of times for a predetermined period.

When the judgment result at step S72 is positive, the process at step S73 is executed. On the other hand, when the judgment result at step S72 is negative, the process at step S71 is executed once again. More specifically, until the condition is judged to be satisfied at step S72, the processing section 11 repeats the processes at steps S71 and S72. It should be noted that the process loop of steps S71 and S72 is repeatedly executed at a rate of, for example, once every predetermined time period.

At step S73, the processing section 11 initiates measurement for calculating the emotion information. More specifically, At step S72, when the microphone condition is satisfied, the processing section 11 turns ON the microphone 15, and initiates sensing by the microphone 15. Furthermore, when the camera condition is satisfied, the processing section 11 turns ON the camera 16, and initiates sensing (image capturing) by the camera 16.

At step S74, the processing section 11 acquires information for calculating the emotion information. More specifically, when the measurement by the microphone 15 is being performed, the processing section 11 acquires sound data sensed by the microphone 15, and stores the sound data in the memory. In addition, when measurement by the camera 16 is being performed, the processing section 11 acquires data of image captured by the camera 16, and stores the data in the memory. In the present embodiment, the sound data or image (video) data acquired in the measurement period (a period from the start of the process at step S74 to the end of the measurement at step S77 described later) is accumulated in the memory, and the emotion information is calculated by using the accumulated data after the measurement period has ended (step S77 described later).

At step S75, the processing section 11 acquires information for judging whether or not to end the measurement of the information used for calculating the emotion information. More specifically, when sensing by the microphone 15 is being performed, the processing section 11 acquires the schedule information. Furthermore, when sensing by the camera 16 is performed, the processing section 11 acquires the operation information.

At step S76, the processing section 11 judges whether or not to end the measurement. More specifically, when sensing by the microphone 15 is being performed, the processing section 11 judges whether or not the predetermined event, judged to have started at step S72, has ended. Thus, the processing section 11 refers to the schedule information acquired at step S75, and judges whether or not a clock time when the predetermined event is to be ended has arrived. The processing section 11 judges to end the measurement when the clock time at which the event is to be ended has arrived. On the other hand, the processing section 11 judges not to end (judges to continue) the measurement when the clock time at which the event is to be ended has not arrived.

As described above, in the present embodiment, judgment of whether or not to perform sensing by the microphone 15 is conducted depending on whether or not the current time is in a period of a predetermined event. In another embodiment, the judgment may be performed depending on whether or not the user is moving. For example, when the hand-held terminal 5 has a sensor capable of sensing motion (acceleration sensor, etc.), the hand-held terminal 5 judges whether or not the user is in motion on foot on the basis of the sensing result from the acceleration sensor, and, when the user is in motion on foot, may suspend the sensing by the microphone 15. This is because, when the user is in motion on foot, the hand-held terminal 5 is envisioned to be placed in a bag or a pocket of the user, and sensing the voice of the user accurately is difficult.

When sensing by the camera 16 is performed, the processing section 11 judges whether or not an operation of the user with respect to the hand-held terminal 5 has ended. This judgment is conducted, for example, depending on whether or not an operation has not been performed with respect to the hand-held terminal 5 in a predetermined time period. The processing section 11 judges to end the measurement when an operation with respect to the hand-held terminal 5 is judged to have ended. On the other hand, the processing section 11 judges not to end (to continue) the measurement when the operation with respect to the hand-held terminal 5 is judged not to have ended.

As described above, in the present embodiment, the sensing by the camera 16 is performed in a period in which an operation is performed with respect to the hand-held terminal 5. In another embodiment, the judgment of whether or not the current time is in the period described above may be performed on the basis of, not the operation information, but other information. For example, when the hand-held terminal 5 has a function of turning OFF the display 17 in a period where an operation is not performed and turning ON the display 17 in response to performing of an operation, the judgment described above may be performed depending on whether or not the display 17 is turned ON. Furthermore, the judgment may be performed depending on whether or not a predetermined application has been started up on the hand-held terminal 5.

When the judgment result at step S76 is positive, the process at step S77 is executed. On the other hand, when the judgment result at step S76 is negative, the process at step S74 is executed once again. More specifically, the processing section 11 repeats the processes at steps S74 to S76 until the judgment to end the measurement is made at step S76. It should be noted that the process loop of steps S74 to S76 is repeatedly executed at a rate of, for example, once every predetermined time period.

At step S77, the processing section 11 ends the sensing (measurement) by the microphone 15 or the camera 16, and calculates the emotion information. More specifically, when a sound sensed by the microphone 15 is acquired in the process at the immediately preceding step S74, the processing section 11 calculates the emotion information by using the sound sensed during the measurement period (i.e., on the basis of voices of the user and person in the surrounding area). Furthermore, when an image captured by the camera 16 has been acquired in the process at the immediately preceding step S74, the processing section 11 calculates the emotion information by using the image captured during the measurement period (i.e., on the basis of facial expression of the user).

First, one example of the method for calculating the emotion information by using sound sensed by the microphone 15 will be described. In the present embodiment, first, the processing section 11 identifies the voice of the user and the voice of a person (conversation partner) other than the user in signals of sound sensed during the measurement period. The method for identifying voice of the user and a conversation partner may be a conventional voice identification technology, and may be performed in the following manner, for example. More specifically, the processing section 11 removes a silent segment and a segment in which determination of emotion is difficult (e.g., a segment with many noises, a segment in which multiple voices overlap each other) in signals of sound measured during the measurement period. Then, the processing section 11 judges whether or not there is any segment containing the voice of the user in remaining voice segments. This judgment can be performed by registering (storing) the voice of the user in the hand-held terminal 5 in advance, and comparing the preregistered user voice and a voice in the remaining voice segments. For example, the processing section 11 may calculate a similarity for predetermined characteristic amounts related to both voices for each unit segment, and assess that the unit segment contains the voice of the user if the similarity is not lower than a predetermined threshold or assess that the unit segment contains a voice of a conversation partner if the similarity is lower than a predetermined threshold. As a result, from the signals of sound measured during the measurement period, a segment containing the voice of the user (user voice segment) and a segment containing a voice of the conversation partner (partner voice segment) can be extracted.

Next, the processing section 11 determines the emotion of the user on the basis of the extracted voice of the user. Any method may be used as the method for determining the emotion on the basis of the voice of the user, and a conventional emotion distinguishing method may be used. In the present embodiment, for example, the determination of the emotion is performed by the following method. Specifically, the processing section 11 calculates the characteristic amounts for each predetermined unit segment by using voice signals in the user voice segment. As the characteristic amounts, for example, intensity, tempo, and intonation are calculated. The intensity can be calculated as an average of the magnitude of amplitude in a predetermined segment. The tempo can be obtained by calculating the number of phonemes in a unit of time. The intonation can be obtained by detecting delimiters of a text, and detecting a specific intensity change pattern for a voice within the delimiters.

The processing section 11 calculates indices indicating the emotion on the basis of the calculated characteristic amounts. In the present embodiment, the processing section 11 calculates an index for each of the three types of emotions of anger, joy, and sadness on the basis of the characteristic amounts. Since these emotions can be estimated from changes in the characteristic amounts, the processing section 11 calculates the changes in the characteristic amounts (intensity, tempo, and intonation), and calculates each of the indices on the basis of the change levels thereof. In the present embodiment, the hand-held terminal 5 stores a table showing a change pattern of each of the characteristic amount for each of the types of emotions (anger, joy, and sadness). The change pattern may be created from an experiment (i.e., on the basis of a result of actually sensing voices from multiple test subjects and calculating characteristic amounts). The processing section 11 compares a change pattern shown by the table and a change in the calculated characteristic amounts for each of the types of emotions, and calculates a similarity for each of the types of emotions. Each of the indices is calculated such that a value of an index becomes high for a type of emotion with a high similarity and a value of an index becomes low for a type of emotion with a low similarity. For example, indices of "anger: 80, joy: 10, sadness: 50" are calculated when the similarity is high between a change pattern shown in the table regarding "anger" and the changes in the calculated characteristic amounts, when the similarity is low between a change pattern shown in the table regarding "joy" and the changes in the calculated characteristic amounts, and when the similarity is at a moderate level between a change pattern shown in the table regarding "sadness" and the changes in the calculated characteristic amounts. In the manner described above, the indices indicating the emotion of the user based on the voice of the user are calculated.

In present embodiment, similarly to the voice of the user, the processing section 11 calculates the indices indicating the emotion by using the voice of the conversation partner. More specifically, the processing section 11 calculates the indices indicating the emotion of the conversation partner by using the same calculation method described above.

Here, from the emotion of the conversation partner, the emotion of the user himself/herself is possibly estimated. For example, when the conversation partner is angry, since the user is (or can be estimated to be) scolded, the user may conceivably carry the emotion of "hate (hatred)". Furthermore, when the conversation partner is joyful, the user may conceivably carry the emotion of "pleasure".

Thus, in the present embodiment, the processing section 11 calculates the indices indicating the emotion of the user on the basis of the emotion of the conversation partner. Specifically, indices indicating "hate" and "pleasure" of the user are each calculated in accordance with each of the indices of "anger" and "joy" calculated for the conversation partner. The index indicating hate of the user is calculated to be large when the numerical value of the index indicating anger of the conversation partner is large. Furthermore, the index indicating pleasure of the user is calculated to be large when the numerical value of the index indicating joy of the conversation partner is large. In the present embodiment, although the type of the emotion of the conversation partner and the type of emotion of the user calculated therefrom are different, in another embodiment, the type of the emotion of the conversation partner and the type of the emotion of the user calculated therefrom may be the same. For example, the processing section 11 may calculate (correct) the index indicating sadness of the user on the basis of the index indicating sadness of the conversation partner.

As described above, in the present embodiment, indices indicating five types of emotions of anger, joy, sadness, hate, and pleasure are calculated for each of the predetermined unit segments which are each a unit in which the characteristic amounts are calculated. The processing section 11 calculates the emotion information in a single measurement period on the basis of each of the indices in each of the unit segments. For example, in the present embodiment, the processing section 11 calculates an average value of each of the unit segments for each of the five types of the indices. The processing section 11 uses information including the average values of the calculated five types of indices as the emotion information. More specifically, in the present embodiment, the emotion information indicating the five types of the emotion is calculated.

It should be noted that the specific content of the emotion information is not limited to those described above, and may be any content. For example, in another embodiment, the emotion information may be information indicating some of the five types of the indices, or may indicate a type of emotion different from the five types (e.g., surprise, fear, affection, etc.). Furthermore, the emotion information is not limited to information indicating multiple numerical values, and may be information indicating a single type of numerical value. For example, the emotion information may be information indicating a scalar value that represents heightening (depression) of emotion. Furthermore, the emotion information may be information indicating two types of indices, i.e., an index representing the level of positive type emotions (joy, pleasure, etc.), and an index representing the level of negative type emotions (anger, sadness, etc.).

In another embodiment, the hand-held terminal 5 may determine the emotion of the user on the basis of sound (voice) of the surrounding area in addition to (or instead of) the voice of the user and the voice of the conversation partner. More specifically, the hand-held terminal 5 may determine the emotion (of the user) in accordance with the surrounding atmosphere of the user. For example, when the hand-held terminal 5 senses laughter in the surrounding area of the user, the hand-held terminal 5 may estimate that the user is in a pleasant environment and determine that the user is joyful (e.g., calculate the index indicating joy to be high). Furthermore, when the hand-held terminal 5 senses screaming or an angry roar in the surrounding area of the user, the hand-held terminal 5 may estimate that the user is in a tense environment and determine that the user is tense (e.g., calculate an index indicating tension to be high).

Next, one example of the method for calculating the emotion information by using an image captured by the camera 16 will be described. In the present embodiment, since the camera 16 is attached facing inward and capturing of an image by the camera 16 is performed when the hand-held terminal 5 is operated, the captured image conceivably contains the face of the user. First, the processing section 11 specifies some characteristic points of the face (e.g., eyes, mouth, eyebrows, and cheek bones) of the user with an image recognition process performed with respect to the image captured by the camera 16. The characteristic points may be calculated from a conventional image recognition process. Of the captured images acquired during the measurement period, the processing section 11 calculates each of the characteristic points in one or more captured images (all or some of the captured images that have been acquired) acquired in a predetermined time interval.

Next, the processing section 11 determines the emotion of the user on the basis of each of the characteristic points. In the present embodiment, the emotion is determined on the basis of the position of each of the characteristic points and changes in the characteristic points. Specifically, by capturing an image of the usual facial expression of the user by the camera 16 in advance, the hand-held terminal 5 registers the usual position of each of the characteristic points of the user in advance. The processing section 11 calculates change (change direction and change level) from ordinary times and the speed of the change for each of the calculated characteristic points.

Here, the hand-held terminal 5 stores in advance a table in which the change and change speed, and the type of emotion (anger, joy, or sadness) in that case are associated.

The table may be created from an experiment (i.e., on the basis of a result of actually calculating the change and change speed from an image of the face for each type of emotions in multiple test subjects). The processing section 11 refers to the table, and calculates an index representing an emotion in accordance with the change and change speed of each of the calculated characteristic points. Specifically, a similarity between the change and change speed of each of the calculated characteristic points and the change and change speed of each type of emotions shown in the table is calculated, and an index in accordance with the similarity is calculated for each type of emotions. For example, when the similarity for the emotion "anger" is calculated to be high, the index for anger is calculated to be high. As a result, even when the emotion is to be calculated on the basis of facial expression of the user, for example, indices of "anger: 80, joy: 10, sadness: 50" are calculated for each type of emotions, similarly to when calculating the emotion on the basis of voices.

In the manner described above, the three types of indices are calculated from the face of the user recognized from a single captured image. The processing section 11 calculates the emotion information in the measurement period on the basis of the three types of indices calculated for each captured image acquired in the predetermined time interval. For example, in the present embodiment, an average value of each of the three types of indices calculated in each of the captured images is calculated. The processing section 11 uses, as the emotion information, information including the average values of the three types of indices calculated in the manner described above. Thus, in the present embodiment, the emotion information indicating the three types of emotion is calculated.

As described above, in the present embodiment, when determining the emotion by using the captured image, the emotion information including indices for three types of emotions of "anger", "joy", and "sadness" is calculated. In another embodiment, the emotion information may indicate some of the three types of indices, or may indicate a type of emotion (e.g., hate, pleasure, surprise, fear, affection, etc.) different from the three types. For example, the five types of indices identical to when determining the emotion by using voices may be calculated. Similarly to using voices, also when using the captured image, the emotion information is not limited to information indicating multiple numerical values, and may be information indicating a single type of numerical value or information indicating two types of indices, i.e., an index representing the level of positive type emotions and an index representing the level of negative type emotions.

At step S78, the processing section 11 transmits the emotion information to the server 3. More specifically, the processing section 11 transmits the emotion information calculated at step S77 and stored in the memory to the server 3 by the communication section 10.

After step S78, the processing section 11 executes the process at step S71 once again. Subsequently, until the operation mode is altered to the OFF-mode, the processing section 11 repeatedly executes the processes at steps S71 to S78. With this, the emotion information is calculated in response to performing of a predetermined event of a single day (e.g., step S25 shown in FIG. 11) and is transmitted to the server 3.

In the present embodiment, after the predetermined event has ended, the hand-held terminal 5 calculates the emotion information indicating the emotion of the user in a period of the event. In another embodiment, the hand-held terminal 5 may successively calculate the emotion information during the event. For example, the hand-held terminal 5 may calculate the emotion information for each of the predetermined unit segments which are each a unit in which the characteristic amounts of the voice of the user is calculated. At this moment, the hand-held terminal 5 may successively transmit the calculated emotion information to the server 3. With this, the hand-held terminal 5 can calculate the emotion information in real time, and the server 3 can also provide, in real time, the user with a network service in accordance with an evaluation based on the emotion information.

(Other Example of Emotion Information Calculation Process)

Next, another example of the emotion information calculation process will be described. In the emotion information calculation process the present embodiment described above, for the purpose of performing the measurement by the microphone 15 and the camera 16 under a proper situation, the period in which a predetermined event is performed is specified on the basis of the schedule information, and measurement is performed in the specified period (step S72 to S76). In another embodiment, the period for sensing (measuring) the information for calculating the emotion information may be specified on the basis of other information. For example, the hand-held terminal 5 may, by intermittently performing sensing by using the microphone 15, specify the period in which the predetermined event is performed. In the following, as another one example of the emotion information calculation process, an example in which the sensing by the microphone 15 is performed intermittently will be described.

Figure 17:
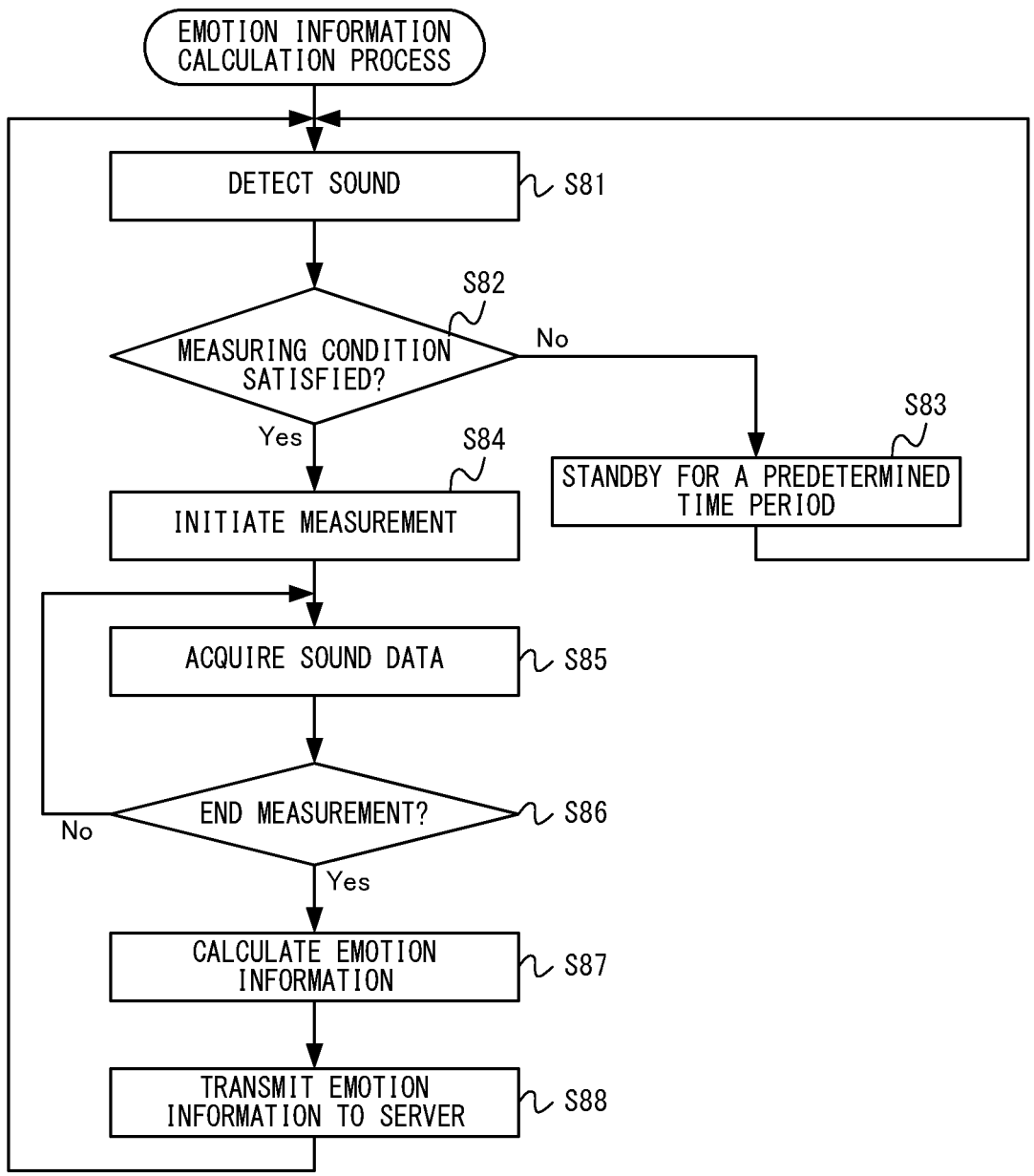
FIG. 17 is a flowchart showing another a non-limiting example the flow of the emotion information calculation process.

FIG. 17 is a flowchart showing another one example of the flow of the emotion information calculation process. Similarly to the process shown in FIG. 16, the process shown in FIG. 17 is continuously executed in the ON-mode of the hand-held terminal 5.

First, at step S81, the processing section 11 executes sensing by the microphone 15 for a predetermined time period. More specifically, the processing section 11 turns ON the microphone 15, performs sensing by the microphone 15 for the predetermined time period (e.g., three seconds), and then turns OFF the microphone 15. With this, the processing section 11 acquires sound for the length of the predetermined time period.

At step S82, the processing section 11 judges whether or not a measuring condition to initiate measurement for calculating the emotion information on the basis of the sensed sound acquired at step S81 is satisfied. Specifically, the processing section 11 judges whether or not a sound (e.g., the voice of the user or the voice of the conversation partner) to be used for calculating the emotion information is contained in the sensed sound. When the sound is contained, the measuring condition is judged to be satisfied, whereas, when the sound is not contained, the measuring condition is judged not to be satisfied. When the judgment result at step S82 is negative, the process at step S83 is executed. On the other hand, when the judgment result at step S82 is positive, a process at step S84 described later is executed.

At step S83, the processing section 11 stands by for a predetermined first time period (e.g., ten seconds). When the first time period elapses, the processing section 11 executes the process at step S81 once again. Thus, until the measuring condition is satisfied, the processing section 11 performs the sensing (step S81) by the microphone at a time interval equal to the first time period.

On the other hand, at step S84, the processing section 11 initiates the measurement for calculating the emotion information. The process at step S84 is similar to the process at step S73 described above.

At step S85, the processing section 11 acquires information for calculating the emotion information. More specifically, similarly to the process at step S74 when performing the measurement by the microphone 15, the processing section 11 acquires data of sound sensed by the microphone 15, and stores the data in the memory. At step S81 described above, although sound is intermittently sensed by the microphone 15, sound is continuously sensed at step S85.

At step S86, the processing section 11 judges whether or not to end the measurement. In the example shown in FIG. 17, this judgment is performed on the basis of sound sensed at step S85. Specifically, a judgment to end the measurement is made when a sound (the voice of the user or the voice of the conversation partner) to be used for calculating the emotion information is not contained in sound sensed in the past predetermined time period (e.g., one minute) from the present time. On the other hand, a judgment to not end the measurement is made when the sound to be used for calculating the emotion information is contained in the sound sensed in the past predetermined time period from the present time. When the judgment result at step S86 is positive, the process at step S87 is executed. On the other hand, when the judgment result at step S86 is negative, the process at step S85 is executed once again. Subsequently, the processes at steps S85 to S86 are repeatedly executed until the judgment to end the measurement is made at step S86. When the process loop of steps S85 to S86 is to be repeatedly executed, the processing section 11 acquires the sound sensed by the microphone 15 such that the sensed sound is temporally continuous. Thus, as a result of the process loop, sound is continuously sensed in the measurement period. However, in another embodiment, sound may be sensed in the measurement period intermittently with a time interval equal to a second time period that is shorter than the first time period.

At step S87, the processing section 11 calculates the emotion information. The process of calculating the emotion information at step S87 is similar to the process of calculating the emotion information on the basis of sound sensed by the microphone 15 at step S77 described above. However, in the example shown in FIG. 17, the length of the measurement period (period from the start of the process at step S84 to the end of the measurement at step S87) may not have a sufficient length for calculating the emotion information. Thus, the processing section 11 may skip calculating the emotion information when the length of the measurement period (in other words, the length of sound sensed in the measurement period) is shorter than a predetermined time period, and calculate the emotion information when the length of the measurement period is equal to or longer than the predetermined time period. In the following step S88, the processing section 11 transmits the emotion information to the server 3 similarly to step S78 described above.

After step S88, the processing section 11 executes the process at step S81 once again. Subsequently, until the operation mode is altered to the OFF-mode, the processing section 11 repeatedly executes the processes at steps S81 to S88. With this, measurement by the microphone 15 is executed in a period in which information (voice of the user, etc.) for calculating the emotion information can be sensed in a single day, and the emotion information is calculated for the period.

In the description above, the method for setting the measurement period of the microphone 15 in the case of calculating the emotion information by using the sound sensed by the microphone 15 has been described. Also in the case of calculating the emotion information by using an image captured by the camera 16, the measurement period (period for capturing an image) by the camera 16 can be set by using a method similar to the method shown in FIG. 17. More specifically, the processing section 11 acquires an image captured by the camera 16 at steps S81 and S85. In addition, at step S82, the processing section 11 judges whether or not the face of the user is included in a captured image. Furthermore, at step S86, the processing section 11 judges not to end the measurement when the face of the user is included in an image captured in the past predetermined time period from the present time, and judges to end the measurement when the face of the user is included in the captured image. In the manner described above, in the case of calculating the emotion information by using an image captured by the camera 16, the measurement period can be set in accordance with the period in which the emotion information can be calculated.

(Preference Information Calculation Process)

Figure 18:
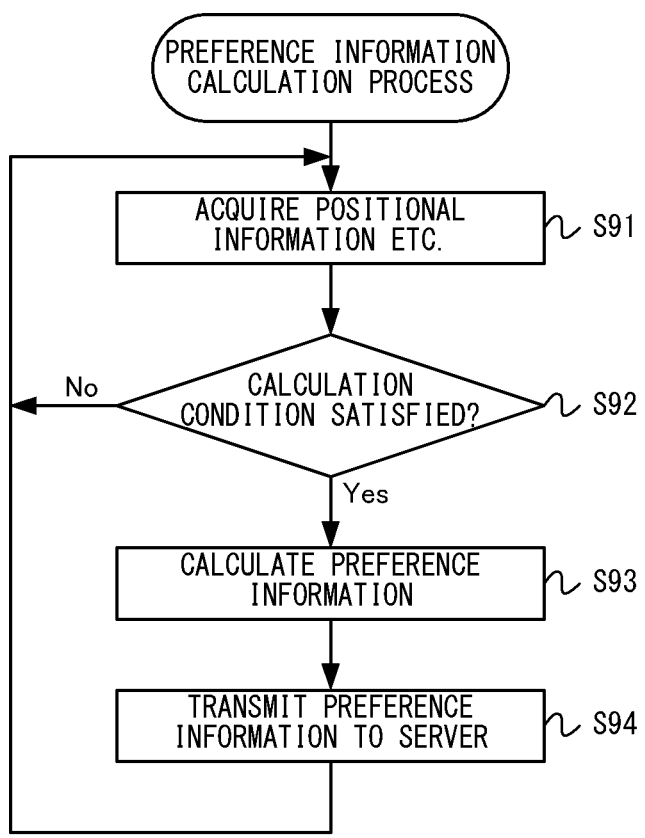
FIG. 18 is a flowchart showing a non-limiting example of the flow of a preference information calculation process.

FIG. 18 is a flowchart showing one example of the flow of the preference information calculation process. The preference information is a process of calculating preference information indicating the preference of the user on the basis of an input with respect to the hand-held terminal 5 by the user or the position (activity) of the user. In the present embodiment, the preference information calculation process is continuously executed in the ON-mode. More specifically, in response to the operation mode of the hand-held terminal 5 being set to the ON-mode, the CPU of the processing section 11 initiates execution of a program for the preference information calculation process, and continuously executes the preference information calculation process until the operation mode is set to the OFF-mode.

First, at step S91, the processing section 11 acquires information to be used for calculating the preference information. In the present embodiment, the processing section 11 acquires the positional information sensed by the position sensing section 13 and information inputted by the user (user input information) with respect to the operation input section 12. The acquired information is stored in the memory of the processing section 11.

At step S92, the processing section 11 judges whether or not a calculation condition to calculate the preference information is satisfied. The calculation condition includes a condition regarding position (position condition) and a condition regarding input of the user (user input condition). When either one of the position condition and the user input condition is satisfied, the calculation condition is judged to be satisfied.

In the present embodiment, the position condition is the user staying at a specific location where the preference information is to be calculated (location where the preference of the user can be estimated from the location). More specifically, the processing section 11 judges whether or not the user has stayed at a certain location on the basis of the position sensed by the position sensing section 13. This judgment can be performed similarly to the judgment for determining whether or not the second condition is satisfied as described in "(Activity Information Calculation Process)" above. When the user is judged to have stayed at a certain location, the processing section 11 specifies the type of staying location, and judges whether or not the preference information can be calculated for (the type of) the specified staying location. As described above, the hand-held terminal 5 stores, in advance, the table showing the association between location (facility) and genre indicated by the preference information. The processing section 11 judges whether or not the preference information can be calculated depending on whether or not the specified staying location is included in the table. When calculation of the preference information is judged to be possible, the processing section 11 judges that the position condition is satisfied. On the other hand, the processing section 11 judges that the position condition is not satisfied when (a) the user is judged not to have stayed at a certain location, (b) the specified staying location is not included in the table, or (c) the type of the staying location cannot be specified. For example, at step S31, since the user is determined to be staying at the gymnasium and the gymnasium is included in the table, the position condition is judged to be satisfied. On the other hand, at step S27, since the user is determined to be staying at the workplace and the workplace is not included in the table, the position condition is judged not to be satisfied.

The user input condition is an input of information from which the preference can be estimated. Specifically, in the present embodiment, when a specific search phrase with which estimation of the preference information is possible is inputted in a search engine website, the processing section 11 judges that the user input condition is satisfied. More specifically, when an input of a search phrase is included in the input acquired at step S91, the processing section 11 judges whether or not the search phrase enables calculation of the preference information, i.e., whether the search phrase is a word that enable estimation of the preference of the user. The hand-held terminal 5 stores a table showing the association between words and a genre of preference corresponding to the words (genre indicated by the preference information). The processing section 11 judges whether or not the inputted search phrase contains a word described in the table. When the inputted search phrase contains a word described in the table, the processing section 11 assesses that the preference information can be calculated from the inputted search phrase, and judges that the user input condition is satisfied. On the other hand, when the input acquired at step S91 does not contain an input of a search phrase, or when the inputted search phrase does not contain a word described in the table, the processing section 11 judges that the user input condition is not satisfied.

When the judgment result at step S92 is positive, the process at step S93 is executed. On the other hand, when the judgment result at step S92 is negative, the process at step S91 is executed once again. More specifically, the processing section 11 repeats the processes at steps S91 and S92 until the calculation condition is judged to be satisfied at step S92. It should be noted that the process loop of steps S91 and S92 is repeatedly executed at a rate of, for example, once every predetermined time period.

At step S93, the processing section 11 calculates the preference information. When the position condition is satisfied at step S92, the processing section 11 calculates the preference information on the basis of the positional information acquired at step S91 (more specifically, on the basis of the staying location calculated from the positional information). That is, the processing section 11 specifies the genre associated with the staying location specified from the positional information in the table showing the association between location and preference genre. The processing section 11 calculates the preference information indicating the specified genre.

When the user input condition is satisfied at step S92, the processing section 11 calculates the preference information on the basis of the user input information acquired at step S91. That is, the processing section 11 specifies the genre associated with the word contained in the search phrase specified from the user input information in the table showing the association between words and preference genre. The processing section 11 calculates the preference information indicating the specified genre.

In the manner described above, preference information is calculated at step S93. In a single process of step S93, a single set of the preference information is calculated and stored in the memory of the processing section 11.

At step S94, the processing section 11 transmits the preference information calculated at step S93 to the server 3. More specifically, the processing section 11 transmits, to the server 3 by the communication section 10, the preference information stored in the memory.

As described above, in the present embodiment, the preference information is calculated on the basis of the positional information. In another embodiment, the preference information may be calculated on the basis of the activity information. More specifically, the hand-held terminal 5 may calculate the activity information (e.g., activity information indicating that physical exercise has been conducted at the gymnasium) from positional information, and calculate the preference information on the basis of the activity information.

In the present embodiment, the hand-held terminal 5 calculates the preference information on the basis of a search phrase inputted on a search engine website. In another embodiment, the preference information may be calculated on the basis of another user input information. For example, when the user performs an input for browsing a web page, the hand-held terminal 5 may determine the preference of the user on the basis of the content of the web page (e.g., keywords in the web page). For example, when a so-called a "Like" button is pressed on an SNS (social networking service) web page, the hand-held terminal 5 may determine the preference of the user on the basis of the content of the web page.

In another embodiment, the preference information may be calculated on the basis of information other those described above. For example, the preference information may be calculated on the basis of profile information (age, whether having a child or not, marital status, family composition, gender, income, hobby, etc.) of the user stored in the hand-held terminal 5. In addition, the preference information may be calculated on the basis of an application executed on the hand-held terminal 5. For example, the hand-held terminal 5 can possibly determine the preference of the user (genre of interest of the user) on the basis of the type of application (e.g., game application, etc.) executed on the terminal itself (Information Presentation Process)

Figure 19:
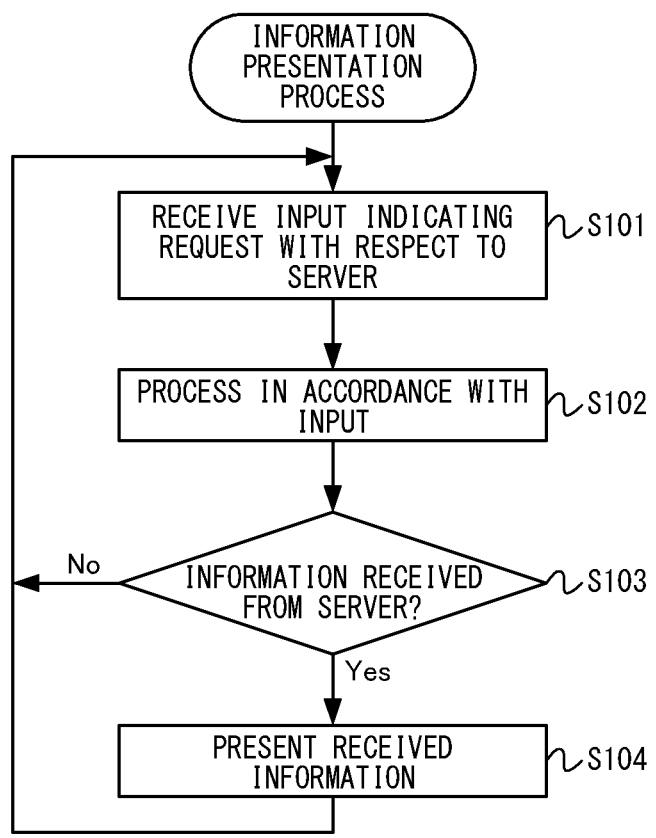
FIG. 19 is a flowchart showing one example of the flow of an information presentation process.

FIG. 19 is a flowchart showing one example of the flow of the information presentation process. The information presentation process is a process of presenting (outputting an image and/or sound) the user with information (information associated with network service) generated by the server 3. In the present embodiment, the information presentation process is continuously executed in the ON-mode. More specifically, in response to the operation mode of the hand-held terminal 5 being set to the ON-mode, the CPU of the processing section 11 initiates execution of a program for the information presentation process, and continuously executes the information presentation process until the operation mode is set to the OFF-mode.

First, at step S101, the processing section 11 receives an input from the user. More specifically, information indicating an input performed with respect to the operation input section 12 is acquired from the operation input section 12. In the present embodiment, the server 3 manages a website for providing a network service. The user can, by accessing this web site by using the hand-held terminal 5, browse the evaluation result by the server 3, and make a purchase of a commodity or the like related to the recommendation information presented by the server 3. In step S101 described above, the processing section 11 receives an input for making various types of requests to the website. Examples of the requests include a request to login to the website, a request to browse a web page in the website (including a page showing the evaluation result, and a page for purchasing a commodity or the like), and a request to purchase a commodity or the like. The program for executing the information presentation process may be a part of a dedicated application for receiving the network service by the server 3, or a part of a widely used browser application for browsing a web page.

At step S102, the processing section 11 executes a process in accordance with the input received at step S101. For example, when a request of login to the website is made, the processing section 11 requests login to the server 3. For example, when a request to browse a web page in a website is made, the processing section 11 requests the server 3 to acquire the web page according to the request. Specifically, the processing section 11 causes the communication section 10 to transmit information indicating the request to the server 3.

In response to the request described above, the server 3 executes a process in accordance with the request (step S119 described later). For example, when a request of login is received, the server 3 transmits information of a login image (web page) to the hand-held terminal 5. Furthermore, for example, when a request to acquire a web page is received, the server 3 transmits information of the web page to the hand-held terminal 5.

The processes at steps S101 and S102 may be performed with a method similar to a conventional process for making various types of requests with respect to a server that provides web pages.

At step S103, the processing section 11 judges whether or not information related to the network service has been received from the server 3. The information received from the server 3 in the process at step S103 is information transmitted from the server 3 in response to the request at step S102, or information (i.e., service data) transmitted from the server 3 at a timing (step S36 shown in FIG. 11) when the server 3 provides the network service. When the judgment result at step S103 is positive, the process at step S104 is executed. On the other hand, when the judgment result at step S103 is negative, the process at step S101 is executed once again.

At step S104, the processing section 11 presents the user with the information received from the server 3. More specifically, on the basis of the information received from the server 3 by the communication section 10, the processing section 11 displays an image of a web page or the like on the display 17, or outputs audio from the loudspeaker 18. In another embodiment, the hand-held terminal 5 may include a vibration motor as an output device, and, in this case, the service data transmitted from the server 3 may contain content for controlling vibration of the hand-held terminal 5.

Thus, the hand-held terminal 5 may outputs image, sound, and/or vibration associated with the service data.

Next after step S104, the processing section 11 executes the process at step S101 once again. Subsequently, until the operation mode is altered to the OFF-mode, the processing section 11 repeatedly executes the processes at steps S101 to S104. With this, the user can browse information provided from the server 3 at a timing desired by the user in a single day, and information is provided from the server 3 to the hand-held terminal 5 through "push" at a predetermined timing (step S36 shown in FIG. 11) in a single day.

5. Operation on Server

Next, specific examples of processes executed on the server 3 will be described. As described above, the hand-held terminal 5 transmits various types of QOL factor information to the server 3. The server 3 evaluates the state (QOL, etc.) of the user on the basis of the QOL factor information, and provides a network service in accordance with the evaluation result. In the following, details of the processes executed on the server 3 will be described.

Figure 20:
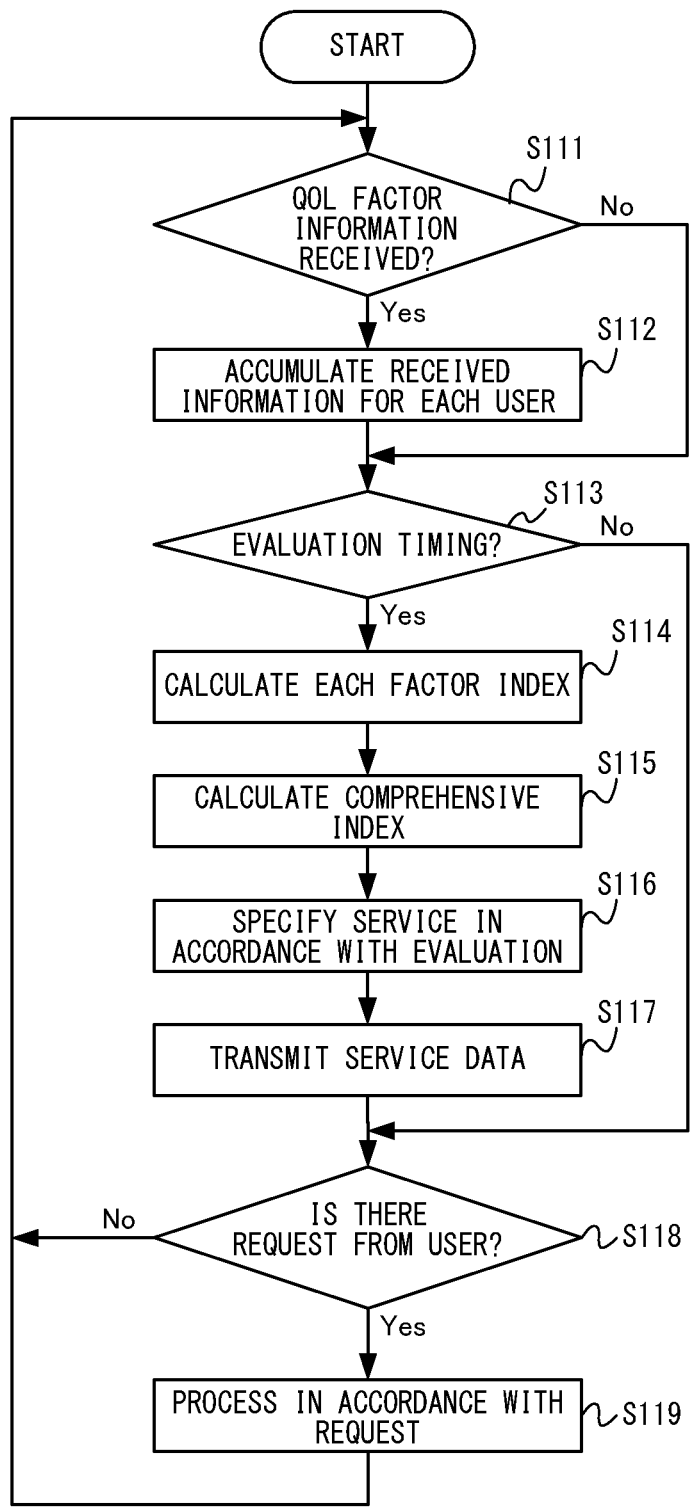
FIG. 20 is a flowchart showing a non-limiting example of the flow of processes executed on the server.

FIG. 20 is a flowchart showing one example of the flow of processes executed on the server. The flowchart shown in FIG. 20 is continuously executed regardless of the mode of the hand-held terminal 5 (i.e., regardless of being in the waking period or the sleeping period).

First, at step S111, the server 3 judges whether or not the QOL factor information has been received from the hand-held terminal 5. As described above, the hand-held terminal 5 transmits the QOL factor information to the server 3 at an appropriate timing (step S19 shown in FIG. 4, step S54 shown in FIG. 12, step S65 shown in FIG. 14, step S78 shown in FIG. 16, step S94 shown in FIG. 18). In response, the server 3 receives the QOL factor information from the hand-held terminal 5, and, at this moment, the judgment result at step S111 becomes positive. When the judgment result at step S111 is positive, the process at step S112 is executed. On the other hand, when the judgment result at step S111 is negative, the process at step S112 is skipped, and the process at step S113 described later is executed.

At step S112, the server 3 stores (accumulates) QOL factor information received from the hand-held terminal 5 for each user. More specifically, the server 3 updates, so as to include the received QOL factor information, the user data indicating various types of information related to the user. The user data stored in the server 3 will be described here.

Figure 21:
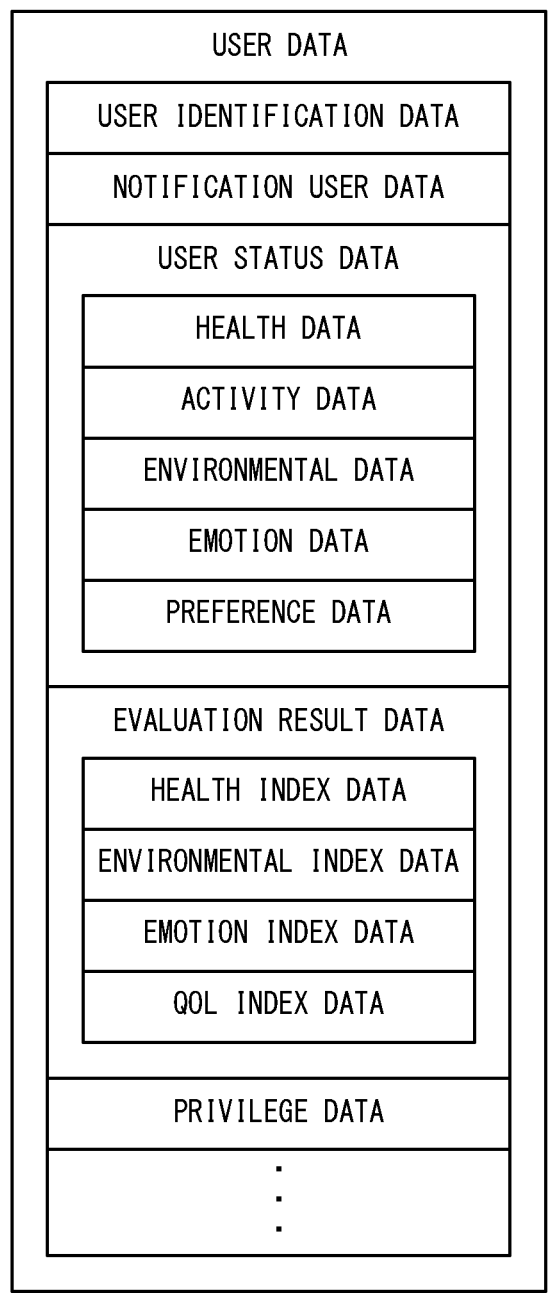
FIG. 21 shows one example of data organization of user data stored in the server in the present embodiment.

FIG. 21 shows one example of data organization of the user data stored in a memory on the server of the present embodiment. FIG. 21 shows the user data stored in the memory of the server 3 for a single user. Although not diagrammatically represented, the server 3 stores, in a predetermined storage section, data similar to the user data shown in FIG. 21 for each user on the network service.

As shown in FIG. 21, the user data contains user identification data, notification user data, user status data, evaluation result data, and privilege data. In the server 3, a set of these five types of data is accumulated for each user. It should be noted that the user data may contain data other these five types of data, or does not necessarily have to contain one portion of data among these five types of data.

The user identification data is data indicating identification information (ID, password, etc.) for identifying the user. In the present embodiment, in a predetermined registration process executed when initiating the network service for the user, the identification information is set and the user identification data indicating the set identification information is stored in the server 3.

The notification user data is data indicating another user (referred to as "notification-subject user") to which the evaluation result (or information based on that) related to the user indicated by the user identification data is presented. Specifically, the notification user data indicates identification information (e.g., ID) of the notification-subject user. As described above, in the present embodiment, service data associated with a network service in accordance with an evaluation result related to a certain user is transmitted to, other than the user (person himself/herself) who is the subject of evaluation, a terminal of another user. The notification user data indicates the other user to which the service data is to be transmitted. The notification-subject user does not necessarily have to be a user who can receive the network service. The notification user data may indicate information representing transmission destination to which the service data is to be transmitted (e.g., E-mail address or the like of a terminal used by the notification-subject user).

The user status data is data indicating various types of statuses of the user. As shown in FIG. 21, in the present embodiment, the user status data contains health data, activity data, environmental data, emotion data, and preference data.

The health data is data indicating the health information acquired from the hand-held terminal 5 of the user. The activity data is data indicating the activity information acquired from the hand-held terminal 5 of the user. The environmental data is data indicating the environmental information acquired from the hand-held terminal 5 of the user. The emotion data is data indicating the emotion information acquired from the hand-held terminal 5 of the user. These four types of data each include multiple sets of QOL factor information among the previously acquired QOL factor information. Specifically, in the present embodiment, for example, the four types of data indicate QOL factor information from the latest to those acquired in the past in a predetermined storage period (e.g., three months). Thus, when the health information, the activity information, the environmental information, or the emotion information is received at step S111, the server 3 updates, at step S112 and so as to include the received information, data corresponding to the received information among the four types of data.

The storage period regarding the four types of data is the same for the server 3. With this, the server 3 can perform an overall evaluation of the user on the basis of the QOL factor information in the storage period. In another embodiment, the storage period regarding the four types of data may be any length, or may be different among the four types of data.

The preference data is data indicating the preference information acquired from the hand-held terminal 5 of the user. In the present embodiment, the preference data indicates a genre, in which the user is interested, assessed on the basis of the previously acquired preference information. Specifically, the preference data indicates the presence or absence of interest of the user for each genre of preference described above.

Thus, when the preference information is received at step S111, the server 3 updates, at step S112, the preference data so as to have contents reflecting the received information. For example, when preference information indicating a certain genre has been acquired, the server 3 updates the preference data so to have content indicating interest in the genre, if necessary. The preference data may be generated on the basis of the previously acquired preference information, and the latest acquired preference information does not necessarily have to be reflected immediately. For example, when preference information indicating the same genre has been acquired for a predetermined number of times (e.g., five times) or more in a predetermined period of time (e.g., one month), the server 3 may update the preference data so as to have content indicating interest in the genre.

In another embodiment, similarly to the health data and the like, the preference data may indicate the preference information from the latest to those acquired in the past in a predetermined storage period (e.g., three months).

The server 3 may store, in addition to the user status data, information used for calculating the information representing the user status data. More specifically, the hand-held terminal 5 may transmit the information used for calculating the QOL factor information to the server 3 in addition to transmitting the QOL factor information, and the server 3 may store the received information. The information used for calculating the QOL factor information and stored in the server 3 may be presented to the user on the hand-held terminal 5 through, for example, the process at step S119 described later (process of transmitting information from the server 3 to the hand-held terminal 5).

Details of the evaluation result data and privilege data shown in FIG. 21 will be described later.

Returning to the description of FIG. 20, at step S113, the server 3 judges whether or not the evaluation timing has arrived. In the present embodiment, this judgment is performed depending on whether or not the predetermined clock time determined in advance has arrived. When the judgment result at step S113 is positive, the series of processes at step S114 to S117 is executed. On the other hand, when the judgment result at step S113 is negative, the series of processes at steps S114 to S117 is skipped, and the process at step S118 described later is executed.

At step S114, the server 3 performs an evaluation of the user on the basis of the QOL factor information acquired from the hand-held terminal 5. In the process at step S114, an evaluation is performed regarding health, environment, and emotion of the user. More specifically, the server 3 calculates three factor indices, i.e., the health index, the environmental index, and the emotion index. In the following, calculation methods of these factor indices will be described.

(Calculation of Health Index)

First, a specific example of a calculation method of the health index (evaluation method regarding health) will be described. In the present embodiment, the health index is calculated on the basis of health information acquired when the user is awake (health information corresponding to the sleeping period) and activity information acquired in the waking period of the user. More specifically, the server 3 first calculates the fatigue level in the waking period from the activity information (referred to as "second fatigue level" in distinction from the above described first fatigue level calculated from the biological information in the sleeping period), and calculates the health index on the basis of the calculated second fatigue level and the health information.

In the present embodiment, the server 3 stores, in advance, a table showing the association between a condition regarding the activity information and the change level of the second fatigue level, and calculates the second fatigue level by using the table. FIG. 22 shows one example of a table used for calculating the second fatigue level. As shown in FIG. 22, the table shows the association between a condition regarding the activity information, and the change level of the second fatigue level when the condition is satisfied. In the example shown in FIG. 22, the table associates a condition of the activity content being "work" and the activity level being "eight to ten hours" to a change level of the second fatigue level of "+10". This means that when activity information showing the activity content is "work" and the activity level is not less than eight hours but not less than ten hours is acquired, the second fatigue level is increased by 10. The table shown in FIG. 22 associates a condition of the activity content being "massage" but without the activity level being designated, to a change level of "−20". This means that when the activity content is "massage", the second fatigue level is lowered by 20. In the table described above, a condition that increases the second fatigue level and a condition that lowers the second fatigue level may both be included, or only either one of the two may be included.

The server 3 calculates the change level of the second fatigue level corresponding to the acquired activity information by referring to the table. For example, when activity information in which the activity content is "movement (walking)" and the activity level is "ten minutes" is acquired, the server 3 calculates "+10" as the change level of the second fatigue level corresponding to this activity information. In the present embodiment, the server 3 calculates the change level corresponding to each set of activity information acquired in a predetermined period (in the present embodiment, today).

Furthermore, the server 3 calculates a final second fatigue level on the basis of a predetermined basic fatigue level (e.g., "0") and the change level of the calculated second fatigue level. Specifically, the final second fatigue level is calculated by making addition or subtraction in accordance with the change level of the second fatigue level with respect to the basic fatigue level. For example, in a case where the basic fatigue level is "0", when the change level is calculated as "+10", "+15", and "−10", the final second fatigue level is calculated as "+15". It should be noted that the server 3 may use the value the first fatigue level (fatigue index) indicated by the health information as the basic fatigue level.

When the second fatigue level is calculated, the server 3 calculates the health index on the basis of the second fatigue level and the health information. The health index is calculated in reflection of the values of the respective fatigue levels (first fatigue level and second fatigue level). For example, the health index is calculated such that the health index becomes larger when each of the fatigue levels (first fatigue level and second fatigue level) is smaller. In addition, the health index is calculated in reflection of the values of sleep indices indicated by the health information. For example, the health index is calculated such that the health index becomes higher when the sleep indices indicate that the quality of sleep is good. For example, the server 3 may calculate, as the overall fatigue level, a value obtained as a sum of the fatigue levels each assigned with a predetermined weight, and calculate the health index by making addition or subtraction in accordance with the sleep indices with respect to the calculated overall fatigue level. In the present embodiment, the health index is calculated as an integer from 0 to 100, and a larger numerical value of the health index represents being healthier.

In another embodiment, the health index may be calculated on the basis of other QOL factor information. For example, the health index may be calculated on the basis of the environmental information in addition to the activity information. More specifically, even when the activity information is the same content, the server 3 may calculate the health index with different values depending on the environmental information. For example, when the environmental information indicates that the environment is relatively not good for the user (e.g., when ambient temperature and humidity are too high), the server 3 may calculated the second fatigue level to be high when compared to a case in which the environmental information indicates that the environment is relatively good for the user (e.g., when ambient temperature and humidity are at suitable levels).

In another embodiment, the health index may be calculated on the basis of, in addition to the activity information, the preference information. For example, when activity information indicates physical exercise, the server 3 may calculate the value of the second fatigue level to be relatively low when the preference information indicates that the user has interest in physical exercise, or calculate the value of the second fatigue level to be relatively high when the preference information indicates that the user has no interest in physical exercise. In the present embodiment, although the preference information is not used for an evaluation regarding the user (calculation of QOL index), the preference information may be used for an evaluation regarding the user (calculation of QOL index) as described above.

(Calculation of Environmental Index)

Next, a specific example of a calculation method of the environmental index (evaluation method regarding environment) will be described. In the present embodiment, the environmental index is calculated on the basis of environmental information acquired in the waking period of the user. In the present embodiment, the server 3 stores, in advance, a table showing the association between a condition regarding the environmental information and the change level of the environmental index, and calculates the environmental index by using the table.

FIG. 23 shows one example of the table used for calculating the environmental index. As shown in FIG. 23, the table shows the association between a condition regarding the environmental information and the change level of the environmental index when the condition is satisfied. The condition regarding the environmental information includes an item (condition) regarding activity content and an item (condition) regarding the environmental value. In the example shown in FIG. 23, the table associates a condition showing that the activity content is "movement (walking)" and the environmental value is "ambient temperature: not lower than 30° C. but lower than 33° C., and humidity: not lower than 60% but lower than 70%", with respect to the change level of the environmental index of "−15". This means that when environmental information satisfying the condition of the activity content being "movement (walking)" and the environmental value being "ambient temperature: not lower than 30° C. but lower than 33° C., and humidity: not lower than 60% but lower than 70%" is acquired, the environmental index is to be decreased by 15. In addition, the table associates a condition showing that the activity content is "work" and the environmental value is "ambient temperature: lower than 28° C., and humidity: lower than 60%", with respect to the change level of the environmental index of "+10". This means that when environmental information satisfying the condition of the activity content being "work" and the environmental value being "ambient temperature: lower than 28° C., and humidity: lower than 60%" is acquired, the environmental index is to be increased by 10. As described above, in the table, a condition that increases the environmental index and a condition that lowers the environmental index may both be included, or only either one of the two may be included.

The server 3 calculates the change level of the environmental index corresponding to the acquired environmental information by referring to the table. For example, when environmental information in which the activity content is "movement (walking)" and the environmental value is "ambient temperature: 31° C. and humidity 65%" is acquired, the server 3 calculates "−15" as the change level (of the environmental index) corresponding to the environmental information. In the present embodiment, the server 3 calculates corresponding change levels for each set of environmental information acquired within a predetermined period of time (in the present embodiment, within today).

Furthermore, the server 3 calculates the environmental index on the basis of a predetermined basic value (e.g., "50") and the change level of the calculated environmental index. Specifically, a final environmental index is calculated by making addition or subtraction in accordance with the change level of the environmental index with respect to the basic value. For example, when the basic value is "50" and change levels are calculated as "−10", "−15", and "+5", a final environmental index is calculated as "30". The basic value described above may be a predetermined fixed value, or may be calculated on the basis of the environment sensor information sensed during the waking period. When the server 3 can acquire the weather of the location of the user, the basic value may be set variably in accordance with the weather. More specifically, the server 3 may calculate the environmental index that takes into consideration the weather of the location of the user. In the present embodiment, environmental index is calculated as an integer from 0 to 100, and a larger numerical value of the environmental index represents the environment around the user being more comfortable.

In another embodiment, the environmental index may be calculated on the basis of the season and/or area (positional information). For example, the server 3 may specify the area and season on the basis of information regarding the current date and time and positional information of the hand-held terminal 5. The server 3 may prepare multiple types of tables for each area and season as the table for calculating the change level of the environmental index, and calculate the change level described above by using a table corresponding to the specified area and season.

(Calculation of Emotion Index)

Next, a specific example of a calculation method of the emotion index (evaluation method regarding emotion) will be described. In the present embodiment, the emotion index is calculated on the basis of emotion information acquired in the waking period of the user. As described above, in the present embodiment, the emotion information includes respective indices indicating the degree of three of five types of emotions (anger, joy, sadness, hate, and pleasure). The server 3 calculates the emotion index on the basis of each of the indices. Specifically, the server 3 calculates the emotion index such that larger indices of negative emotions (in the present embodiment, anger sadness, and hate) result in a smaller value (of the emotion index). In addition, the server 3 calculates the emotion index such that larger indices of positive emotions (in the present embodiment, joy and pleasure) result in a larger value (of the emotion index). For example, the server 3 may calculate the emotion index by making, with respect to a predetermined basic value (e.g., "50"), a subtraction by an amount in accordance with the index indicating the negative emotions, and an addition by an amount in accordance with the index indicating the positive emotions. The basic value may be a predetermined fixed valued, or may be set variably in accordance with the user's schedule information (e.g., information representing whether being holiday or not, busy or not, etc.), activity information, and/or weather. The basic value may be set, for example, relatively high for a holiday and relatively low for a work day. Furthermore, for example, the basic value may be set high on a day in which the user is performing a recreational (leisure) activity, and may be set low on a day in which the user is performing a work activity. Still further, for example, the basic value may be set high on a fine weather day and low on a bad weather day. In the manner described above, in the present embodiment, the emotion index is calculated to be large when the emotion of the user is more positive. In the present embodiment, the emotion index is calculated as an integer from 0 to 100.

At step S115, the server 3 calculates a comprehensive index (QOL index) on the basis of each of the factor indices calculated at step S114. The QOL index may be calculated with any method that calculates the QOL index so as to have a level reflecting each of the factor indices. For example, in the present embodiment, the server 3 calculates, as the QOL index, a value obtained by adding up the factor indices each assigned with a predetermined weight. In the present embodiment, the QOL index is calculated as an integer from 0 to 100.

When each of the indices is calculated at steps S114 and S115, the server 3 stores (accumulates) evaluation result data indicating each of the calculated indices. As shown in FIG. 21, the evaluation result data includes health index data indicating the health index, environmental index data indicating the environmental index, emotion index data indicating the emotion index, and QOL index data indicating the QOL index. In the present embodiment, these four types of index data indicate, for example, respective indices from the latest to those calculated in the past in a predetermined storage period (e.g., three months). Thus, when each of the indices is calculated at steps S114 and S115, the server 3 updates each set of the index data so as to have a content including each of the newly calculated indices.

At step S116, the server 3 specifies the content of the network service in accordance with the evaluation result. More specifically, the server 3 specifies the content of the network service to be provided to the user on the basis of the evaluation result obtained at step S114 and/or S115. In the present embodiment, a service of presenting the evaluation result is provided regardless of the content of the evaluation result. Regarding a service other than presenting the evaluation result (providing advice information, recommendation information, and content, and service regarding giving a privilege); whether to provide the service or not and what content is to be provided are specified in accordance with the evaluation result.

In the present embodiment, the server 3 stores, in advance, a table showing the association between a condition regarding the evaluation result (each index) and service content to be provided, and specifies the service content by using the table. FIG. 24 shows one example of a table used for determining the network service in accordance with the evaluation result. As shown in FIG. 24, the table shows the association between a condition regarding each of the indices (QOL factor indices and QOL index), and a service content to be provided when the condition is satisfied. It should be noted that, in FIG. 24, "-" shows that a condition has not been set.

In the example shown in FIG. 24, the table includes a set in which a condition of the QOL index shown to be not larger than 30 is associated with advice information of advice A and recommendation information regarding commodity A ((a) shown in FIG. 24). In this manner, the condition regarding the evaluation result may include a condition regarding the QOL index. Thus, the server 3 may specify the content of the network service on the basis of the QOL index.

Furthermore, in the example shown in FIG. 24, the table includes a set in which a condition of the health index being not larger than 30 and the emotion index being not larger than 30 is associated with advice information of advice B and recommendation information regarding commodity B ((b) shown in FIG. 24). In this manner, the condition regarding the evaluation result may include a condition regarding a combination of each index (factor index and/or comprehensive index). Thus, the server 3 may specify the content of the network service on the basis of two or more indices.

Furthermore, in the example shown in FIG. 24, the table includes a set in which a condition of the health index being not larger than 30, the environmental index being not larger than 30, and the preference information showing that the user has interest in physical exercise is associated with advice information of advice C ((d) shown in FIG. 24). In this manner, the condition regarding the evaluation result may include a condition regarding the preference information. Thus, in addition to the evaluation result (each index), the server 3 may specify the content of the network service on the basis of the preference information.

Furthermore, in the example shown in FIG. 24, the table includes a set in which a condition showing the health index to be not smaller than 70 is associated with addition of points ((f) shown in FIG. 24). In the manner described above, the server 3 gives a privilege to the user on the basis of the evaluation result regarding health (more specifically, under a condition that the evaluation regarding health is better than a predetermined standard).

The server 3 specifies the content of the network service to be provided by referring to the table and on the basis of the calculated evaluation result. More specifically, when the calculated evaluation result satisfies a condition included in the table, the server 3 provides a network service associated with the condition. Although not diagrammatically represented, the server 3 accumulates and stores, in the storage section, data indicating a specified service for each user. Thus, the server 3 stores information indicating the service content to be provided with respect to the user.

The server 3 accumulates information regarding the user (the user status data and the evaluation result data) in the storage section, more specifically, stores past information of the user. Thus, in another embodiment, the server 3 may determine the content of the service data to be provided to a certain user, on the basis of past information (the user status data and/or the evaluation result data) accumulated in the storage section regarding the user. For example, the server 3 may determine the service content on the basis of evaluation result of the past one week (e.g., an average value of indices over the past one week), or may determine the service content on the basis of the difference between the present evaluation result and the past evaluation result (e.g., the level of change of an index of the current week from that in the last week).

In addition, the server 3 accumulates information regarding multiple users (the user status data and the evaluation result data) in the storage section for each of the users. Thus, the server 3 may determine the content of the service data to be provided to a certain user on the basis of information (the user status data and/or the evaluation result data) accumulated in the storage section regarding another user who is different from the certain user. For example, the server 3 may calculate an average value of an index for predetermined multiple users, and determine the service content on the basis of a relationship between the average value and an index of a certain user. It should be noted that the user (user for which an average value is to be calculated) whose information is used for determining the service content is not limited to all users subscribing to the network service, and may be certain users satisfying a predetermined condition (e.g., users in the same age group, users living in the same area, users of which a calculated index is in the same range).

Furthermore, for example, the server 3 may determine the content of the service data to be provided to a certain user on the basis of past information (the user status data and the evaluation result data) regarding another user different from the certain user. For example, the server 3 calculates the change of a predetermined index (e.g., level of deterioration of health index, etc.) in a predetermined period of time from the present to the past for predetermined multiple users. Then, the server 3 specifies another user having the same trend of the calculated change as the certain user to which the service is to be provided (e.g., the health index being deteriorated by equal to or larger than a predetermined ratio in a single month, etc.). Furthermore, the server 3 determines the service content to be provided to the certain user on the basis of the service content provided in the past to the specified other user. In this manner, the server 3 may determine the service content to be provided to the user, by using past information of another user and referring to the service content provided to the other user whose change in index has the same trend as the user.

At step S116, the server 3 may specify the service content on the basis of whether or not the evaluation result has been improved from a predetermined standard. For example, the server 3 may judge whether or not the evaluation result (various types of indices calculated at steps S114 and S115) has been improved from a predetermined standard, and provide a predetermined network service (e.g., give a privilege) to the user under a condition that the evaluation result is judged to be improved from the predetermined standard. The specific content of the predetermined standard may be any content, and, for example, a predetermined value (fixed value) may be used, or a value based on past evaluation result (indices) may be used. For example, the server 3 may use, as a standard, an average value of the last one week (or a value obtained by adding a predetermined value to the average value). Thus, the server 3 may give a privilege to the user under a condition that an index calculated recently is higher than an average value of the index in the last week.

In the present embodiment, the server 3 repeatedly provides (transmits) the service data (advice information, etc.) to the hand-held terminal 5. Thus, additional service is provided on the basis of the evaluation result of the user after a certain service is provided. With this, since service data such as advice information is repeatedly (continuously) provided to the user, the user can be effectively encouraged to improve QOL.

The server 3 may compare the evaluation result between before and after providing certain service data to the hand-held terminal 5, and specify content of a service to be provided newly (additional service) on the basis of the comparison result. More specifically, as a result of the comparison, the server 3 may provide services with different contents in a case where the evaluation result is judged to be improved and in a case where evaluation result is judged not to be improved. For example, the server 3 may calculate the difference in the evaluation result (index) between before and after providing certain advice information, and specify, on the basis of the calculated difference, the content of advice information to be provided after providing the certain advice information.

In another embodiment, from the evaluation result, the server 3 may update the condition (table shown in FIG. 24 in the above described embodiment) for determining the service content to be provided on the basis of an evaluation result of one or more users. For example, when the advice information is presented to a user, the server 3 may compare the evaluation result of the user between before and after presenting the advice information, and update the condition regarding the advice information on the basis of a comparison result. For example, as a result of the comparison, when the server 3 assesses that the evaluation result (e.g., QOL index) of the user has improved between before and after presenting the advice information, the server 3 may update the condition such that the advice information is more likely to be presented. The judgment of whether or not to update the condition may be performed on the basis of evaluation results regarding multiple users. For example, when a predetermined number or more (predetermined ratio or higher) users had improved evaluation results among multiple users presented with a certain advice information, the server 3 may update the condition such that the advice information is more likely to be presented. With this, since the condition for providing the advice information can be altered depending on the actual effect, more appropriate advice information can be presented to the user.

Similarly to the case with the advice information, the server 3 can update the condition on the basis of an evaluation result of one or more users for services other than the advice information (provide recommendation information and/or content). Regarding the recommendation information, for example, the server 3 may compare the evaluation result between before and after the user purchases a commodity as a result of the recommendation information, and update the condition regarding the recommendation information on the basis of the result of the comparison. Regarding providing of content, the server 3 may compare the evaluation result between before and after the content is provided, and update the condition regarding providing of the content on the basis of the result of the comparison.

At step S117, the server 3 transmits, to the hand-held terminal 5, service data related to the network service to be provided. More specifically, the server 3 transmits data representing an evaluation result based on steps S114 and S115 as the service data to the hand-held terminal 5. Furthermore, the server 3 transmits, to the hand-held terminal 5, service data regarding the service content specified at step S116. For example, when providing a service of presenting the advice information, the server 3 transmits data indicating the advice information to the hand-held terminal 5 as the service data. For example, when providing a service of presenting the recommendation information, the server 3 transmits data indicating the recommendation information to the hand-held terminal 5 as the service data. For example, when providing a service of providing content, the server 3 transmits data of the content to the hand-held terminal 5 as the service data. For example, when providing a service of giving a privilege, the server 3 transmits data indicating a notification of giving the privilege to the hand-held terminal 5 as the service data.

The server 3 stores, in the storage section for each user, data of privilege information (privilege data) indicating a privilege to be given to a user (see FIG. 21). At step S117, when providing the service of giving a privilege, the server 3 updates the privilege data stored in the storage section so as to have a content indicating the privilege to be given. The privilege data is referred to by an information processing apparatus (shop server and billing server described later) that executes a process related to a privilege (process of actually giving a privilege, such as, for example, billing process and purchasing process) when actually giving the privilege. The user utilizes the privilege, and billing or calculation of charge is performed in consideration of the privilege data.

For example, when the privilege relates to purchasing of a commodity or the like, the shop server refers to the privilege data when the user purchases a commodity or the like, next. Here, the shop server is a server that manages purchase, billing, and providing of a commodity or the like, and may be the same server as, or a different server from, the server 3. For example, when the user purchases a commodity or the like, shop server calculates, as a billing amount, an amount obtained after discounting an amount of money in accordance with the privilege data off the amount of money of the purchased commodity or the like. The privilege data may indicate points that can be used when purchasing the commodity or the like, or may indicate the amount of discount.

For example, when the privilege relates to usage charge of the hand-held terminal 5, the billing server refers to the privilege data for the billing of the usage charge. The billing server is a server that performs a billing process by calculating the usage charge of the hand-held terminal 5, and may be the same server as, or a different server from, the server 3. For example, when calculating the usage charge of the hand-held terminal 5, the billing server calculates, as the usage charge, an amount obtained after discounting an amount of money in accordance with the privilege data off a predetermined usage charge. The privilege data may indicate points that can be used for the usage charge, or may indicate the amount of discount.

In the present embodiment, the server 3 calculates a combined usage charge for the use of communication function (a function of performing communication through a mobile phone communication network, and also includes a telephone call function by the communication) on the hand-held terminal 5, and the use of the network service on the hand-held terminal 5. As a result, the user can conveniently pay telephone call charges and the usage charge of the network service together. Specifically, the server 3 stores, in the storage section, usage charge data indicating the usage charge for each user. The billing server refers to the usage charge data stored in the storage section of the server 3 and executes the billing process. The calculation method for the usage charge may be any method, and the server 3 may apply a fixed amount of usage charge for a unit period, or may calculate the usage charge in accordance with a communication volume and/or the usage amount of the network service.

In the present embodiment, at step S117, the server 3 transmits the service data to the hand-held terminal 5 of the user who is the subject of evaluation, and to a terminal of the notification-subject user set for the user. More specifically, the server 3 transmits the service data to the terminal of the notification-subject user indicated by the notification user data containing the user data. Although details will be described later, the service data transmitted to the hand-held terminal 5 of the user who is the subject of evaluation and the service data transmitted to the terminal of the notification-subject user set by the user may be the same or different. Thus, the server 3 may provide network services with different contents to the user who is the subject of evaluation and to the notification-subject user.

At step S118, the server 3 judges whether or not there has been a request from the hand-held terminal 5 of the user. More specifically, at step S102, the server 3 judges whether or not a request transmitted from the hand-held terminal 5 has been received. When the judgment result at step S118 is positive, the process at step S119 is executed. On the other hand, when the judgment result at step S118 is negative, the process at step S111 is executed once again.

At step S119, the server 3 executes a process in accordance with the request received at step S118. For example, when the request is a request to login to a website, the server 3 transmits, to the hand-held terminal 5, information of an image (web page) for login. Furthermore, for example, when the request is a request to acquire a web page, the server 3 transmits information of the web page to the hand-held terminal 5. On the hand-held terminal 5, the processes at steps S103 and S104 are executed in accordance with the process on the server 3 at step S119.

Next after step S119, the server 3 executes the process at step S111 once again. The server 3 repeatedly executes the series of processes at steps S111 to S119. It should be noted that the server 3 executes the series of processes at steps S111 to S119 with respect to each hand-held terminal carried by multiple users who receive the network service.

6. Specific Example of Information to be Presented

Next, a specific example of information presented to the user through the above described processing action of the information processing system 1 will be described. As described above, the server 3 performs an evaluation of the user at a predetermined timing in a single day, and transmits, to the hand-held terminal 5, the service data associated with the network service in accordance with the evaluation result. On the hand-held terminal 5, information based on the received service data is presented to the user.

Figure 25:
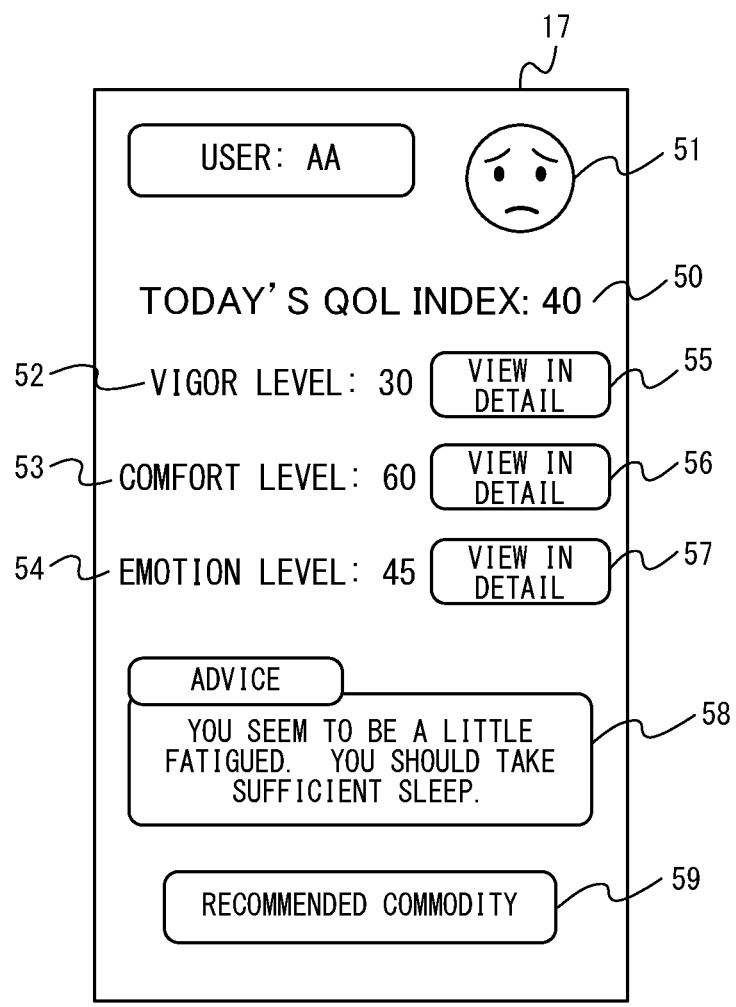
FIG. 25 shows a non-limiting example of information presented on the hand-held terminal 5.

FIG. 25 shows one example of the information presented on the hand-held terminal 5. In the present embodiment, at step S36 (step S117) described above, when the service data is transmitted from the server 3 to the hand-held terminal 5, the hand-held terminal 5 displays, for example, an image shown in FIG. 25 on the display 17 on the basis of the service data received at step S37 (step S104) described above.

As shown in FIG. 25, a QOL score image 50 and a face image 51 are displayed on the display 17. The QOL score image 50 represents an evaluation result of an overall evaluation, and specifically represents a numerical value (score) of the QOL index. On display, the QOL score image 50 is displayed as "(Today's) QOL index number" in order to be easily understood by the user.

The face image 51 is displayed such that the display style thereof (specifically, facial expression) is changed depending on the QOL index. For example, when the QOL index is at a moderate level, a face image representing an ordinary facial expression is displayed; when the QOL index is relatively high (good numerical value), a face image representing a smiley facial expression is displayed; and when the QOL index is relatively low (bad numerical value), a face image representing a fatigued facial expression is displayed as shown in FIG. 25. By displaying the face image 51 in such manner as the evaluation result, the user can recognize the level of QOL as the evaluation result, intuitively.

As described above, when the numerical value of the QOL index is calculated as the evaluation result, the numerical value itself may be presented to the user or information representing the magnitude of the numerical value may be presented to the user. By presenting such information, the level of QOL which is the evaluation result can be presented to the user in an easily understandable manner. Other than the score and image described above, the presented information may represent the fatigue level. For example, in another embodiment, information representing the QOL index in five grades of A to E may be presented.

As shown in FIG. 25, various types of score images 52 to 54 are displayed on the display 17. These score images 52 to 54 respectively represent numerical values (scores) of the factor indices described above. The health score image 52 represents a numerical value of the health index which is a result of the evaluation regarding health of the user, and, on display, is displayed as "vigor level" in order to be easily understood by the user. The environmental score image 53 represents a numerical value of the environmental index which is the evaluation result regarding environment of the user, and, on display, is displayed as "comfort level" in order to be easily understood by the user. The emotion score image 54 represents a numerical value of the emotion index which is the evaluation result regarding the environment of the user, and, on display, is displayed as "emotion level" in order to be easily understood by the user.

Detail buttons 55 to 57 associated with the respective score images 52 to 54 are displayed on the display 17. The detail button 55 is associated with the health score image 52, and is a button for displaying further detailed information of the health index. The detail button 56 is associated with the environmental score image 53, and is a button for displaying further detailed information of the environmental index. The detail button 57 is associated with the emotion score image 54, and is a button for displaying further detailed information of the emotion index. In response to the user making an input (e.g., touching) with respect to each of the detail buttons 55 to 57, the hand-held terminal 5 displays, instead of the screen shown in FIG. 25, detailed information (described later with reference to FIG. 26) for the index associated to the detail button on the display 17.

In addition, an advice image 58 representing the advice information is displayed on the display 17. The advice image 58 represents the advice information corresponding to the evaluation result (each of the score images 50, and 52 to 54) that is presented (displayed) simultaneously. The advice information may be, among multiple evaluation results presented simultaneously, information representing an advice corresponding to the overall evaluation, or may be an advice corresponding to some (or one) of the evaluations. For example, the advice image 58 shown in FIG. 25 relates to the health index shown by the health score image 52 being relatively low and represents an advice for improving the health index.

In addition, a recommendation information button 59 is displayed on the display 17. The recommendation information button 59 is a button for displaying the recommendation information corresponding to the evaluation result (each of the score images 50, and 52 to 54) that is presented (displayed) simultaneously. More specifically, in response to the user making an input with respect to the recommendation information button 59, the hand-held terminal 5 displays the recommendation information on the display 17 instead of the screen shown in FIG. 25. In another embodiment, the recommendation information corresponding to the evaluation result may be displayed in addition to the evaluation result, instead of the recommendation information button 59.

Figure 26:
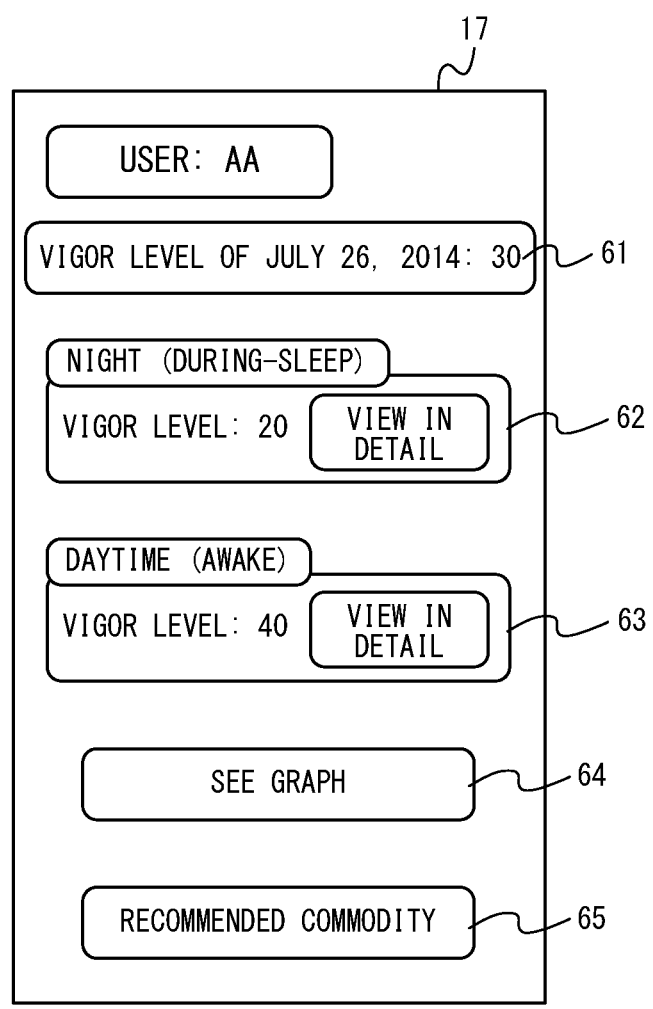
FIG. 26 shows one example of an image displayed on a display 17 when an input is made with respect to a detail button 55 shown in FIG. 25.

A specific example of the image displayed on the handheld terminal 5 when an input is made with respect to the detail button will be described next. FIG. 26 shows one example of the image displayed on the display 17 when an input is made with respect to the detail button 55 shown in FIG. 25.

In FIG. 26, a health score image 61 is displayed on the display 17. Similarly to the health score image 52 shown in FIG. 25, the health score image 61 represents a numerical value of the health index. However, the health score image 61 shown in FIG. 26 contains information regarding the date on which the evaluation has been performed.

In addition, a sleep-state score image 62 and an awake-state score image 63 are displayed on the display 17. The sleep-state score image 62 represents a health index (referred to as "sleep-state health index") calculated based on information (biological information) sensed during the sleeping period. In the present embodiment, the sleep-state health index is calculated by the server 3 on the basis of the health information described above. More specifically, the sleep-state health index is calculated on the basis of a sleep index and a fatigue index (first fatigue level) included in the health information, and is calculated as, for example, a total value of the fatigue index and the sleep index each assigned with a predetermined weight.

The awake-state score image 63 represents a health index (referred to as "awake-state health index") calculated based on information (positional information and environmental information) sensed during the waking period. In the present embodiment, the awake-state health index is calculated by the server 3 on the basis of the activity information described above. For example, as the awake-state health index, the numerical value of the second fatigue level calculated on the basis of the activity information may be used.

On display, the score images 61 to 63 are displayed as "vigor level" in order to be easily understood by the user, similarly to the health score image 52.

The sleep-state score image 62 and the awake-state score image 63 each includes a detail button (see FIG. 26). When an input is made with respect to any of these detail buttons, the hand-held terminal 5 displays further detailed information regarding an index represented by each of the score images. For example, the hand-held terminal 5 may display information used for calculating an index (e.g., for the sleep-state health index, various types of sleep indices or, for the awake-state health index, the activity information used for calculating the awake-state health index).

In addition, a graph display button 64 is displayed on the display 17. The graph display button 64 is a button for displaying a graph related to the health index. More specifically, in response to the user making an input with respect to the graph display button 64, the hand-held terminal 5 displays the graph on the display 17 instead of the screen shown in FIG. 26. For example, the graph may be a graph showing the change in the health index, the sleep-state health index, and the awake-state health index in a predetermined period of time (e.g., in the last week).

In addition, a recommendation information button 65 is displayed on the display 17. The recommendation information button 65 is a button for displaying the recommendation information, similarly to the recommendation information button 59 shown in FIG. 25. However, the recommendation information button 65 shown in FIG. 26 is a button for displaying the recommendation information regarding the health index (may be sleep-state health index or awake-state health index). More specifically, in response to the user making an input with respect to the recommendation information button 65, the hand-held terminal 5 displays the recommendation information regarding a commodity or the like for improving the health index on the display 17, instead of the screen shown in FIG. 26. When the recommendation information to be presented depending on the evaluation result includes a content related to the health index (related to a commodity or the like for improving the health index), the recommendation information button 65 may be displayed; and when said recommendation information includes a content related to an index other than the health index, the recommendation information button 65 may be not displayed.

Figure 27:
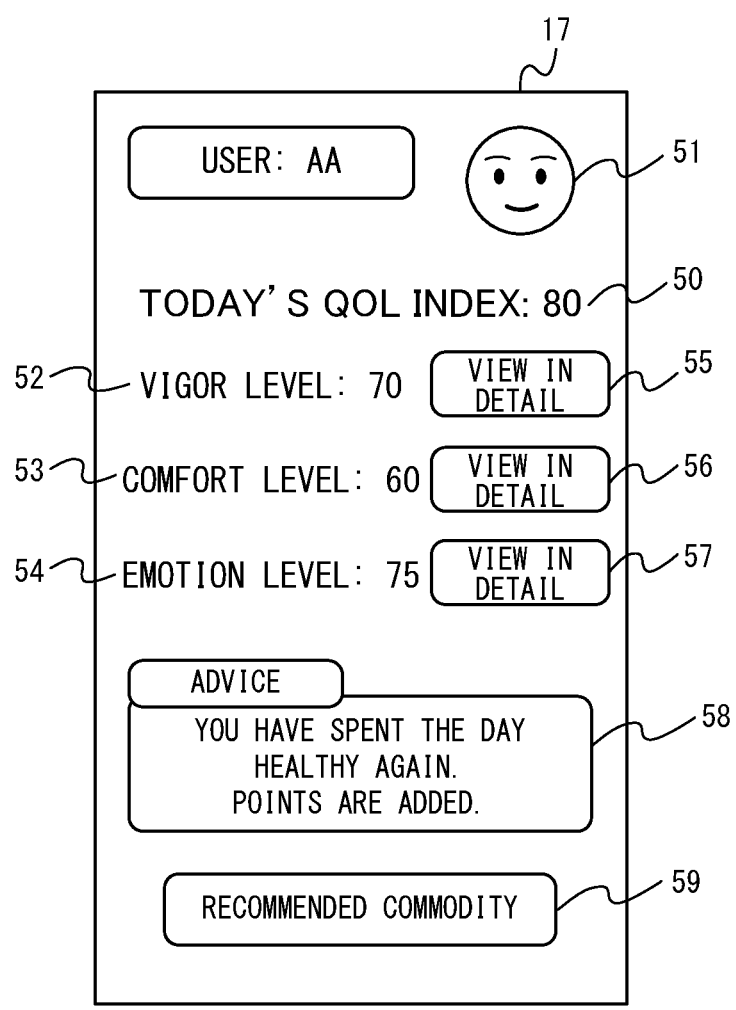
FIG. 27 shows one example of an image displayed on the display 17 when a privilege is given to the user.

A specific example of the image displayed on the hand-held terminal 5 when the privilege is to be given to the user as the network service will be described next. FIG. 27 shows one example of the image displayed on the display 17 when the privilege is to be given to the user.

As shown in FIG. 27, also when the privilege is to be given, the images 51 to 59 are each displayed on the display 17 similarly to when other services are to be provided. However, instead of the advice information, in FIG. 27, the advice image 58 represents a message notifying that the privilege has been given. In such manner, when the privilege is to be given, a notification showing that the privilege has been given may be presented to the user.

Figure 28:
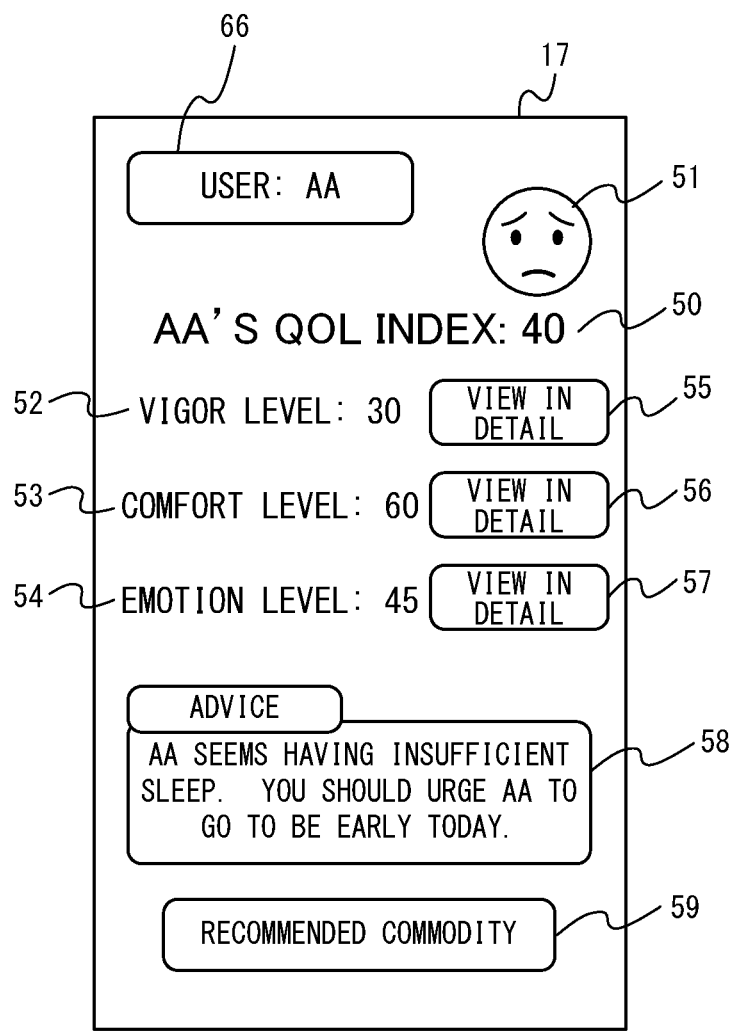
FIG. 28 shows one example of an image displayed on a terminal of a notification-subject user.

A specific example of the image displayed on the terminal of the notification-subject user will be described next. FIG. 28 shows one example of the image displayed on the terminal of the notification-subject user. The image shown in FIG. 28 is displayed on the terminal of the notification-subject user when the image shown in FIG. 25 is displayed on the hand-held terminal 5 of the user who is the subject of evaluation.

As shown in FIG. 28, also on the terminal of the notification-subject user, the images 51 to 59 are each displayed similarly on the hand-held terminal 5 of the user who is the subject of evaluation. The image on the terminal of the notification-subject user is different from the image shown in FIG. 25 in terms of an image 66 showing the name of the notification-subject user being displayed. On the terminal of the notification-subject user, the content of the advice information shown by the advice image 58 are different from the content displayed on the hand-held terminal 5 of the user who is the subject of evaluation. In such manner, by changing the advice for the user who is the subject of evaluation and the advice of the notification-subject user who is not the said user, a more appropriate advice can be presented.

As described above, the server 3 may change the advice information (similarly to the recommendation information) depending on the user to whom the advice information is to be presented. For example, a case will be discussed in which the user of the hand-held terminal 5 had a low emotion index since being scolded by his/her superior at work. In this case, the server 3 may present the user with advice information of "take a deep breath" or present recommendation information introducing stress alleviation goods. On the other hand, the server 3 may present the notification-subject user with advice information such as "you should cheer up his/her feelings" or "you should cook his/her favorite dish".

Furthermore, the server 3 may present notification-subject users with different information (advice information and/or recommendation information) in accordance with the respective notification-subject user's relationships (parent, child, wife, sibling, family, or friend, etc.) with the user who is the subject of evaluation. For example, in the case of the example described above, when the notification-subject user is a family member, advice information such as "you should cook his/her favorite dish when he/she returns home" may be presented, and, when the notification-subject user is a friend, advice information such as "you should telephone him/her and listen to his/her story" may be presented. By having the server 3 store notification user data including information indicating the relationship between the user who is the subject of evaluation and notification-subject users, the server 3 can specify the relationship.

In FIGS. 25 to 28, when a button (e.g., buttons 55 to 57 or the like shown in FIG. 25) for displaying another image is contained in the image displayed on the hand-held terminal 5, information (the other image) displayed when an input is made with respect to the button may be acquired from the server 3 at any timing. More specifically, the information may be transmitted from the server 3 to the hand-held terminal 5 in advance as the service data, or may be transmitted from the server 3 to the hand-held terminal 5 in response to a request made to the server 3 by the hand-held terminal 5 when an input is made with respect to the button. Thus, the information may be transmitted to the hand-held terminal 5 by the process at step S117 or may be transmitted to the hand-held terminal 5 by the process at step S119.

7. Functions and Effects of Present Embodiment

The information processing system 1 of the embodiment described above exerts the advantageous effects as described next.

Since biological information (pulse, respiration, etc.) is acquired (measured) without any contact with the user, the user does not have to touch a sensor.

Since various types of information for calculating the QOL factor information are acquired by the hand-held terminal 5 and the base device 6, the user does not have to wear a special device on the body.

Since processes for acquiring (measuring) the various types of information are initiated without any operation by the user, the user does not have to perform an operation to cause the terminal system 2 to acquire the various types of information.

Since the various types of information are automatically calculated and an evaluation based on the various types of information is automatically performed, the user does not have to wait until the information is acquired (measured) and the evaluation result is calculated, and does not have to make any special preparation every time for acquiring the information.

As a result, with the embodiment described above, the user can receive a service based on the evaluation of QOL by simply spending his/her life as usual without performing any troublesome operation or tasks. Thus, the service provided in the present embodiment can be continuously used easily by the user. Since providing a service based on the evaluation of QOL is considered to be effective when being continuously performed with respect to the user, the information processing system 1 can provide a more effective service by providing the service with a method with which the user can easily continue, as in the present embodiment.

(Functions and Effects related to Configuration of Information Processing System)

In the embodiment described above, the information processing system 1 includes the stationary type device (the base device 6), the hand-held type device (the hand-held terminal 5) which is a multifunctional terminal connectable to the base device, and the server 3 capable of communicating with the hand-held terminal 5 through a wide area network (the Internet and/or a mobile communication network). The base device 6 is installed around the user in bed, and senses biological information of the user in sleep (step S12). The hand-held terminal 5 transmits, to the server 3 as transmission information, information (health information, and may be biological information itself) calculated from the biological information sensed by the base device 6 (steps S4, S19). The server 3 transmits, to the hand-held terminal 5, service data associated with a network service for improving an evaluation result (health index) of an evaluation (calculation of health index) of sleep of the user performed on the basis of the biological information (steps S9, S117). The hand-held terminal 5 presents the user with an image and/or a sound associated with the service data received from the server 3 regarding a predetermined network service at least in a state of not being connected with the base device 6 (steps S37, S104).

With the configuration described above, the information processing system 1 can evaluate health of the user on the basis of the biological information of the user in sleep, and provide the user with a network service in accordance with the evaluation result. Since the base device 6 does not require means for communicating with the server 3 because information is transmitted to the server 3 by the hand-held terminal 5, the configuration of the base device 6 can be simplified. Since the hand-held terminal 5 can present an image and/or a sound associated with the service data in a state of not being connected with the base device 6, the user can easily receive the provided service.

In the embodiment described above, the stationary base device 6 senses user information (biological information) for evaluating QOL of the user (step S12). The hand-held terminal 5 transmits, to the server 3 as transmission information, information (health information, or may be the user information itself) calculated from the user information sensed by the base device 6 (steps S4, S19). The server 3 transmits, to the hand-held terminal 5, service data for providing the user with a network service in accordance with an evaluation result (evaluation result regarding QOL) (QOL index) calculated from the transmission information transmitted from the hand-held terminal 5 (or an evaluation result indicated by the transmission information) (steps S9, S117). With this, the information processing system 1 can evaluate QOL of the user on the basis of the user information, and provide the user with a network service in accordance with the evaluation result. In the description above, the hand-held terminal 5 may present the user with information (information of evaluation result, advice information, recommendation information, information of content included in the service data, and information regarding a privilege, etc.) based on the service data received from the server 3.

In the embodiment described above, the information processing system 1 calculates, as the evaluation result regarding QOL, the QOL index on the basis of three types of information regarding health, environment, and emotion of the user. The evaluation regarding QOL may be performed on the basis of at least one of the three types of information. For example, in another embodiment, an evaluation result (health index described above) regarding health of the user may be calculated as the QOL index. Furthermore, the evaluation regarding QOL may be performed on the basis of other information different from the three types of information. For example, in another embodiment, the QOL index may be calculated on the basis of information (preference information described above) regarding preference of the user.

In the embodiment described above, the stationary base device 6 is installed around the user in bed, and senses user information (biological information) of the user in sleep for evaluating QOL of the user (step S12). The hand-held terminal 5 transmits, to the server 3 as transmission information, information calculated from user information sensed by the base device 6 (steps S4, S19). The server 3 accumulates, in a predetermined storage section as accumulation information, information (health information, or may be transmission information itself) calculated from the transmission information transmitted from the hand-held terminal 5 (step S112).

With this, the information processing system 1 can calculate the information regarding QOL of the user on the basis of the information sensed from the user in sleep. Furthermore, the QOL information is useful information since various types of services can be provided to the user by analyzing or evaluating the information, and becomes further useful information if multiple sets of the information (may be multiple sets of the information for a single user or may be information for multiple users) of QOL exist. In the embodiment described above, since the calculated QOL information is accumulated in the server 3, a large number of sets of the QOL information, which is useful information, can be easily managed without placing a large burden on the storage capacity of the hand-held terminal 5.

The base device 6 initiates sensing of the user information (biological information) in response to becoming communicable with the hand-held terminal 5 (see FIG. 6). With this, since the user does not have to perform an operation for causing the base device 6 to initiate sensing, the time and effort required for the operation by the user can be omitted. In addition, the base device 6 can transmit the information based on the sensed user information to the hand-held terminal 5 without storing information in itself for a long period of time. The embodiment relates to a configuration in which the hand-held terminal 5 and the base device 6 become communicable when the hand-held terminal 5 is mounted on the base device 6. However, another embodiment may be related to a configuration in which the hand-held terminal 5 and the base device 6 become communicable even without mounting the hand-held terminal 5 on the base device 6. For example, when the hand-held terminal 5 and the base device 6 can perform near field communication, a configuration may be used in which the two become communicable in response to entering a wirelessly communicable range.

The hand-held terminal 5 is mountable (or may be placeable) on the base device 6, and the base device 6 initiates sensing of the user information in response to the hand-held terminal 5 being mounted thereon (see FIG. 6). With this, since the user only has to mount the hand-held terminal 5 on the base device 6 and does not have to perform an operation with respect to the base device 6 for causing the base device 6 to initiate sensing, the time and effort of the operation by the user can be omitted.

The base device 6 ends the sensing in response to the user being no longer sensed by the Doppler sensor 24 (step S20). In other words, even when the hand-held terminal 5 is removed from the base device 6, the base device 6 continues sensing of the user information (see FIG. 6). With this, since the base device 6 continues the sensing even when the hand-held terminal 5 is removed from the base device 6 for some reason during the sensing (e.g., when the user rolls over in bed and accidentally hits the hand-held terminal 5), sensing of the user in sleep can be performed with certainty. In another embodiment, the base device 6 may end the sensing under a condition that the user has awakened. With this, similarly to the embodiment described above, the base device 6 can continue sensing of the user information even when the hand-held terminal 5 is removed from the base device 6.

The information processing system 1 calculates a sleep index related to sleep of the user on the basis of the user information (biological information) (step S13), and operation and/or function of the hand-held terminal 5 is controlled depending on the sleep index (FIG. 6, step S15). With this, the operation and/or function of the hand-held terminal 5 can be controlled depending on the sleep state of the user. For example, power consumption can be reduced by setting the hand-held terminal 5 to the OFF-mode during sleep, and sleep of the user can be prevented from being disturbed by turning OFF the telephone call function during sleep.

With the embodiment described above, the hand-held terminal 5 is electrically connectable to the stationary base device 6. The base device 6 includes charging means (the power acquisition section 23) supplies power to the hand-held terminal 5 electrically connected to the base device 6 to charge the hand-held type device, and sensing means (the Doppler sensor 24) that senses the user information (biological information) for evaluating QOL of the user. The hand-held terminal 5 transmits, to the server 3 as transmission information, information (health information, or may be user information itself) calculated from the user information sensed by the base device 6. The server 3 accumulates, in a predetermined storage section as accumulation information, the transmission information (or may be information calculated from the transmission information) transmitted from the hand-held terminal 5.

"Electrically connectable" as described above is a meaning that includes the following connection modes.

A mode in which, as in the embodiment described above, the hand-held terminal is detachably/reattachably mounted (or may be placed) on the base device, and become communicable when respective connectors make contact.

A mode in which the hand-held terminal and the base device become communicable when being connected via a detachable/reattachable cable.

A mode in which near field communication between the hand-held terminal and the base device becomes possible when the hand-held terminal is detachably/reattachably mounted or placed on the base device.

With the modes described above, the user information can be sensed without requiring much installation space, since the base device 6 doubles as a battery charger for the hand-held terminal 5 and a sensor device for sensing the user information. Since the transmission information is accumulated in the server 3, a large number of sets of the transmission information, which is useful information, can be easily managed without placing a large burden on the storage capacity of the hand-held terminal 5.

Since the base device 6 has the charging function, the user can be motivated to mount the hand-held terminal 5 on the base device 6. Thus, in cases where the base device 6 initiates sensing of the user information in response to mounting or placing of the hand-held terminal 5 (see FIG. 6), the possibility of the user forgetting to mount the hand-held terminal 5 on the base device 6 can be reduced, whereby sensing by the base device 6 can be performed with more certainty.

The charging means (the power acquisition section 23) charges the hand-held terminal 5 which is a transmission destination of the user information while the user information (biological information) is being sensed. With this, the user information is sensed while the user connects the hand-held terminal 5 to the base device 6 for charging the hand-held terminal 5. While the hand-held terminal 5 is being charged, the user is ordinarily thought to often be near the hand-held terminal 5. Thus, by performing sensing of the user information when the user is (highly likely to be) near the hand-held terminal 5, the burden on the user during the sensing can be reduced.

(Functions and Effects Related to Evaluation Based on Multiple Sets of Information)

In the embodiment described above, the information processing system 1 includes the stationary base device 6 and the hand-held terminal 5. The base device 6 senses first user information (biological information) for evaluating QOL of the user while the user is asleep (steps S1, S12). The hand-held terminal 5 senses second user information (positional information, environment sensor information, information of sound sensed by the microphone, information of image captured by the camera, etc.) for evaluating QOL of the user while the user is awake (steps S5, S22, S51). The information processing system 1 performs an evaluation regarding QOL of the user on the basis of the first user information and the second user information (steps S7, S35, S114). With the configuration described above, since the information processing system 1 evaluates QOL by using both the first user information sense while the user is asleep and the second user information sensed while the user is awake, the information processing system 1 can perform the evaluation of QOL by taking into consideration the state of the user through the whole day.

In the configuration described above, the first user information and the second user information may be the same or different. For example, the first user information and the second user information may be biological information regarding the user. Alternatively, when both types of the user information are biological information, the first user information and the second user information may be the same type of biological information or may be different types of biological information.

The information processing system 1 successively transmits the first user information (biological information, or may be information calculated from the first user information) to the hand-held terminal 5 (step S1). The hand-held terminal 5 suspends sensing of the second user information while receiving information from the base device 6 (see FIG. 1). With this, the hand-held terminal 5 can judge whether or not to perform sensing of the second user information by receiving information from the base device 6. The hand-held terminal 5 can efficiently perform the sensing since sensing of the second user information can be suspended in a period in which the necessity thereof is low (in a period in which the user is estimated not to be awake).

In addition, the information processing system 1 calculates a first index (first fatigue level/health information) that concerns QOL of the user and is calculated on the basis of the first user information (step S17), and calculate a second index (second fatigue level/activity information, environmental information, emotion information) that concerns QOL of the user and is calculated on the basis of the second user information (step S114). The information processing system 1 presents the user with the first index (the sleep-state score image 62/the health score image 52) and the second index (the awake-state score image 63/the environmental score image 53 and the emotion score image 54) in association with one another (FIG. 26). With this, the first index based on information sensed while the user is asleep and the second index based on information sensed while the user is awake can be presented to the user in an easily understandable manner since the two are associated with one another.

Furthermore, the information processing system 1 presents the user with an evaluation result (the health score image 61 or the QOL score image 50) that concerns QOL and is based on the first index and the second index, and at least one (both in the examples shown in FIGS. 25 and 26) of the first index (the sleep-state score image 62 or the health score image 52) and the second index (the awake-state score image 63 or respective images 53 and 54) in association with one another (FIGS. 25 and 26). With this, the evaluation result based on the two indices and at least one of the indices can be presented to the user in an easily understandable manner since the two are associated with one another.

The hand-held terminal 5 is mountable (or placeable) on the base device 6, and suspends sensing of the second user information while being mounted (or placed) on the base device 6. With this, when the user is not carrying the hand-held terminal 5, the hand-held terminal 5 suspends sensing of the second user information. Ordinarily, the user is thought to be not carrying the hand-held terminal 5 while being asleep. Thus, with the configuration described above, the possibility of the hand-held terminal 5 sensing the second user information unnecessary while the user is asleep can be reduced.

In the embodiment described above, the information processing system 1 includes a first terminal (the base device 6), a second terminal (the hand-held terminal 5), and the server 3. The base device 6 senses the first user information (biological information) for evaluating QOL of the user (steps S1, S12). The hand-held terminal 5 senses the second user information (positional information, environment sensor information, information of sound sensed by the microphone, information of image captured by the camera, etc.) for evaluating QOL of the user (steps S5, S22, S51). In addition, the hand-held terminal 5 transmits information (health information or may be the first user information itself) calculated from the first user information to the server 3 as the first transmission information (steps S4, S19). Furthermore, the hand-held terminal 5 transmits, together with or separately from the first transmission information, information (activity information or may be the second user information itself) calculated from the second user information to the server 3 as the second transmission information (step S5, step S23, etc., step S54). One of the base device 6 and the hand-held terminal 5 performs sensing while the user is asleep, and the other performs sensing while the user is awake (see FIG. 4). The server 3 performs an evaluation regarding QOL of the user on the basis of the first transmission information and the second transmission information (step S7, S114, or S115).

Since the information processing system 1 evaluates QOL by using both the first user information sense while the user is asleep and the second user information sensed while the user is awake, the information processing system 1 can perform the evaluation of QOL by taking into consideration the state of the user through the whole day. In addition, since the information sensed by the first terminal (the base device 6) is transmitted to the server 3 by the second terminal (the hand-held terminal 5), the base device 6 does not have to have means to communicate with the server 3, and the configuration of the base device 6 can be simplified. In another embodiment, the base device 6 may include a communication section that performs communication with the server 3. In this case, the second user information (or information calculated from the second user information)

sensed by the hand-held terminal 5 may be transmitted to the server 3 via the base device 6.

In the embodiment described above, the stationary type device (the base device 6) senses the first user information (biological information) which is for evaluating QOL of the user and which is information regarding state and/or behavior of the user (steps S1, S12). The hand-held terminal 5 senses the second user information (positional information, environment sensor information, information of sound sensed by the microphone, information of image captured by the camera, etc.) that is for evaluating QOL of the user and that is information regarding state and/or behavior of the user (steps S5, S22, S51). In addition, the hand-held terminal 5 transmits information (health information or may be the first user information itself) calculated from the first user information to the server 3 as the first transmission information (steps S4, S19). Furthermore, the hand-held terminal 5 transmits, together with or separately from the first transmission information, information (various types of QOL factor information or may be the second user information itself) calculated from the second user information to the server 3 as the second transmission information (step S5, step S23, etc., step S54). The server 3 performs an evaluation regarding QOL of the user on the basis of the first transmission information and the second transmission information (steps S7, S114). It should be noted that "information regarding state and/or behavior of the user" described above may be information representing the state of the user (e.g., the above described biological information, positional information, environmental information, emotion information, and preference information), or may be information representing the behavior of the user (e.g., the above described positional information and activity information).

The information processing system 1 can perform the evaluation in consideration of the state of the user through a longer period of time, since evaluation of QOL is performed by using both the first user information sensed by the base device 6 and the second user information sensed by the hand-held terminal 5. For example, it is also possible have the hand-held terminal 5 sense the second user information in a period where the user is carrying the hand-held terminal 5, and have the base device 6 sense the first user information in a period where the user is not carrying the hand-held terminal 5. In addition, since the information sensed by the base device 6 is transmitted to the server 3 by the hand-held terminal 5, the base device 6 does not have to have means to communicate with the server 3, and the configuration of the base device 6 can be simplified.

The base device 6 senses, as the first user information, information regarding sleep of the user, and the hand-held terminal 5 senses, as the second user information, information regarding behavior content while the user is awake (see FIG. 4). With this, since the information processing system 1 evaluates QOL by using both the first user information sensed while the user is asleep and the second user information sensed while the user is awake, the information processing system 1 can perform the evaluation of QOL by taking into consideration the state of the user through the whole day.

In the embodiment described above, the information processing system 1 includes a first device (the base device 6) and a second device (the hand-held terminal 5). The base device 6 senses, in a state of not being in contact with the user, the first user information (biological information) for evaluating QOL of the user when the user is located indoors (steps S1, S12). The hand-held terminal 5 senses the second user information (positional information, environment sensor information, information of sound sensed by the microphone, information of image captured by the camera, etc.) for evaluating QOL of the user when the user is located outdoors (steps S5, S22, S51). As long as the hand-held terminal 5 can sense the second user information when the user is located outdoors, the hand-held terminal 5 may sense the second user information when the user is located indoors. The information processing system performs an evaluation regarding QOL of the user on the basis of the first user information and the second user information (steps S7, S114).

With the configuration described above, since the information processing system 1 evaluates QOL by using both the first user information sensed when user is located indoors and the second user information sensed when the user is located outdoors, the information processing system 1 can perform the evaluation of QOL by taking into consideration the state of the user through the whole day.

In the embodiment described above, the information processing system 1 includes a first device (the base device 6) and a second device (the hand-held terminal 5). The base device 6 senses the first user information (biological information) for evaluating QOL of the user while the user is asleep (steps S1, S12). The hand-held terminal 5 senses the second user information (positional information, environment sensor information, information of sound sensed by the microphone, information of image captured by the camera, etc.) for evaluating QOL of the user while the user is awake (steps S5, S22, S51). The information processing system 1 performs an evaluation regarding QOL of the user on the basis of the first user information (calculate the first fatigue level at step S17, or calculate the health index at step S114), and performs an evaluation regarding QOL of the user on the basis of the second user information (calculate the second fatigue level at step S114, or calculate the environmental index or the emotion index at step S114). Furthermore, the information processing system 1 performs an evaluation regarding QOL of the user on the basis of the first user information and the second user information (calculate the health index at step S114, or calculate the QOL index at step S115).

With the configuration described above, since the information processing system 1 evaluates QOL by using both the first user information sensed while the user is asleep and the second user information sensed while the user is awake, the information processing system 1 can perform the evaluation of QOL by taking into consideration the state of the user through the whole day. The information processing system 1 can perform a multilateral evaluation regarding QOL since evaluations based on two sets of user information are performed, i.e., the evaluation based on the first user information and the evaluation based on the second user information.

The information processing system 1 calculates an index regarding QOL of the user on the basis of the evaluation result (first fatigue level or health index) based on the first user information and the evaluation result based on the second user information (second fatigue level, or environmental index or emotion index) (step S114 or S115). With this, a QOL index that takes into consideration both sets of user information can be calculated since the index regarding QOL is calculated on the basis of the evaluation results based on the respective sets of the user information.

Furthermore, the hand-held terminal 5 senses the second user information by a sensor (the position sensing section 13, more specifically, a GPS sensor) that is of a type different from the sensor (the Doppler sensor 24) for sensing the first user information by the base device 6. By sensing the respective sets of the user information with different sensors, the user information can be acquired in a further multilateral manner, and the accuracy of the evaluation regarding QOL can be improved.

In the embodiment described above, the information processing system 1 includes the terminal system 2 and the server 3. The terminal system 2 senses the first user information (biological information) regarding sleep of the user while the user is asleep (steps S1, S12), and senses the second user information (QOL factor information) regarding behavior content of the user while the user is awake (step S5). The server 3 transmits, to the terminal system 2, service data for providing the user with a service using the first user information and the second user information (step S9). With the configuration described above, a useful service can be provided by using the first user information regarding sleep of the user and the second user information regarding behavior content of the user.

Furthermore, the server 3 evaluates QOL of the user on the basis of the first user information (at step S114, calculate the health index). The information processing system 1 provides a service for improving QOL on the basis of the evaluation result of QOL of the user, and selects, as service data for providing the service, service data having a content in accordance with preference of the user specified on the basis of the second user information (preference information) (step S116). With this, the information processing system can provide a useful service since the service for improving QOL of the user can be provided with a service content in accordance with the preference of the user.

(Functions and Effects Related to Privilege Bestowal in Accordance with Evaluation Result Regarding Health)

In the embodiment described above, the information processing system includes the server 3 and the terminal system 2 including the hand-held type terminal (the hand-held terminal 5). The terminal system 2 acquires the first information (biological information or positional information) for evaluating health of the user (step S12 or S51). The information processing system performs an evaluation regarding health of the user on the basis of the acquired first information (step S114). The server 3 transmits, to the terminal system, service data for providing a network service in accordance with the evaluation regarding health of the user (steps 9, S36, S117). In addition, the server 3 stores, in a predetermined storage section, privilege information (privilege data shown in FIG. 21) indicating a privilege that is to be given to the user and that relates to the network service and/or the hand-held type terminal. The server 3 is updates the privilege information such that a privilege in accordance with a result of the evaluation regarding health of the user is to be given to the user (step S116).

In the configuration described above, the information processing system 1 gives the user a privilege in accordance with an evaluation result of health of the user. With this, the information processing system 1 can provide the user with a motivation to improve health by giving a privilege to the user, and can provide a useful service that can contribute in health improvement of the user.

The information processing system 1 repeatedly acquires the first information regardless of whether or not an instruction by the user exists (step S12 or S51). In addition, the information processing system 1 repeatedly performs an evaluation on the basis of the first information (in the embodiment described above, the evaluation is repeated every day). The server 3 continuously transmits the service data to the terminal system 2 regardless of whether or not an instruction by the user exists (step S117). In addition, the server 3 gives a privilege as part of a service in the network service that is provided continuously (in the embodiment described above, transmission of the service data is executed every day). With this, the information processing system 1 automatically and continuously performs an evaluation regarding health, and continuously provides the user with a network service in accordance with a result of the evaluation. Thus, the user can continuously receive an evaluation of health without repeatedly giving instructions. By continuously performing an evaluation and giving the user a privilege in accordance with the evaluation, the information processing system 1 can contribute in health maintenance of the user since a motivation to maintain health can be provided to the user.

In the embodiment described above, the information processing system 1 includes the terminal system 2 and the server 3. The terminal system 2 acquires, as the first information, biological information from the user in sleep by a sensor (the Doppler sensor 24) senses the biological information (step S12). The information processing system 1 performs an evaluation regarding health of the user on the basis of the acquired biological information (step S114). The server 3 stores, in a predetermined storage section, privilege information (privilege data shown in FIG. 21) indicating a privilege to be given to the user. The server 3 updates the privilege information such that a privilege in accordance with a result of the evaluation regarding health of the user is to be given to the user. In the configuration described above, since the information processing system 1 gives the user a privilege in accordance with an evaluation result of health of the user, the information processing system 1 can provide the user with a motivation to improve health, and can contribute in health improvement of the user.

The terminal system 2 further acquires second information (may be positional information or activity information) regarding behavior of the user (step S91), and the information processing system 1 assesses preference of the user on the basis of the second information (step S93). The server 3 determines, on the basis of the preference of the user, a content of the privilege to be given to the user (step S116). With this, the information processing system can provide a useful service since the privilege with a content in accordance with the preference of the user can be provided. Since the privilege can be made more attractive to the user, a stronger motivation to improve health can be provided to the user.

In the configuration described above, the server 3 performs an evaluation regarding health on the basis of the first information (biological information) and the second information (positional information or activity information) (step S114). As a result, since the evaluation regarding health can be performed on the basis of two different types of information, the accuracy of the evaluation can be improved.

(Functions and Effects Related to Base Device)

In the embodiment described above, the terminal system 2 (the base device 6) which is one example of a display system has the following configuration.

A sensor (the Doppler sensor 24) that senses user information (biological information) for calculating a state regarding sleep of the user.

The projector 25 that projects and displays a predetermined image.

The control section 22 that causes the projector 25 to project and display an image related to the state of sleep calculated on the basis of the user information (step S18).

The "image related to the state of sleep" may be an image representing a sleep state (e.g., the sleep index described above) or may be an image representing an evaluation result of the sleep state (e.g., the pleasant sleep index number described above). With the configuration described above, the terminal system 2 can, by using the projector 25, project and display an image at a spot easily viewable by the user who is in bed, such as, for example, the ceiling. With this, the terminal system 2 can provide a display that is easy to view by the user in bed. In addition, the terminal system 2 can, by causing the projector 25 to display the image, present the sleep state to the user.

In the embodiment described above, the terminal system 2 (the base device 6) which is one example of the display system has the following configuration.

A sensor (the Doppler sensor 24) that senses user information (biological information) for calculating a state regarding sleep of the user.

The projector 25 that projects and displays a predetermined image.

The control section 22 that specifies a timing regarding awakening of the user on the basis of the user information, and cause the projector to initiate projecting and displaying an image in accordance with the specified timing (step S14, FIG. 6).

The "timing regarding awakening of the user" is, for example, a timing when the user awakens, or a timing before or after the user awakens. The timing when a judgment is made that sleep of the user has become shallow (in other words, the user entering a state prior to awakening) and the timing when a judgment is made that the user have awakened in the embodiment described above can be considered as the "timing regarding awakening of the user". In addition, a timing after the user has awakened and also based on the awakening timing (e.g., a timing reach when a predetermined time period has elapsed from the awakening timing) can be considered as the "timing regarding awakening of the user".

Furthermore, "initiate (projecting and displaying an image) in accordance with the specified timing" includes both a meaning "initiate projecting and displaying at the timing" and a meaning "initiate projecting and displaying at a timing depending on a specified timing (e.g., a timing one minute after the specified timing)".

With the configuration described above, the terminal system 2 can, by using the projector 25, provide a display that is easy to view by the user in bed. In addition, the terminal system 2 can present the user with an image in response to awakening of the user. Thus, the terminal system 2 can present an image to the user at an appropriate timing, and can reduce power consumption by the projector 25.

In the embodiment described above, the terminal system 2 which is one example of the display system has the following configuration.

A sensor (the Doppler sensor 24) that senses user information for calculating a state regarding sleep of the user in bed.

The projector 25 that projects and displays a predetermined image for the user in bed.

The control section 22 that controls the projector 25.

The communication section 10 that performs communication with the server 3 via a network.

With the configuration described above, the terminal system 2 can, by using the projector 25, project and display an image at a spot easily viewable by the user who is in bed, such as, for example, the ceiling. With this, the terminal system 2 can provide a display that is easy to view by the user in bed. Furthermore, since the terminal system 2 includes the communication section that performs communication with the server 3, the terminal system 2 can, for example, acquire an image to be displayed by the projector 25 from the server 3, or transmit, to the server 3, a sensing result (or information based on the sensing result) from the sensor.

The control section 22 causes the projector 25 to display an image related to the state of sleep calculated on the basis of the user information at a timing in accordance with the sleep state of the user, which is a timing specified on the basis of the user information. With this, an image can be presented to user at an appropriate timing depending on the sleep state of the user. In addition, power consumption by the projector 25 can be reduced.

In addition, the control section 22 causes the projector 25 to display an image related to the sleep state at a timing when the user awakens or a timing before the user awakens, which is a timing specified on the basis of the user information. With this, since information related to the sleep state of the user can be presented to the user when the user awakens, useful information can be presented to the user at an appropriate timing.

The terminal system 2 controls power supply to the projector 25 in accordance with the state regarding sleep. For example, the terminal system 2 may start power supply to the projector 25 in accordance with a timing specified on the basis of the user information regarding awakening of the user. More specifically, the terminal system 2 may start power supply to the projector 25 at a timing before the user awakens (or a timing when the user awakens). With this, image display by the projector 25 can be performed when the user awakens while suppressing power supply to the projector 25 when the user is asleep.

The terminal system 2 may change an image (content for sleep onset) for inducing sleep onset of the user and/or an image (content for awakening) for inducing awakening of the user, in accordance with the sleep state of the user, and may cause the projector 25 to project and display the image. For example, brightness of the image projected and displayed by the projector 25 may be changed in accordance with the sleep state of the user.

When the user awakens, the terminal system 2 judges whether or not the awakening is an awakening in mid-course of sleep (see "(Information Presentation at time of Mid-Sleep Awakening)" and "(Presentation of Evaluation Result at time of Awakening)" described above). At this time, the terminal system 2 causes the projector 25 to project and display different images in a case where the awakening of the user is judged to be a mid-sleep awakening and in a case where the awakening of the user is judged not to be a mid-sleep awakening (FIG. 6), respectively. With this, a proper image, depending on whether or not awakening of the user is a mid-sleep awakening, can be presented to the user.

The terminal system 2 performs an evaluation of sleep of the user on the basis of the user information (step S17), and causes the projector 25 to project and display a result of the evaluation at a timing in accordance with the sleep state of the user (e.g., a timing when the user awakens), which is a timing specified on the basis of the user information (step S18). With this, the terminal system 2 can present the evaluation result of the sleep to the user at an appropriate timing.

In the embodiment described above, the terminal system 2 (the base device 6) which is one example of the display system has the following configuration.

A sensor (the Doppler sensor 24) that senses user information (biological information) for calculating a state regarding sleep of the user.

The projector 25 that projects and displays a predetermined image.

The control section 22 (step S14) that controls the projector in accordance with the state of sleep that is calculated on the basis of the user information.

With the configuration described above, the terminal system 2 can, by using the projector 25, project and display an image at a spot easily viewable by the user who is in bed, such as, for example, the ceiling. With this, the terminal system 2 can provide a display that is easy to view by the user in bed. In addition, by controlling the projector 25 in accordance with the sleep state of the user, the terminal system 2 can appropriately control the power supply (ON/OFF) of the projector 25 and/or the image projected and displayed by the projector 25, in accordance with the sleep state.

In the embodiment described above, the terminal system 2 which is one example of the display system has the following configuration.

A sensor (the Doppler sensor 24) that senses user information for calculating a state regarding sleep of the user in bed.

The projector 25 that projects and displays a predetermined image for the user in bed.

A display device (the display 17 of the hand-held terminal 5) detachably/reattachably connected to the projector 25, and having a screen that displays an image identical to or different from the predetermined image.

With the configuration described above, a display that is easy to view by the user in bed can be provided by the projector 25, and the image can be presented by the display device at a position different from the projection spot of the projector 25. In another embodiment, the display device may be formed integrally with the projector 25.

The display device (the hand-held terminal 5) is detachable/reattachable with respect to a casing of the projector 25. Thus, the user can use the display device removed from the projector 25. Further, since the display device is a hand-held type information processing apparatus, the user can carry and use the display device. In addition, the display device is communicable with an external device (the server 3) via a network by accessing the network through wireless communication. Thus, the user can use the display device outdoors (e.g., the user can cause the display device to display a content acquired from the server 3 through communication).

In the embodiment described above, the base device 6 which is one example of the display device includes the sensor (the Doppler sensor 24) for sensing the biological information of the user, and the projector 25 that is disposed in the same casing as that for the sensor, and projects and displays a predetermined image (FIG. 2, FIG. 3). With this, a display that is easy to view by the user in bed can be provided by the projector 25. In addition, the biological information of the user can be sensed by the sensor.

The Doppler sensor 24 senses biological information from a user who is away from the base device 6 within a predetermined range. With this, the biological information can be sensed from a user in the vicinity of the display device without making the user aware of the sensing operation by the sensor.

In addition, the base device 6 is a stationary type device which is used in the placed state during sensing by the Doppler sensor 24. Thus, the user only has to place the display device in a place where sensing by the sensor is performed, and the user need not perform a troublesome setting operation for sensing by the sensor.

The base device 6 may further include the loudspeaker 26 disposed in the same casing as that for the Doppler sensor 24 and the projector 25. With this, a sound (e.g., a sound matched with the image projected and displayed by the projector 25) can be presented to the user in bed. Since a separated loudspeaker need not be prepared, the configuration of the system can be simplified.

(Functions and Effects Related to Calculation of Emotion Information)

In the embodiment described above, the hand-held terminal 5 includes the sensing section (the microphone 15 and the camera 16) that senses the sensor information for determining the emotion of the user. The information processing system 1 determines the emotion of the user on the basis of the sensor information (step S26, step S77, step S87). The sensing section senses the sensor information in a period during which the hand-held terminal 5 is in a standby state.

The "standby state" is, for example, a state in which the display 17 of the hand-held terminal 5 is turned off (in other words, a state in which an operation has not been performed on the hand-held terminal 5 for a predetermined time period). In the standby state, an application may be being execute. In the description above, the sensing section only has to be able to sense the sensor information in the standby state. The sensing section need not constantly sense the sensor information in the standby state. In addition, the sensing section may sense the sensor information in a state (e.g., a state in which the user operates the hand-held terminal 5) different from the standby state.

Further, in the embodiment described above, the sensor information is a sound sensed by the microphone 15, and an image captured by the camera 16. However, the sensor information may be biological information of user, for example. For example, pulse of the user may be sensed as the biological information, and the emotion of the user (whether the user is excited or calm) can be determined on the basis of the pulse. Alternatively, for example, the sweating state of the user may be sensed when the user touches the hand-held terminal 5, and the emotion of the user can be determined on the basis of the sweating state. In a case where the hand-held terminal 5 includes an acceleration sensor, the information processing system 1 may calculate the posture and/or the walking manner of the user on the basis of a sensing result from the acceleration sensor, and may calculate the emotion information on the basis of the posture and/or the walking manner of the user. For example, when, regarding the posture, the user walks with his/her back being hunched more than usual, or when, regarding the walking manner, the user walks slower than usual (plods along), the information processing system 1 may calculate the emotion information indicating that the user is depressed.

With the configuration described above, the information processing system 1 can determine the emotion of the user of the hand-held terminal 5 on the basis of the sensor information. Since the sensor information is sensed when the hand-held terminal 5 is in the standby state, the information processing system 1 can acquire the sensor information in a period during which the user is not aware of sensing of the sensor information being performed, and can determine the emotion of the user in the period. Thus, the emotion of the user, which arises in daily life of the user carrying the hand-held terminal 5, can be determined.

The hand-held terminal 5 acquires user-related information (schedule information, positional information, and/or activity information, etc.) which is different from the sensor information and relates to the user (step S71), and controls, on the basis of the user-related information, whether or not to perform sensing of the sensor information (measurement by the microphone 15 and/or the camera 16) (step S72). With this, sensing of the sensor information can be performed in an appropriate situation (that is, in a situation where acquisition of the sensor information that enables determination of the emotion is estimated).

The hand-held terminal 5 acquires information (schedule information, positional information, and/or activity information, etc.) representing the behavior and/or activity of the user, as the user-related information. With this, the information processing system 1 can assess whether or not to perform sensing of the sensor information, by taking into consideration the behavior or activity of the user.

The hand-held terminal 5 judges whether or not the current time is in a period during which a predetermined event (e.g., meeting) related to the user is performed, on the basis of the user-related information. The sensor information is sensed in the period during which the predetermined event is performed. With this, the information processing system 1 can determine the emotion of the user in the period of the event such as meeting or movement, for example.

The sensing section is operable in at least a first sensing mode (a state in which a process loop of steps S81 to S83 is executed) for sensing the sensor information at a relatively long time interval, and a second sensing mode (a state in which a process loop of steps S85 and S86 is executed) for continuously sensing the sensor information. The hand-held terminal 5 switches the operation mode of the sensing section to the second sensing mode in a case where the sensor information sensed in the first sensing mode satisfies a predetermined condition (in a case where a judgment result in step S82 is positive). The information processing system 1 determines the emotion of the user on the basis of the sensor information sensed in the second mode (step S87). With the configuration described above, the information processing system 1 can control whether or not to perform sensing of the sensor information by using the sensor information, without using the above-described user-related information.

The second sensing mode may be a mode in which the sensor information is sensed at a relatively short time interval (as compared to the first sensing mode).

The hand-held terminal 5 judges whether or not the user is operating the hand-held terminal (step S72). The sensing section senses the sensor information when the user is judged to be operating the hand-held terminal 5 (step S73). With this, the emotion of the user who is operating the hand-held terminal 5 can be determined (in addition to the emotion of the user when the hand-held terminal 5 is in the standby state).

In the embodiment described above, the information processing system 1 senses the sensor information for determining the emotion of the user (step S74, step S85), determines the emotion of the user on the basis of the sensor information (step S77, step S87), and presents the user with suggestion information (service data) for performing suggestion to the user in accordance with a determination result of the emotion (step S117, step S104). With the configuration described above, the information processing system 1 can determine the emotion of the user on the basis of the sensor information to acquire useful information, that is, the emotion of the user. In addition, the information processing system 1 can perform, for the user, suggestion taking into consideration the emotion of the user.

The information processing system 1 presents the suggestion information once a predetermined period of time (once a day) (step S9), and generates the suggestion information in accordance with the determination result of the emotion based on the sensor information sensed in the predetermined period of time. With this, suggestion in accordance with the determination result of the emotion can be periodically performed for the user.

In another embodiment, the information processing system 1 may sense the sensor information in a period (a period from step S24 to step S25) during which an event is performed, and may present the user with the suggestion information in response to the end of the period of the event. With this, suggestion in accordance with the determination result of the emotion can be performed for the user after the event has ended. Thus, the suggestion can be performed at an appropriate timing.

The server 3 stores, in a predetermined storage section, identification information (notification user data) of another user different from the user for which determination of emotion has been performed, as a user to be presented with the suggestion information, in association with the user for which determination of emotion has been performed. The server 3 presents information (emotion information) indicating a determination result of emotion of a certain user and suggestion information (emotion index) in accordance with the determination result, to another user (notification-subject user) associated with the certain user (step S117). With this, the information processing system 1 can perform, for another user different from the user himself/herself who is the subject of emotion determination, suggestion in accordance with the emotion of the user himself/herself. For example, since information related to the emotion of a user is useful information for family, friends, and the like of the user, the useful information can be provided to the family, friends, and the like.

The server 3 presents, as suggestion information in accordance with a determination result of emotion of a certain user, a first suggestion information (information shown in FIG. 25) to the certain user, and presents a second suggestion information (information shown in FIG. 28) different from the first suggestion information to another user associated with the certain user.

Further, in the embodiment described above, the hand-held terminal 5 repeatedly senses the sensor information for determining the emotion of the user (step S74, step S85), and determines the emotion of the user in a predetermined monitoring period (measurement period) on the basis of a plurality of sensor information sensed during the monitoring period (step S77, step S87). The information processing system 1 presents the determination result of the emotion to the user. The monitoring period may be set in any way, and any setting method may be adopted. The monitoring period may be, for example, a period from a predetermined start time to a predetermined end time.

With the configuration described above, the information processing system 1 can determine the emotion of the user of the hand-held terminal 5 on the basis of the sensor information. In addition, since the sensor information is sensed during the monitoring period, the information processing system 1 can determine the emotion of the user during a specific monitoring period in the daily life of the user.

The hand-held terminal 5 acquires user-related information (schedule information, positional information and/or activity information, etc.) which is different from the sensor information and relates to the user, and determines the monitoring period on the basis of the user-related information. With this, for example, a period (e.g., meeting time or meal time) during which the user conducts a certain behavior can be determined as the monitoring period, whereby a period for sensing the sensor information can be appropriately set.

The hand-held terminal 5 judges whether or not the user is operating the hand-held terminal 5 (steps S72, S76). The information processing system 1 performs determination of the emotion for, as the monitoring period, a period during which the user is judged to be operating the hand-held terminal 5 (steps S74, S77). With this, the emotion of the user can be determined while the user is operating the hand-held terminal 5. In addition, when the hand-held terminal 5 includes a camera, the face of the user can be captured by the camera if the user is operating the hand-held terminal 5. Thus, the emotion of the user can be determined from the facial expression of the user.

In the embodiment described above, the information processing system 1 senses the sensor information for determining the emotion of the user (step S74, step S85), and determines the emotion of the user on the basis of the sensor information (step S77, step S87). In addition, the information processing system 1 acquires life information (positional information, activity information, health information, environment sensor information, environmental information, and preference information) which is obtained by observing the life of the user, and executes a predetermined process (evaluation of QOL, and specification of service content in a network service) on the basis of a determination result of emotion, and the life information (steps S115, S116).

The "life information" may be any information obtained by observing the life of the user. The life information may be some of the above-described positional information, activity information, health information, environment sensor information, environmental information, and preference information described above, or may be other types of information. In addition, the "predetermined process" may have any content. The predetermined process may be any other process than the process of performing evaluation related to the user and the process of specifying the service content which are described above.

With the configuration described above, the information processing system 1 can determine the emotion of the user of the hand-held terminal 5 on the basis of the sensor information. In addition, the information processing system 1 can perform a process reflecting the life and emotion of the user, by using the determination result of the emotion and the life information.

The information processing system 1 executes, as the predetermined process described above, a process of calculating an index indicating the state of the user on the basis of the determination result of the emotion and the life information (step S115). With this, the information processing system 1 can calculate a useful index reflecting the QOL of the user.

The information processing system 1 executes, as the above-described predetermined process, a process of generating suggestion information (advice information, recommendation information) for performing suggestion to the user, on the basis of the determination result of the emotion and the life information (step S116), and presenting the suggestion information to the user (step S117). With this, useful suggestion can be presented to the user, taking into consideration the life and emotion of the user.

The information processing system 1 controls whether or not to perform sensing of the sensor information, on the basis of the life information, and calculates an index (emotion index, QOL index, etc.) indicating the state of the user. With this, the information processing system 1 can assess whether or not to perform sensing of the sensor information, on the basis of the life information, whereby this assessment can be appropriately performed.

The information processing system 1 acquires the life information in a period at least a part of which overlaps with the period during which the sensor information is sensed (FIG. 10). With this, the information processing system 1 can perform a process reflecting the emotion of the user in a certain period, and the life information of the user in this period.

In the embodiment described above, the hand-held terminal 5 includes the sensing section (the microphone 15 and the camera 16) which senses the sensor information for determining the emotion of the user. The information processing system 1 determines the emotion of the user on the basis of the sensor information, and accumulates a result of the determination of the emotion in the storage section included in the server 3.

The hand-held terminal 5 identifies the voice of the user included in the sound sensed by the microphone 15, and determines the emotion of the user on the basis of the voice of the user (step S77, step S87). With this, since the emotion of the user is determined on the basis of the voice of the user himself/herself of the hand-held terminal 5, the emotion can be accurately determined.

The hand-held terminal 5 may identify the voice of a person other than the user, which voice is included in the sound sensed by the microphone 15, and may determine the emotion of the user on the basis of the voice of the other person (step S77, step S87). With this, since the emotion of the user of the hand-held terminal 5 can be determined on the basis of the voice of a person other than the user, the emotion of the user can be determined even in a situation where the emotion of the user cannot be determined from his/her voice. Thus, the emotion of the user can be determined in more situations.

The hand-held terminal 5 may determine the emotion of the user in accordance with the surrounding atmosphere of the user, on the basis of the sound sensed by the microphone 15. With this, the emotion of the user of the hand-held terminal 5 can be determined even in a situation where the emotion of the user cannot be determined from his/her voice. Thus, the emotion of the user can be determined in more situations.

With the configuration described above, the information processing system 1 can determine the emotion of the user of the hand-held terminal 5 on the basis of the sensor information. In addition, the emotion information is useful information since various types of services can be provided to the user by analyzing or evaluating the emotion information, and becomes further useful information if there are multiple sets of the emotion information (which may be multiple sets of the emotion information for a single user, or multiple sets of the emotion information for multiple users). In the embodiment described above, since the calculated emotion information is accumulated in the server 3, a large number of sets of the emotion information, which is useful information, can be easily managed without placing a large burden on the storage capacity of the hand-held terminal 5.

8. Modifications (Modifications related to Configuration of Terminal System)

In the embodiment described above, the terminal system 2 is configured to include one hand-held terminal 5 and one base device 6. In another embodiment, the terminal system 2 may be configured to include a plurality of hand-held terminals 5 and one base device 6. That is, the terminal system 2 may have a configuration in which a plurality of users (e.g., a plurality of users in a family) each carry the hand-held terminal 5, and only one base device 6 is provided for the plurality of hand-held terminals 5. In this case, the base device 6 may sense the biological information of one specific user (e.g., a user of the hand-held terminal 5 connected to the base device 6). When the base device 6 is able to sense the biological information from the plurality of users, the base device 6 may sense the biological information of each user.

In the embodiment described above, the hand-held terminal 5 can be used in combination with any base device 6. That is, in the embodiment described above, since the information sensed by the base device 6 is transmitted to the server 3 through the hand-held terminal 5, this information can be specified to be information related to the user of the hand-held terminal 5. Thus, as long as the relationship between the hand-held terminal 5 and the user is fixed, the base device 6 can be used by any user (any hand-held terminal 5). For example, when the base device 6 is placed in a hotel room as well as at the home of the user, the information processing system 1 can calculate the health information also when the user sleeps in places other than the home.

In another embodiment, the information processing system 1 may fix the combination of the hand-held terminal 5 and the base device 6. For example, by performing an authentication process when connecting the hand-held terminal 5 and the base device 6, only a specific base device 6 can be made available for a specific hand-held terminal 5.

(Modification Related to Function of Each Apparatus Included in Information Processing System 1)

In the embodiment described above, each of the processes in the information processing system 1 is executed by the base device 6, the hand-held terminal 5, and the server 3. Each of the processes in the information processing system 1 may be executed by any of the three components (the base device 6, the hand-held terminal 5, and the server 3).

The base device 6 transmits the information sensed by the sensor to the hand-held terminal 5. In another embodiment, the base device 6 may transmit information calculated from the sensed information. For example, the base device 6 may transmit calculated biological information regarding respiration and/or body movement to the hand-held terminal 5, or may transmit a calculated sleep index to the hand-held terminal 5, or may transmit calculated health information (a sleep index and a fatigue index) to the hand-held terminal 5. Further, the base device 6 may transmit (an index representing) a calculated evaluation result based on the health information to the hand-held terminal 5.

The hand-held terminal 5 may transmit information received from the base device 6 and/or information sensed by itself to the server 3, or may transmit information calculated from these pieces of information to the server 3. In the latter case, in the embodiment described above, the hand-held terminal 5 calculates the QOL factor information and transmits the QOL factor information to the server 3. In another embodiment, the hand-held terminal 5 may perform evaluation based on the QOL factor information and transmit (an index representing) an evaluation result to the server 3.

The server 3 may receive, from the hand-held terminal 5, information sensed by the base device 6 and/or the hand-held terminal 5. In this case, the server 3 calculates an evaluation result on the basis of the sensed information. In addition, the server 3 may calculate an evaluation result on the basis of information (biological information regarding respiration and/or body movement, a sleep index, and QOL factor information, etc.) calculated from the sensed information, or may receive the evaluation result from the hand-held terminal 5.

In a case where multiple types of QOL factor information are calculated or multiple types of evaluations are performed as in the embodiment described above, some QOL factor information (or some evaluation results) among the multiple types of QOL factor information (or multiple evaluation results) may be calculated by the hand-held terminal 5, while the remaining QOL factor information (or remaining evaluation results) may be calculated by the server 3.

(Modification Related to Base Device)

In the embodiment described above, the base device 6 is configured to be connected to the network 4 via the hand-held terminal 5. In another embodiment, the base device 6 may be configured to include a communication section communicable with the network 4. In this case, the base device 6 may communicate with the server 3 without involving the hand-held terminal 5. For example, the base device 6 may transmit information sensed by the sensor (or information calculated from the information) to the server 3 without involving the hand-held terminal 5. In addition, for example, the base device 6 may receive service data from the server 3 without involving the hand-held terminal 5. Further, the base device 6 may cause the projector 25 to project and display an image (e.g., the content for sleep onset or the content for awakening described above) on the basis of the service data, and/or an image transmitted from the server 3.

In the embodiment described above, the base device 6 is configured to include the projector 25 and the loudspeaker 26 which is one example of the output device. In another embodiment, the base device 6 may include another configuration as the output device. For example, the base device 6 may include a light emitting device that emits light. The light emitting device is a light source that irradiates the user with light, and may be an illumination device, for example. The illumination device may be integrated with or separated from the main body of the base device 6.

The terminal system 2 may control the illumination device in accordance with the sleep state of the user. For example, the illumination device may be lit up when the user has entered a state prior to awakening (or when the user has awakened). Specifically, the terminal system 2 starts lighting of the illumination device (irradiation of the light source) at a timing before the user awakens, which is a timing specified on the basis of the biological information. With this, the user can be encouraged to wake up by irradiating the user in the state prior to awakening with light. In the description above, after the illumination device is lit up, the terminal system 2 may control the illumination device to gradually increase the brightness. Alternatively, the terminal system 2 may encourage the user to wake up by light emission of the projector 25, instead of (or as well as) encouraging the user to wake up by light emission of the illumination device.

A point in time when the user awakens may be calculated (specified) by any method other than calculation based on the biological information. For example, when user has set the time of an alarm clock with respect to the terminal system 2 (the hand-held terminal 5), the terminal system 2 may use the time as a point in time when the user awakens. Thus, the terminal system 2 which is one example of the display system may include: the projector that projects and displays an image related to the sleep of the user; the light source that irradiates the user with light; and the control section that specifies a point in time when the user awakens and starts irradiation of the light source at a timing based on the point in time. With this, a display that is easy to view by the user in bed can be provided by the projector 25, and the user in the state prior to awakening can be encouraged to wake up by being irradiated with light.

In another embodiment, a service to be provided as a network service may be performed (provided) in the base device 6. That is, the base device 6 may perform a predetermined output on the basis of service data received by the hand-held terminal 5. This predetermined output may be at least one of image, light, sound, and odor, for example. For example, the server 3 may transmit the content for sleep onset and/or the content for awakening described above, as service data to the hand-held terminal 5, and these contents may be reproduced by the projector 25 and/or the loudspeaker 26 of the base device 6. That is, the projector 25 may project and display an image based on the service data. The loudspeaker 26 may output a sound based on the service data.

For example, the base device 6 may include an odor generation device that generates odors. In this case, the odor generation device may be controlled on the basis of the service data received by the hand-held terminal 5. Specifically, the service data indicating the type of an odor is received by the hand-held terminal 5. Thereafter, when the hand-held terminal 5 becomes communicable with the base device 6, the base device 6 controls the odor generation device to output the odor of the type indicated by the service data. Thus, the terminal system 2 can provide the user with the odor in accordance with the evaluation result of the day during sleep, thereby providing the user with comfortable sleep onset environment.

In another embodiment, the base device 6 may include an environment sensor. The environment sensor may sense at least one of temperature, humidity, illumination intensity, atmospheric pressure, and sound, similarly to the environment sensor 14 included in the hand-held terminal 5. In this case, the base device 6 senses the biological information by using the Doppler sensor 24, and senses the environment sensor information by using the environment sensor. A period during which the environment sensor information is sensed only has to include at least a part of the sleeping period of the user, and may be the same as the biological information sensing period or may be the sleeping period (period from sleep onset to awakening) of the user. In addition, the base device 6 transmits the sensed environment sensor information to the hand-held terminal 5. The base device 6 may transmit the environment sensor information as it is to the hand-held terminal 5, or may process the environment sensor information in some way and transmit the processed result to the hand-held terminal 5.

The hand-held terminal 5 transmits, to the server 3, the environment sensor information from the base device 6 and/or information calculated from the environment sensor information. For example, the hand-held terminal 5 may calculate environmental information (e.g., the environmental value described above) from the environment sensor information, and transmit the environmental information to the server 3. The hand-held terminal 5 may transmit the environmental information together with the health information (the environmental information being included in the transmission information including the health information) to the server 3, or may transmit the environmental information separately from (at a timing different from that for) the health information to the server 3.

When the base device 6 includes the environment sensor, an output from the base device 6 (or the hand-held terminal 5) may be controlled on the basis of the sensing result (environment sensor information) obtained by the environment sensor. This control may be performed by the control section 22 of the base device 6, or may be performed by the processing section 11 of the hand-held terminal 5. For example, when the environment sensor includes an illumination sensor, the brightness of an image projected and displayed by the projector 25 (or the display 17 of the hand-held terminal 5) may be controlled on the basis of the sensing result obtained by the illumination sensor. That is, when the brightness (luminance) of a room which is sensed by the illumination sensor is high, the brightness of the image projected and displayed by the projector 25 may be increased. In addition, for example, when the environment sensor includes a noise sensor, the output sound volume of the loudspeaker 26 (or the loudspeaker 18 of the hand-held terminal 5) may be controlled on the basis of the sensing result of the noise sensor. That is, when the noise sensed by the noise sensor is large, the output sound volume of the loudspeaker 26 may be increased.

In another embodiment, the terminal system 2 which is one example of an output system may include a sensor (the Doppler sensor 24) that senses user information (biological information) for calculating a state regarding sleep of the user in bed, and an indirectional loudspeaker that outputs a sound for the user in bed. The indirectional loudspeaker makes the user less likely to be conscious of the position of the source of the output sound, thereby providing the user with more natural sound. The indirectional loudspeaker may be control to perform similar sound output to that of the loudspeaker 26 described above. For example, the terminal system 2 may control the indirectional loudspeaker in accordance with the state regarding sleep which is calculated on the basis of the user information (biological information). The indirectional loudspeaker may be housed in the same casing as that for the sensor, or may be separated from the sensor.

As described above, the terminal system 2 which is one example of the display system may include: the projector that projects and displays an image (the content for sleep onset, the content for awakening, the image showing the evaluation result of sleep, etc.) related to the sleep of the user; and the indirectional loudspeaker that outputs a sound (the content for sleep onset, the content for awakening, the voice showing the evaluation result of sleep, etc.) related to the sleep of the user. With this, a display that is easy to view by the user in bed can be provided by the projector 25, and more natural sound can be provided to the user by the indirectional loudspeaker.

(Modification Related to Sensor)

In the embodiments and modifications described above, the sensor that acquires the biological information of the user is a non-contact type (and unworn type) sensor (specifically, a Doppler sensor). In other words, the sensor is placed in the vicinity of a user who is a subject to be sensed. Thus, the user need not worry about the sensing operation by the sensor, whereby the burden on the user, which is caused by sensing, can be reduced. In addition, the unworn type sensor avoids a situation that the user forgets to wear the sensor and sensing is not performed.

The non-contact type (and unworn type) sensor is not limited to the Doppler sensor 24 described above. That is, in the embodiment described above, the Doppler sensor 24 emits radio waves toward the subject to be sensed and receives reflected waves, and outputs the biological information on the basis of received results (by analyzing the movement of the subject on the basis of the Doppler phenomenon of the received waves). In another embodiment, for example, the non-contact type sensor may emit radio waves toward the subject to be sensed and receive reflected waves, and may output the biological information on the basis of received results (received waves). Specifically, the sensor may acquire an image of the subject on the basis of the received waves, analyze the movement of the subject from the image information, and output the biological information. The non-contact type sensor may be a sensor that uses predetermined sensing waves such as ultrasonic waves instead of radio waves. The non-contact type sensor may be imaging means (camera) placed in the vicinity of the user. That is, the camera may capture an image of the subject from a distant location, and the information processing system may analyze the movement of the subject from the captured image to output the biological information.

(Modification Related to Network Service)

In another embodiment, a game may be provided in the server 3. A server providing a game may be the same server as the server 3, or may be a dedicated server (game server). For example, a game application may be provided to the user in the above-described website (website for providing a network service) managed by the server 3. The game application may be of a type that operates on a browser for browsing a website, or may be of a type that is downloaded from the server and installed in the hand-held terminal 5.

The game application may be provided from the server to the terminal system 2, or may be acquired by the terminal system 2 with any method. For example, a storage medium that stores the game application may be connected (or mounted) to the hand-held terminal 5 to execute the game application in the hand-held terminal 5.

The game application may be executed in the hand-held terminal 5, or may be executed in other user terminals (a hand-held terminal, a personal computer, and a game apparatus, etc.) possessed by the user.

As described above, when the game application is executed in the user terminal (the hand-held terminal 5 and/or the other user terminals described above), an evaluation result of the user may be reflected in the game. That is, as a privilege to be given to the user in the processes at steps S116 and S117, a privilege related to the game may be given to the user. For example, the server 3 may give the privilege related to the game to the user under a condition that a state in which a value indicated by a predetermined index is a good value equal to or larger than a reference value has continued for a predetermined period, or a condition that a predetermined index has been improved from a predetermined standard. The privilege related to the game may be any favor. For example, the server 3 may give an item to be utilized in the game to the user, or may advance a story in the game.

In the description above, the information processing system including the terminal system and the server executes a game process based on a game application. Here, the information processing system refers to the evaluation result (which may be information for calculating the evaluation result, that is, the user status data shown in FIG. 21) stored in the server 3 when executing the game process. Then, on the basis of the referred evaluation result (that is, in accordance with the referred result), a predetermined process in the game process is executed. The predetermined process is, for example, a process of giving the item described above, or a process of advancing the story in the game. Specifically, the information processing system performs a process of adding or updating the game data to be used in the game application. That is, a flag in the game is updated so that game data of the given item can be added, or a new story can be played.

The game process may be executed in the server-side information processing apparatus (e.g., the game server or the server 3), or may be executed in the terminal-side information processing apparatus (e.g., the hand-held terminal 5 or the other user terminals described above). Alternatively, the game process may be executed by the server-side information processing apparatus and the terminal-side information processing apparatus in cooperation with each other. That is, one part of the game process may be executed on the server side while the other part of the game process may be executed on the terminal side. For example, when the game application is operated on a browser for browsing a website, the game process is executed on the server side, or executed on the server side and the terminal side in cooperation with each other. When the game application is installed in the terminal-side information processing apparatus, or when the game application stored in the storage medium connected to the information processing apparatus is executed, the game process is executed on the terminal side, or executed on the server side and the terminal side in cooperation with each other.

Addition or update of game data may be executed on the server side, or may be executed on the terminal side. That is, a process of adding or updating game data may be executed by the server-side information processing apparatus performing addition or update for the game data stored in the server-side or terminal-side storage section. Alternatively, the process of adding or updating game data may be executed by the terminal-side information processing apparatus performing addition or update for the game data stored in the terminal-side storage section.

When the evaluation result is used (referred) in the game application as described above, the evaluation result related to the user of the game application is referred to. For example, when the game application is used in the state where the user logs in a website managed by the server 3, the server can specify the user by using user identification information (user identification data shown in FIG. 21) that is inputted at the time of log-in. That is, the server stores therein the user identification information inputted at the time of log-in, and refers to the evaluation result of the user specified by the stored user identification information when the server refers to the evaluation result in the game process.

When the game application is used in the state where the user does not log in the portal website (or when the game application is used by using a terminal different from a terminal that logs in), the server identifies the user who uses the game application before the game process or during the game process. Specifically, the user terminal that uses the game application receives, from the user, an input of the user identification information before or during the game process, and transmits the inputted user identification information to the server. The server specifies an evaluation result to be referred to, by using the user identification information from the user terminal. When addition or update of game data is executed on the server side, the server refers to the specified evaluation result, and executes a predetermined process (addition or change of game data) in the game process on the basis of the referred evaluation result. On the other hand, when addition or update of game data is executed on the terminal side, the server transmits the specified evaluation result to the user terminal. The user terminal refers to the received evaluation result (that is, refers to the evaluation result stored on the server side), and executes a predetermined process in the game process on the basis of the referred evaluation result.

In the description above, the user identification information may be not only the account of the user in the network service according to the embodiment described above, but also an account in the service that provides the game application. In this case, sharing the account of the user among a plurality of network services allows the user to use the plurality of network services in different user terminals (which may be terminals having different platforms), thereby improving usability.

As described above, an objective of the embodiment described above is, for example, to provide a user with useful information and/or service, and the embodiment can be applied to, for example, an information processing system including a hand-held terminal.

While certain example systems, methods, devices and apparatuses have been described herein, it is to be understood that the appended claims are not to be limited to the systems, methods, devices and apparatuses disclosed, but on the contrary, are intended to cover various modifications and equivalent arrangements included within the spirit and scope of the appended claims.

What is claimed is:

1. A display system, comprising:
   a sensor configured to sense user information for calculating a sleep state of a user; and
   control circuitry configured to cause the display system to display an image related to the sleep state calculated on the basis of the user information, wherein
   in response to the display system judging, based on at least biological information calculated from the sensed user information, that the user is in a sleep state prior to awakening, the control circuitry causes the display system to automatically display an image for inducing awakening of the user when the display system judges that the user is in the sleep state prior to awakening, and
   in response to the display system judging, based on at least the calculated biological information, that the user is in a state of awakening, the control circuitry switches the image displayed so as to automatically display an evaluation result of sleep for the user when the display system judges that the user is in the state of awakening.

2. The display system according to claim 1, wherein
   the control circuitry causes the display system to display the image related to the sleep state calculated on the basis of the user information, at a timing in accordance with the sleep state of the user, which is a timing specified on the basis of the user information.

3. The display system according to claim 2, wherein
   the control circuitry causes the display system to display the image related to the sleep state at a timing before the user awakens or a timing when the user awakens, which is a timing specified on the basis of the user information.

4. The display system according to claim 1, wherein
   the control circuitry changes an image for inducing sleep onset of the user and/or an image for inducing awakening of the user, in accordance with the sleep state of the user, and causes the display system to display the image.

5. The display system according to claim 1, wherein an evaluation of sleep of the user on the basis of the user information is performed, and
   the control circuitry causes the display system to display a result of the evaluation at a timing in accordance with the sleep state of the user, which is a timing specified on the basis of the user information.

6. The display system according to claim 1, further comprising a light source which irradiates the user with light, wherein
   the control circuitry starts irradiation of the light source at a timing before the user awakens, which is a timing specified on the basis of the user information.

7. The display system according to claim 1, wherein
   the sensor senses biological information of the user in a state of not being in contact with the user, and
   the sensor senses the biological information from the user who is away from the display device within a predetermined range.

8. The display system according to claim 7, wherein
   the sensor emits radio waves or sound waves toward a subject to be sensed and receives reflected waves, and outputs the biological information on the basis of a result of the reception.

9. The display system according to claim 1, wherein the sleep state prior to awakening occurs at a first timing and the state of awakening occurs at a second timing, and the image for inducing awakening of the user is displayed at the first timing, and the evaluation result is displayed at the second timing.

10. The display system according to claim 1, wherein a sleep index is calculated based on the biological information and the display system judges that the user is in the sleep state prior to awakening or that the user is in the state of awakening by using, at least, the calculated sleep index.

11. The display system according to claim 1, wherein the display system judges that the user is in the sleep state prior to awakening when the user sleep state becomes shallow as a predicted arising clock time approaches.

12. An information processing apparatus, comprising:
    a processor; and
    a memory configured to store computer readable instructions that, when executed by the processor, cause the information processing apparatus to:
    sense user information, using a sensor, for calculating a sleep state of a user;
    display an image related to the sleep state calculated on the basis of the user information;
    in response to the user being in a sleep state prior to awakening, as judged based on at least biological information calculated from the sensed user information, automatically display an image for inducing awakening of the user when the user is in the sleep state prior to awakening, and
    in response to the user being in a state of awakening, as judged based on at least the calculated biological information, switch the image displayed so as to automatically display an evaluation result of sleep for the user when the user is in the state of awakening.

13. A non-transitory computer readable storage medium having stored therein computer readable instructions that, when executed by a processor of an information processing system, cause the information processing system to provide execution comprising:
sensing user information, using a sensor, for calculating a sleep state of a user;
displaying an image related to the sleep state calculated on the basis of the user information;
in response to the user being in a sleep state prior to awakening, as judged based on at least biological information calculated from the sensed user information, automatically displaying an image for inducing awakening of the user when the user is in the sleep state prior to awakening, and
in response to the user being in a state of awakening, as judged based on at least the calculated biological information, switching the image displayed so as to automatically display an evaluation result of sleep for the user when the user is in the state of awakening.

14. A method for displaying an image related to a sleep state of a user, comprising:
sensing user information, using a sensor, for calculating a sleep state of a user;
displaying an image, using a display device, related to the sleep state calculated on the basis of the user information;
in response to the user being in a sleep state prior to awakening, as judged based on at least biological information calculated from the sensed user information, automatically displaying an image for inducing awakening of the user when the user is in the sleep state prior to awakening, and
in response to the user being in a state of awakening, as judged based on at least the calculated biological information, switching the image displayed so as to automatically display an evaluation result of sleep for the user when the user is in the state of awakening.

15. A display system, comprising:
a sensor configured to sense user information for calculating a sleep state of a user; and
control circuitry configured to cause the display system to display an image related to the sleep state calculated on the basis of the user information, wherein
in response to the display system judging that the user experiences an awakening in mid-course of sleep at a first timing, the control circuitry causes the display system to automatically select a first image to display when the display system judges that the user experiences the awakening in mid-course of sleep at the first timing, and
in response to the display system judging that the user experiences an awakening that is not in mid-course of sleep at a second timing, the control circuitry causes the display system to automatically alternatively select a second image to display when the display system judges that the user experiences the awakening that is not in mid-course of sleep at the second timing.

16. An information processing apparatus, comprising:
a processor; and
a memory configured to store computer readable instructions that, when executed by the processor, cause the information processing apparatus to:
sense user information, using a sensor, for calculating a sleep state of a user;
display an image related to the sleep state calculated on the basis of the user information;
in response to the user experiencing an awakening in mid-course of sleep at a first timing, as judged based on at least biological information calculated from the sensed user information, automatically select a first image to display when the user experiences the awakening in mid-course of sleep at the first timing, and
in response to the user experiencing an awakening that is not in mid-course of sleep at a second timing, as judged based on at least the calculated biological information, automatically alternatively select a second image to display when the user experiences the awakening that is not in mid-course of sleep at the second timing.

17. A non-transitory computer readable storage medium having stored therein computer readable instructions that, when executed by a processor of an information processing system, cause the information processing system to provide execution comprising:
sensing user information, using a sensor, for calculating a sleep state of a user;
displaying an image related to the sleep state calculated on the basis of the user information;
in response to the user experiencing an awakening in mid-course of sleep at a first timing, as judged based on at least biological information calculated from the sensed user information, automatically selecting a first image to display when the user experiences the awakening in mid-course of sleep at the first timing, and
in response to the user experiencing an awakening that is not in mid-course of sleep at a second timing, as judged based on at least the calculated biological information, automatically alternatively selecting a second image to display when the user experiences the awakening that is not in mid-course of sleep at the second timing.

18. A method for displaying an image related to a sleep state of a user, comprising:
sensing user information, using a sensor, for calculating a sleep state of a user;
displaying an image, using a display device, related to the sleep state calculated on the basis of the user information;
in response to the user experiencing an awakening in mid-course of sleep at a first timing, as judged based on at least biological information calculated from the sensed user information, automatically selecting a first image to display when the user experiences the awakening in mid-course of sleep at the first timing, and
in response to the user experiencing an awakening that is not in mid-course of sleep at a second timing, as judged based on at least the calculated biological information, automatically alternatively selecting a second image to display when the user experiences the awakening that is not in mid-course of sleep at the second timing.

19. The display system according to claim 1, wherein in response to the display system judging that the user is in the state of awakening, the control circuitry automatically switches the image displayed for inducing awakening of the user to display the evaluation result of the sleep for the user.

20. The display system according to claim 1, wherein a sleep index of the user is determined and the evaluation result of the sleep for the user is generated based on the sleep index of the user.

* * * * *